United States Patent
Powell et al.

(10) Patent No.: US 11,208,689 B2
(45) Date of Patent: *Dec. 28, 2021

(54) DNA MUTATION DETECTION EMPLOYING ENRICHMENT OF MUTANT POLYNUCLEOTIDE SEQUENCES AND MINIMALLY INVASIVE SAMPLING

(71) Applicants: Michael J Powell, Alamo, CA (US); Aiguo Zhang, San Ramon, CA (US); Michael Y Sha, Castro Valley, CA (US); Ke Zhan, San Mateo, CA (US)

(72) Inventors: Michael J Powell, Alamo, CA (US); Aiguo Zhang, San Ramon, CA (US); Michael Y Sha, Castro Valley, CA (US); Ke Zhan, San Mateo, CA (US)

(73) Assignee: DIACARTA LTD

( * ) Notice: Subject to any disclaimer, the term of this patent is extended or adjusted under 35 U.S.C. 154(b) by 0 days.

This patent is subject to a terminal disclaimer.

(21) Appl. No.: 16/510,722

(22) Filed: Jul. 12, 2019

(65) Prior Publication Data
US 2019/0330692 A1    Oct. 31, 2019

Related U.S. Application Data

(63) Continuation-in-part of application No. 14/822,874, filed on Aug. 10, 2015, now Pat. No. 10,400,277, and a continuation-in-part of application No. 15/786,591, filed on Oct. 17, 2017, and a continuation-in-part of application No. 15/862,581, filed on Jan. 4, 2018, now abandoned.

(60) Provisional application No. 62/376,206, filed on Aug. 17, 2016, provisional application No. 62/376,287, filed on Aug. 17, 2016, provisional application No. 62/442,898, filed on Jan. 5, 2017, provisional application No. 62/010,339, filed on Jun. 10, 2014, provisional application No. 62/010,357, filed on Jun. 10, 2014, provisional application No. 62/010,359, filed on Jun. 10, 2014.

(51) Int. Cl.
| | | |
|---|---|---|
| *C12Q 1/6858* | (2018.01) | |
| *C12Q 1/6874* | (2018.01) | |
| *C40B 40/06* | (2006.01) | |
| *C12Q 1/6827* | (2018.01) | |
| *C12Q 1/686* | (2018.01) | |

(52) U.S. Cl.
CPC .......... *C12Q 1/6858* (2013.01); *C12Q 1/686* (2013.01); *C12Q 1/6827* (2013.01); *C12Q 1/6874* (2013.01); *C40B 40/06* (2013.01); *C12Q 2525/101* (2013.01); *C12Q 2525/185* (2013.01); *C12Q 2527/107* (2013.01); *C12Q 2527/113* (2013.01); *C12Q 2531/113* (2013.01)

(58) Field of Classification Search
CPC .. C12Q 1/6858; C12Q 1/6874; C12Q 1/6827; C12Q 1/686; C12Q 2531/113; C12Q 2527/107; C12Q 2527/113; C12Q 2525/185; C12Q 2525/101; C40B 40/06
See application file for complete search history.

(56) References Cited

PUBLICATIONS

Dicarta, Inc., Instruction Manual for QCLAMP KRAS Codon Specific Mutation Detection Kit, pp. 1-24, (Year: Dec. 2013).*

* cited by examiner

*Primary Examiner* — Cynthia B Wilder
(74) *Attorney, Agent, or Firm* — Isaac A Angres

(57) ABSTRACT

The invention relates to a method for enriching a target polynucleotide sequence containing a genetic variation said method comprising: (a) providing two primers targeted to said target polynucleotide sequence; (b) providing a target specific xenonucleic acid clamp oligomer specific for a wildtype polynucleotide sequence; (c) generating multiple amplicons using PCR under specific temperature cycling conditions; and (d) detecting said amplicons. We introduce a novel molecule, Xenonucleic Acid (XNA) for the NGS library preparation. XNA is able to selectively suppress amplification of DNA with wild type alleles and amplify DNA containing mutant alleles. Mutants with low allelic frequency will be easily detectable without deep sequencing after enrichment by adding XNA in multiplex PCR. The 17 actionable mutants related to lung or colorectal cancer diseases at different variant allelic frequency (VAF) % were investigated. Clinical sensitivity is significantly improved with XNA in various types of samples.

12 Claims, 23 Drawing Sheets

Specification includes a Sequence Listing.

Figure 1. The modified DNA oligo probe binds—or clamps—to wild-type DNA and blocks further wild-type DNA amplification. This probe, or XNA "clamp," does not bind to mutated DNA, allowing it to be amplified and detected.

Figure 4

FLUOROPHORE SPECTRAL DATA AND QUENCHER SELECTION GUIDE

| Fluorophore | Color | Absorbance max (nm) | Emission max (nm) | Quencher Guide |
|---|---|---|---|---|
| 6-FAM (Fluorescein) | Green | 494 | 525 | BHQ-1/Dabcyl |
| TET | Orange | 521 | 536 | BHQ-1/Dabcyl |
| HEX | Pink | 535 | 556 | BHQ-1/Dabcyl |
| Cy 3 | Red | 552 | 570 | BHQ-2 |
| Cy 3.5 | Purple | 588 | 604 | BHQ-2 |
| Cy 5 | Violet | 646 | 667 | BHQ-3 |
| Cy 5.5 | Blue | 683 | 707 | BHQ-3 |
| Cy 7 | Near IR | 743 | 767 | BHQ-3 |
| Tamra | Rose | 565 | 580 | BHQ-2 |
| ROX | Purple | 587 | 607 | BHQ-2 |
| JOE | Mustard | 528 | 554 | BHQ-1/Dabcyl |
| Texas Red-X | Red | 583 | 603 | BHQ-2 |
| Cascade Blue | Blue | 396 | 410 | BHQ-1/Dabcyl |
| Marina Blue | Blue | 362 | 459 | BHQ-1/Dabcyl |

DNA MUTATION DETECTION EMPLOYING ENRICHMENT OF MUTANT POLYNUCLEOTIDE SEQUENCES AND MINIMALLY INVASIVE SAMPLING

This application is a continuation-in-part of U.S. Ser. No. 14/822,874 filed Aug. 10, 2015; U.S. Ser. No. 15/786,591 filed Oct. 17, 2017; and U.S. Ser. No. 15/862,581 filed Jan. 4, 2018; the entire contents of which are incorporated herein in their entirety. This application also claims the priority benefit under 35 U.S.C. section 119 of U.S. Provisional Patent Application No. 62/010,339 entitled "Method For Enrichment Of Target Mutant Polynucleotide Sequences" filed on Jun. 10, 2014; U.S. Provisional Patent Application No. 62/010,357 entitled "Detection Of Multiple Mutations In A Single Tube Using QCLAMP™ Assay QCLAMP™ Mplex" filed on Jun. 10, 2014; and U.S. Provisional Patent Application No. 62/010,359 entitled "Liquid Biopsy" filed on Jun. 10, 2014; which are in their entirety herein incorporated by reference. This application further claims the priority benefit under 35 U.S.C. section 119 of U.S. Provisional Patent Application No. 62/376,206 entitled "Specific Synthetic Chimeric Xenonucleic Acid Guide RNA; s(XNA-gRNA) For Enhancing CRISPR Mediated Genome Editing Efficiency" filed on Aug. 17, 2016; and Provisional Patent Application No. 62/376,287 filed Aug. 17, 2016 entitled "Synthetic Routes To Xenonucleic Acid (Xna) Monomers" which are in their entirety herein incorporated by reference. This application claims the priority benefit under 35 U.S.C. section 119 of U.S. Provisional Patent Application No. 62/442,898 entitled "Method For Conducting Early Detection Of Colon Cancer And/Or Of Colon Cancer Precursor Cells And For Monitoring Colon Cancer Recurrence" filed Jan. 5, 2017, which is in its entirety herein incorporated by reference.

FIELD OF THE INVENTION

The present invention relates to DNA mutation detection. The invention further relates to enrichment of mutant polynucleotide sequences. The present invention further relates to minimally invasive sampling and analysis of mutations in clinical samples.

The instant invention also relates to a method for determining whether a target polynucleotide sequence contained in a nucleic acid sample has nucleotide variation(s) in a selected region thereof, the steps of which involve the use of a pair of primers that allows the formation of a PCR product having a sequence covering that of the selected region of the target polynucleotide sequence via a PCR process, and a xenonucleic acid (XNA) that acts as a PCR clamp as well as a sensor probe. This invention also relates to a kit for use in determining the presence of nucleotide variation(s) in the target polynucleotide sequence, which comprises the pair of primers and the XNA.

The present embodiments relate to precision molecular diagnostics, and in particular, to compositions in detecting sequence variants, such as SNPs, insertions deletions, and altered methylation patterns, from samples. The embodiments disclosed herein can be used to detect (and quantify) sequence variants present in samples that include an excess of wild-type sequences.

BACKGROUND OF THE INVENTION

Polymerase chain reaction (PCR) is a widely used technique for the detection of pathogens. The technique uses a DNA polymerase used to amplify a piece of DNA by in vitro enzymatic replication. The PCR process generates DNA that is used as a template for replication. This results in a chain reaction that exponentially amplifies the DNA template.

Technologies for genomic detection most commonly use DNA probes to hybridize to target sequences. To achieve required sensitivity, the use of PCR to amplify target sequences has remained standard practice in many labs. While PCR has been the principle method to identify genes associated with disease states, the method has remained confined to use within a laboratory environment. Most current diagnostic applications that can be used outside of the laboratory are based on antibody recognition of protein targets and use ELISA-based technologies to signal the presence of a disease. These methods are fast and fairly robust, but they can lack the specificity associated with nucleic acid detection.

With the advent of molecular diagnostics and the discovery of numerous nucleic acid biomarkers useful in the diagnosis and treatment of conditions and diseases, detection of nucleic acid sequences, and sequence variants, mutations and polymorphisms has become increasingly important. In many instances, it is desirable to detect sequence variants or mutations (which may in some instances, differ by one a single nucleotide) present in low copy numbers against a high background of wild-type sequences. For example, as more and more somatic mutations are shown to be biomarkers for cancer prognosis and prediction of therapeutic efficacy, the need for efficient and effective methods to detect rare mutations in a sample is becoming more and more critical. In the case in which one or more allelic variants is/are present in low copy number compared to wild-type sequences, the presence of excess wild-type target sequence creates challenges to the detection of the less abundant variant target sequence. Nucleic acid amplification/detection reactions almost always are performed using limiting amounts of reagents. A large excess of wild-type target sequences, thus competes for and consumes limiting reagents. As a result amplification and/or detection of rare mutant or variant alleles under these conditions is substantially suppressed, and the methods may not be sensitive enough to detect the rare variants or mutants. Various methods to overcome this problem have been attempted. These methods are not ideal, however, because they either require the use of a unique primer for each allele, or the performance of an intricate melt-curve analysis. Both of these shortcomings limit the ability and feasibility of multiplex detection of multiple variant alleles from a single sample.

BRIEF DESCRIPTION OF THE FIGURES

FIG. 4 is a representative fluorophore spectral data and quencher selection guide.

SUMMARY OF THE INVENTION

Figure 1:
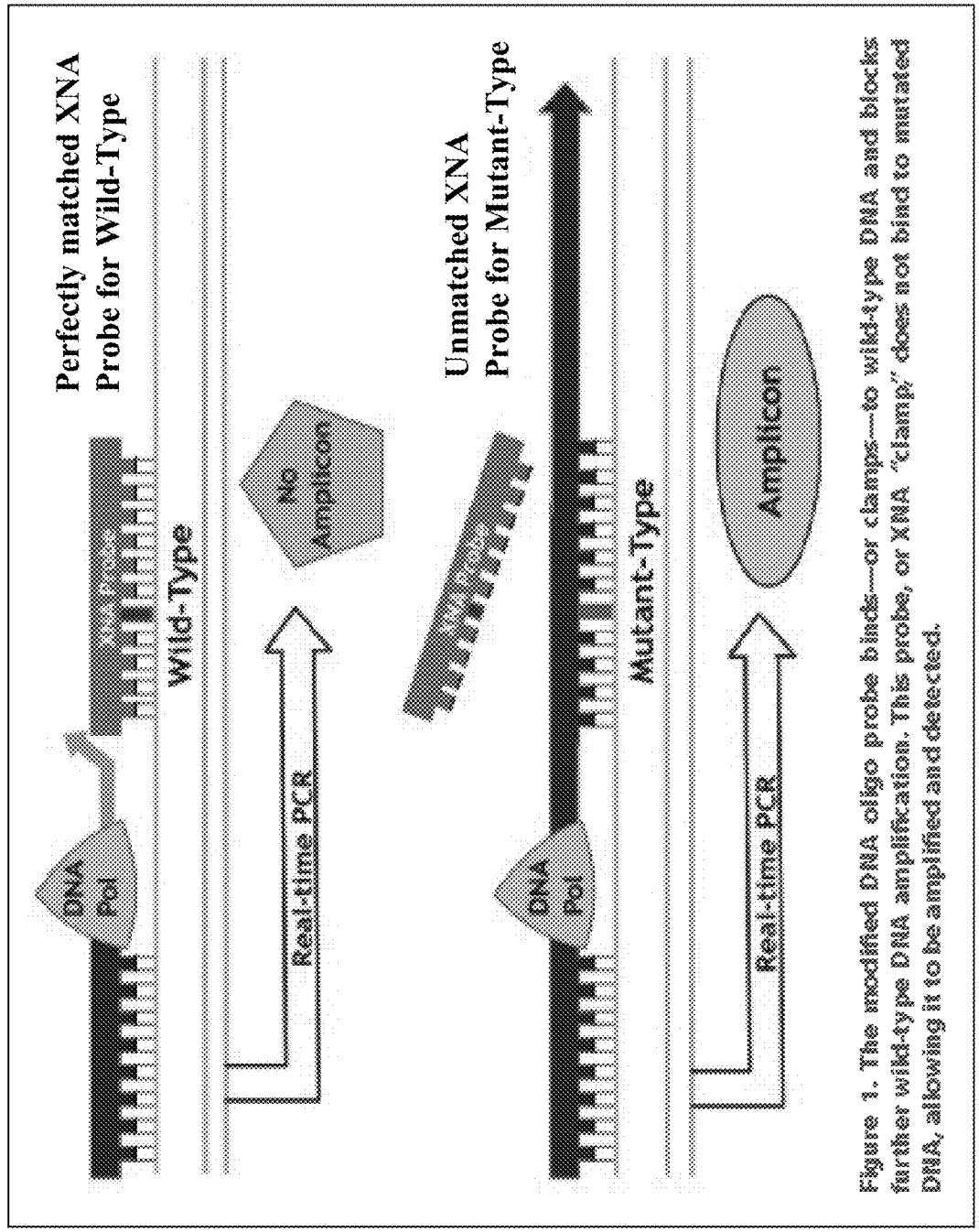
FIG. 1 illustrates the mechanism of the XNA clamping process.
Figure 2:
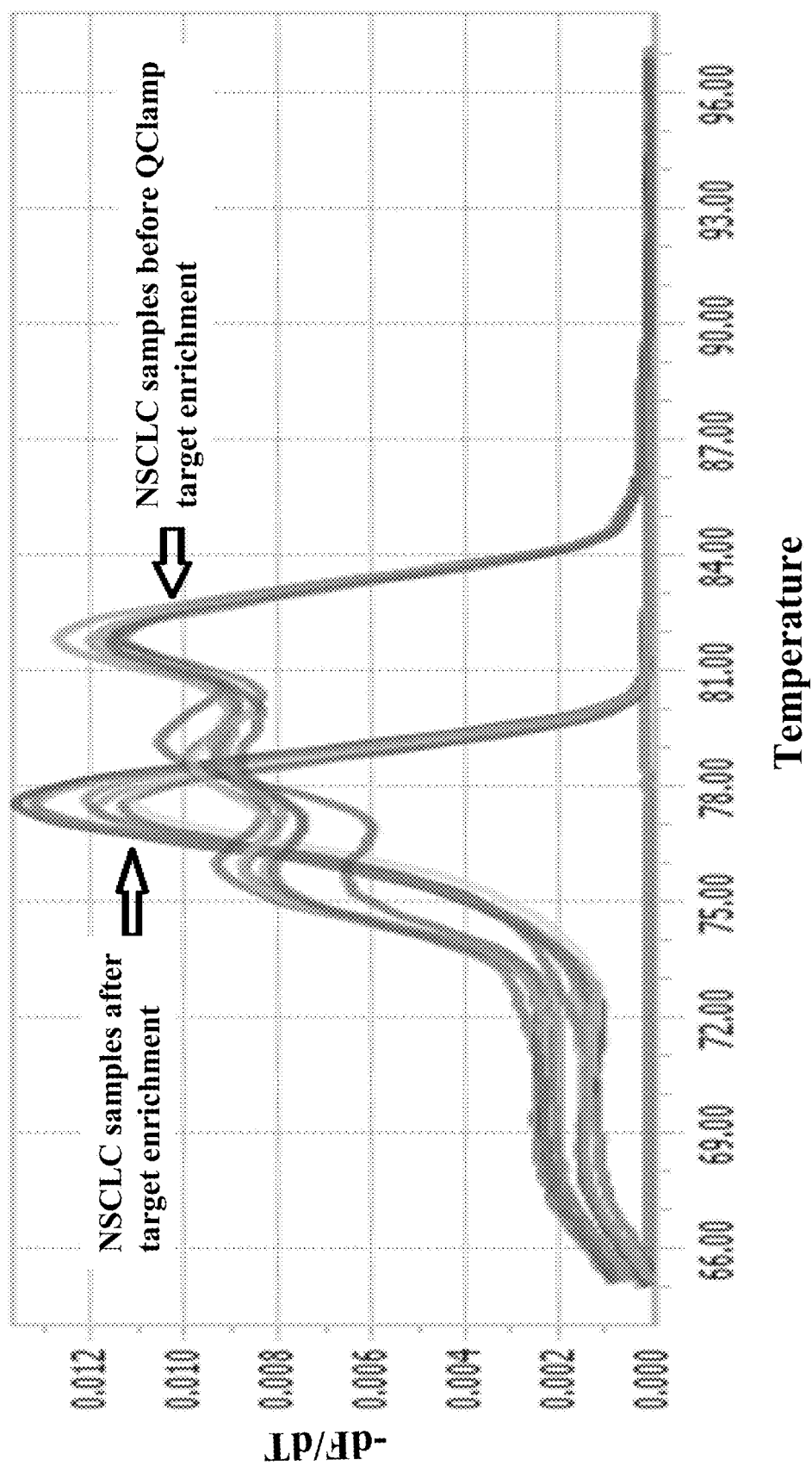
FIG. 2 shows the differential melting temperature (Tm) between the XNA clamp bound to mutant templates vs wild type templates.

Detection of rare sequence variants in biological samples presents numerous challenges. The methods and kits disclosed herein provide for improved, efficient means to detect rare mutations within a high background of wild-type allelic sequences using real-time amplification methods.

The instant invention provides a method for enriching a target polynucleotide sequence containing a genetic variation said method comprising: (a) providing two primers targeted to said target polynucleotide sequence; (b) providing a target specific xenonucleic acid clamp oligomer specific for a wildtype polynucleotide sequence; (c) generating multiple amplicons using PCR under specific temperature cycling conditions; and (d) detecting said amplicons.

The invention further provides a method for enriching a target polynucleotide sequence containing a genetic variation, said method comprising: (a) providing a biological sample; (b) isolating DNA from said biological sample; said DNA including said target polynucleotide sequence containing a genetic variation; (c) providing two primer probes targeted to said target polynucleotide sequence said primer probes allowing formation of a PCR process product; (d) providing a target specific xenonucleic acid clamp oligomer probe specific for a wildtype polynucleotide sequence; wherein said target specific xenonucleic acid clamp has oxy-aza and aza-aza moieties so that during the qPCR process only mutant templates are amplified; (e) admixing the primer probes and the xenonucleic clamping probe with the target nucleic acid sample; (f) performing a PCR amplification process in a reaction solution under hybridization conditions thereby generating multiple amplicons; and (g) detecting said amplicons.

The invention also relates to a method for enriching multiple target polynucleotide sequences containing a genetic variation said method comprising: (a) providing a library of amplifying primers targeted to said multiple target polynucleotide sequence; (b) providing a library of target specific xenonucleic acid clamp oligomer specific for multiple wildtype polynucleotide sequences; (c) generating multiple amplicons using PCR under specific temperature cycling conditions; and (d) detecting said amplicons.

The invention further relates to a method for conducting a minimally invasive biopsy in a mammalian subject suspected of a having a neoplastic disease, said method comprising: (a) sampling of target polynucleotides derived from said mammalian subject; (b) providing a library of amplifying primers targeted to said multiple target poly-nucleotide sequence; (c) providing a library of target specific xenonucleic acid clamp oligomer specific for multiple wild-type polynucleotide sequences; (d) generating multiple amplicons using PCR under specific temperature cycling conditions; and (e) detecting said amplicons.

The invention is also directed to means and methodology for the rapid isolation of genetic material from biological fluids and the sensitive detection of somatic and germ-line mutations present in circulating cells and cell-free genetic material obtained from said biological fluids using gene amplification and xeno-nucleic acid (XNA) clamping.

This invention provides a method for determining whether a target polynucleotide sequence contained in a nucleic acid sample has nucleotide variation(s) in a selected region thereof, comprising the steps of: providing a pair of a first primer and a second primer which allows the formation of a PCR product having a sequence covering that of the selected region of the target polynucleotide sequence via a PCR process, the first primer having a sequence identical to that of a first region located upstream of the selected region of the target polynucleotide sequence, the second primer having a sequence based on that of a second region located downstream of the selected region of the target polynucleotide sequence, wherein the 5'-end of the sequence of the first region is spaced apart from the 5'-end of the sequence of the selected region by 30 nucleotides or more;

providing a detectable xenonucleic acid probe having a sequence that complements fully the sequence of the selected region of the target polynucleotide sequence having no nucleotide variation(s) therein, such that hybridization of the detectable xenonucleic acid probe to the selected region of the target polynucleotide sequence having no nucleotide variation(s) results in the formation of a duplex having a melting temperature;

determining the melting temperature of the duplex;

admixing the detectable xenonucleic acid probe and the pair of the first primer and the second primer with the nucleic acid sample to form a mixture;

subjecting the mixture to a PCR process including an extension reaction set to run at a temperature lower than the melting temperature of the duplex by 5 to 20° C., such that a mixture of PCR products is obtained; and subjecting the mixture of PCR products thus-obtained to a melting analysis to determine melting temperatures of the PCR products, wherein the presence of at least one melting temperature lower than the melting temperature of the duplex is indicative of the nucleotide variation(s) in the selected region of the target polynucleotide sequence contained in the nucleic acid sample.

The invention also provides a kit for determining whether a target polynucleotide sequence contained in a nucleic acid sample has nucleotide variation(s) in a selected region thereof, comprising: a detectable xenonucleic acid probe having a sequence that complements fully the sequence of the selected region of the target polynucleotide sequence having no nucleotide variation(s) therein, such that hybridization of the detectable xenonucleic acid probe to the selected region of the target polynucleotide sequence having no nucleotide variation(s) results in the formation of a duplex having a melting temperature;

a pair of a first primer and a second primer which allows the formation of a PCR product having a sequence covering that of the selected region of the target polynucleotide sequence via a PCR process, the first primer having a sequence identical to that of a first region located upstream of the selected region of the target polynucleotide sequence, the second primer having a sequence based on that of a second region located downstream of the selected region of the target polynucleotide sequence, wherein the 5'-end of the sequence of the first region is spaced apart from the 5'-end of the sequence of the selected region by 30 nucleotides or more; and an instruction sheet providing guidance for a user to use the detectable xenonucleic acid probe and the pair of the first primer and the second primer in a method as described above.

The identification of genetic variants with low variant frequency using next-generation sequencing method is confounded by the complexity of human genome sequence and by bias that arise during library preparation, sequencing and analysis. The present invention also provides a novel molecule, Xenonucleic Acids (XNA) for the NGS library preparation. XNA is able to selectively suppress amplification of DNA with wild type alleles and amplify DNA containing mutant alleles. Mutants with low allelic frequency will be easily detectable without deep sequencing after enrichment by adding XNA in multiplex PCR. The 17 actionable mutants related to lung or colorectal cancer diseases at different VAF % have been studied in great detail in the present invention. Upon XNA blocking of wild type alleles, detectable enriched variant allelic frequency (VAF) can be increased by ~32 fold from 10 ng of gDNA samples containing mutants as low as 0.10%. Analytical sensitivity of Limit of Detection (LoD) is about 0.10% VAF. These 17 actionable mutants were tested and verified by using FFPE and cfDNA of lung or colon cancer patient samples. Clinical sensitivity for FFPE sample is about 100% for lung cancer and colorectal cancer samples respectively, comparing to without XNA NGS about 85.7% for lung cancer and 70% for colon cancer. For cfDNA sample its clinical sensitivity is about 100% for lung and early colon cancer, but without XNA NGS is about 70% for lung cancer and undetectable for early colon cancer. This invention provides a simple, accurate, higher sensitive and lower cost alternative compared with conventional NGS with deep sequencing.

DETAILED DESCRIPTION OF THE INVENTION

It is to be understood that both the foregoing general description and the following detailed description are exemplary and explanatory only and are not intended to limit the scope of the current teachings. In this application, the use of the singular includes the plural unless specifically stated otherwise. Also, the use of "comprise", "contain", and "include", or modifications of those root words, for example but not limited to, "comprises", "contained", and "including", are not intended to be limiting. Use of "or" means "and/or" unless stated otherwise. The term "and/or" means that the terms before and after can be taken together or separately. For illustration purposes, but not as a limitation, "X and/or Y" can mean "X" or "Y" or "X and Y". Whenever a range of values is provided herein, the range is meant to include the starting value and the ending value and any value or value range there between unless otherwise specifically stated. For example, "from 0.2 to 0.5" means 0.2, 0.3, 0.4, 0.5; ranges there between such as 0.2-0.3, 0.3-0.4, 0.2-0.4; increments there between such as 0.25, 0.35, 0.225, 0.335, 0.49; increment ranges there between such as 0.26-0.39; and the like.

In a first embodiment, the present invention relates to compositions and methods for the selective enrichment of low-abundance polynucleotides in a sample. These methods use xeno-nucleic acid (XNA) nucleobase oligomers to selectively block DNA polymerase activity on high abundance wild-type DNA templates, thereby resulting in enrichment of less abundant mutated DNA templates present in a biological sample during a polymerase chain reaction (PCR). The methodology of the present invention can be used to improve DNA sequencing (Sanger sequencing and Pyrosequencing) and also enhance cDNA library preparation for next generation DNA sequencing (NGS).

Utilizing xeno-nucleic acid (XNA) clamping probes in the PCR mediated amplification of DNA templates, only target genetic material that has a variation, e.g. single nucleotide polymorphism (SNP), gene deletion or insertion and/or translocation or truncation is amplified in the oligonucleotide primer directed polymerase chain reaction (qPCR).

The XNA probe clamping sequences are designed to bind specifically by Watson-Crick base pairing to abundant wild-type sequences in the DNA templates derived from the biological sample of interest. The presence of the XNA probes in the PCR primer mix employed for the target amplification reaction causes inhibition of the polymerase mediated amplification of wild-type templates but does not impede the amplification of mutant template sequences.

The mechanism of the XNA clamping process is depicted in FIG. 1. As shown in FIG. 1, the modified DNA oligo probe binds or clamps to wild type DNA and blocks further wild type amplification. This probe or XNA "clamp" does not bind to mutated DNA, allowing it to be amplified and detected.

The suppression of wild-type (wt) template amplification and amplification of only mutant templates is achieved because there is a differential melting temperature (Tm) between the XNA clamp bound to mutant templates vs wild type templates:

$$Tm(XNA\ \text{mutant template}) \ll Tm(XNA\ wt\ \text{template})$$

The Tm differential is as much as 15-20° C. for the XNA clamp probes. So that during the PCR process only mutant templates are amplified.

The methods disclosed herein can be used to analyze nucleic acids of samples. The term "sample" as described herein can include bodily fluids (including, but not limited to, blood, urine, feces, serum, lymph, saliva, anal and vaginal secretions, perspiration, peritoneal fluid, pleural fluid, effusions, ascites, and purulent secretions, lavage fluids, drained fluids, brush cytology specimens, biopsy tissue (e.g., tumor samples), explanted medical devices, infected catheters, pus, biofilms and semen) of virtually any organism, with mammalian samples, particularly human samples.

Amplification primers useful in the embodiments disclosed herein are preferably between 10 and 45 nucleotides in length. For example, the primers can be at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or more nucleotides in length. Primers can be provided in any suitable form, included bound to a solid support, liquid, and lyophilized, for example. In some embodiments, the primers and/or probes include oligonucleotides that hybridize to a reference nucleic acid sequence over the entire length of the oligonucleotide sequence. Such sequences can be referred to as "fully complementary" with respect to each other. Where an oligonucleotide is referred to as "substantially complementary" with respect to a nucleic acid sequence herein, the two sequences can be fully complementary, or they may form mismatches upon hybridization, but retain the ability to hybridize under stringent conditions or standard PCR conditions as discussed below. As used herein, the term "standard PCR conditions" include, for example, any of the PCR conditions disclosed herein, or known in the art, as described in, for example, PCR 1: A Practical Approach, M. J. McPherson, P. Quirke, and G. R. Taylor, Ed., (c) 2001, Oxford University Press, Oxford, England, and PCR Protocols: Current Methods and Applications, B. White, Ed., (c) 1993, Humana Press, Totowa, N.J. The amplification primers can be substantially complementary to their annealing region, comprising the specific variant target sequence(s) or the wild type target sequence (s). Accordingly, substantially complementary sequences can refer to sequences ranging in percent identity from 100, 99, 98, 97, 96, 95, 94, 93, 92, 91, 90, 89, 85, 80, 75 or less, or any number in between, compared to the reference sequence. Conditions for enhancing the stringency of amplification reactions and suitable in the embodiments disclosed herein, are well-known to those in the art. A discussion of PCR conditions, and stringency of PCR, can be found, for example in Roux, K. "Optimization and Troubleshooting in PCR," in Pcr Primer: A Laboratory Manual, Diffenbach, Ed. © 1995, Cold Spring Harbor Laboratory Press, Cold Spring Harbor, N.Y.; and Datta, et al. (2003) Nucl. Acids Res. 31(19):5590-5597.

Provided herein are methods useful in the detection of sequence variants, i.e., insertions, deletions, nonsense mutations, missense mutations, and the like. In the methods for detecting allelic variants or variant target sequences disclosed herein, the sample, which comprises the nucleic acids to be analyzed, are contacted with an amplification primer pair, i.e., comprising a forward primer and a reverse primer that flank the target sequence or target region containing a sequence of interest {e.g., a wild-type, mutant, or variant allele sequence) to be analyzed. By "flanking" the target sequence, it is understood that the variant or wild-type allelic sequence is located between the forward and reverse primers, and that the binding site of neither the forward nor reverse primer comprises the variant or wild-type allelic sequence to be assessed. For example, in some embodiments, the variant or wild-type allelic sequence to be assessed is removed from or positioned away from the 3' end of either oligonucleotide by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more, e.g., 100 or more, 200 or more, 300 or more, 400 or more, 500 or more, etc., nucleotides. Amplification primers that flank, but that do not overlap with, the variant target sequence or the wild-type target sequence are thus not "allele-specific" amplification primers, and are capable of amplification of various different alleles or variants of a sequence of interest. Thus, in some embodiments, the amplification primers are configured to amplify various mutant or variant alleles and wild type alleles non-preferentially. As discussed in further detail below, the addition of XNA to an amplification reaction suppresses the amplification of wild-type target sequences and enables preferential amplification of non-wild-type, e.g., variant, mutant or rare variant alleles. FIG. 1 is a depictions of exemplary method according to the embodiments disclosed herein for the detection of sequence variants. As shown in FIG. 1, amplification primers (i.e., forward primer 1 and reverse primer 2) flank the wild type and mutant allele sequences of interest, and comprise sequences common to both wild-type and mutant or variant allele sequences. Accordingly, as shown in FIG. 1, in contrast to methods that utilize allele-specific amplification primers to achieve preferential amplification of rare sequences, the present methods advantageously enable the simultaneous amplification of multiple variant sequences, using a single amplification primer pair.

In a second embodiment, the invention relates to compositions and methods for the detection of genetic variations (mutations) in DNA templates derived from biological samples with xeno-nucleic acid clamping probes. The first method employs multi-color fluorescence detection using locus specific fluorescent hybridization probes (Hyb Probes), hydrolysis (TaqMan or ZEN) probes or molecular beacons. The second method employs mutant specific amplicon capture probes immobilized on multiple bar-coded capture beads.

Current XNA clamping qPCR methodologies utilize a single tube-single mutation detection format it is preferable to detect multiple genetic variations in a single tube thus reducing the complexity of the assay and the amount of template DNA required for analysis.

This second embodiment of the invention is directed to the use of locus specific fluorescent probes designed to detect the genetic variant (mutant) amplicons generated during the XNA clamping PCR reaction. This second embodiment discloses locus specific probes that bind to mutant specific amplicons at a region upstream or downstream from the site of the mutation to be detected. Furthermore, the second embodiment discloses the use of multiplexed XNA clamping qPCR reactions that are able to detect multiple mutations (up to a maximum of 6) in one PCR reaction tube using fluorescence detection methodology.

In a third embodiment of the invention, there is provided a method the rapid isolation of genetic material present in circulating cells and also cell-free genetic material from biological fluids and the determination of genetic variations in those cells and biological fluids. Such biological fluids include: blood, serum, plasma, saliva, mucus, urine, sputum, semen or other biological secretions. In this embodiment, the invention also provides the detection of somatic and germ-line mutations in the genetic material derived from these biological fluids utilizing gene amplification and xeno-nucleic acid clamping.

Figure 6:
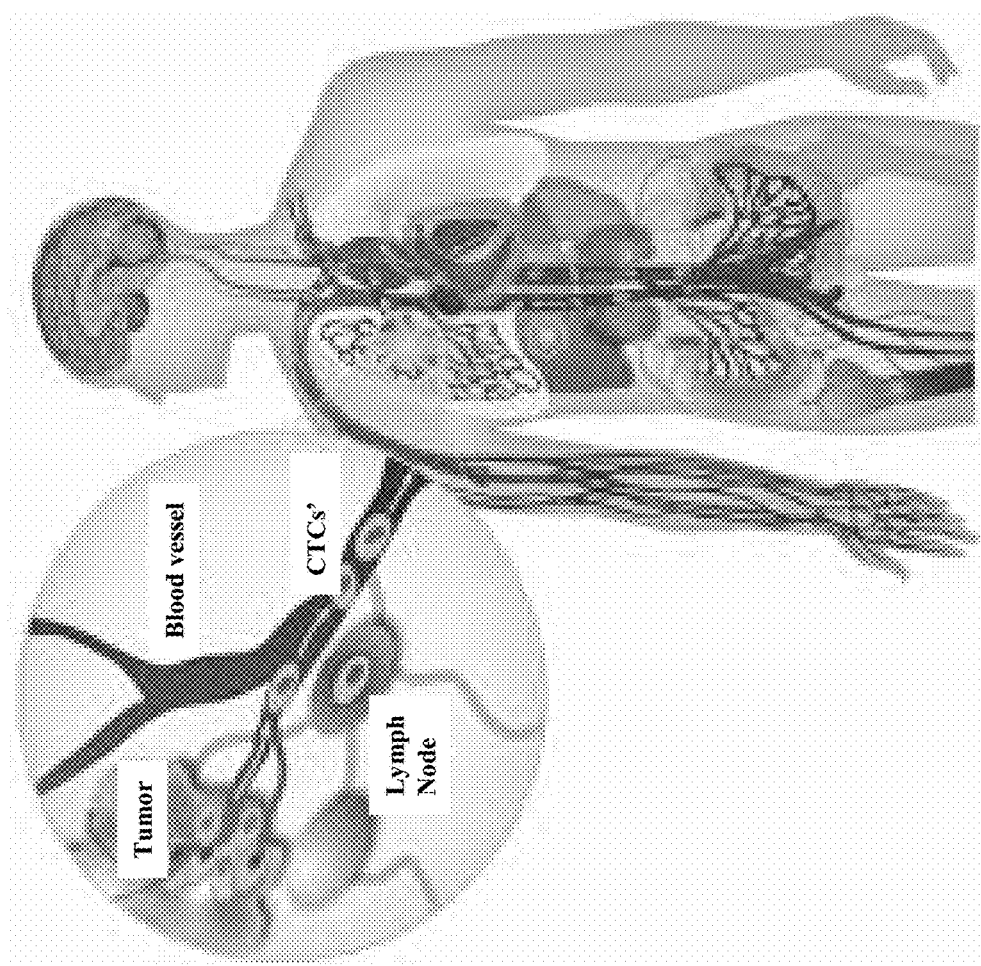
FIG. 6 is a schematic illustrating how circulating tumor cells (CTC's) and cell-free DNA (cfDNA) derived from tumor cells are present in the peripheral blood of cancer patients.

Circulating tumor cells (CTC's) and cell-free DNA (cfDNA) derived from tumor cells are present in the peripheral blood of cancer patients (See FIG. 6). Tumor derived DNA can also be found in the urine and even the saliva of cancer patients.

In general circulating free DNA is smaller in size than DNA derived directly from a surgical biopsy or FFPE sample. This embodiment also describes a novel sample treatment procedure that utilizes a novel lysis reagent called QZol™. QZol™ sample lysis is a direct one tube procedure and an aliquot of the lysate is used directly in molecular genetic and cytogenetic analysis procedures such as PCR, RTPCR, FISH, Next Generation Sequencing (NGS) and branched DNA (bDNA) assays. The QZol™ procedure eliminates the tedious multistep preanalytical processing that is currently used in Molecular Pathology and Cytogenetic analysis.

The lysis reagent is a 50% solution (A) containing chaotropic salts and detergent (nonionic, anionic, cationic or zwitterionic) and a 50% solution (B) containing neutralizing reagents and stabilizers.

This invention also concerns to the specific amplification of genetic variant templates from the isolated genetic material described above. Only target genetic material that has a variation, e.g. single nucleotide polymorphism (SNP), gene deletion or insertion and/or translocation or truncation is amplified in a quantitative primer directed polymerase chain reaction (qPCR). This is achieved utilising xenonucleic acid (XNA) probe clamping sequences that have been designed to bind specifically by Watson-Crick base pairing to wild-type sequences in the sample. The presence of the XNA probes in the qPCR primer mix employed for the target amplification reaction causes inhibition of the polymerase mediated amplification of wild-type templates but does not impede the amplification of mutant template sequences.

The mechanism of the XNA clamping process is depicted in FIG. 1.

The suppression of wild-type (wt) template amplification and amplification of only mutant templates is achieved because there is a differential melting temperature (Tm) between the XNA clamp bound to mutant templates vs wt templates:

$$Tm(XNA \text{ mutant template}) \ll Tm(XNA \text{ wt template})$$

The Tm differential is as much as 15-20° C. for the XNA clamp probes. So that during the qPCR process only mutant templates are amplified.

The methods disclosed herein can be used in the detection of numerous allelic variants, including nonsense mutations, missense mutations, insertions, deletions, and the like. Owing to the advantageous sensitivity and specificity of detection afforded by the methods disclosed herein, the methods can detect the presence of a rare allelic variant within a sample, amongst a high wild-type background. Accordingly, although the skilled artisan will appreciate that the methods disclosed herein can be used in a variety of settings to detect, e.g., germline mutations, the methods are particularly well-suited for use in the detection of somatic mutations, such as mutations present in tumors. Non-limiting examples of rare, somatic mutations useful in the diagnosis, prognosis, and treatment of various tumors include, for example, mutations in ABL, AKT1, AKT2, ALK, APC, ATM, BRAF, CBL, CDH1, CDK 2A, CEBPA, CRLF2, CSF1R, CTNNB1, EGFR, ERBB2, EZH2, FBXW7, FGFR, FGFR2, FGFR3, FLT3, FOXL2, GATA1, GATA2, GNAQ, GNAS, HNF1A, HRAS, IDH1, IDH3, JAK2, KIT, KRAS, MEK1, MET, MPL, NF2, NOTCH 1, NOTCH2, NPM, NRAS, PC A3, PDGFRA, PIK3CA, PIK3R1, PIK3R5, PTCH1, PTEN, PTPN1 1, RBI, RET, RUNX1, SMAD4, SMARCB, SMO, STK11, TET2, P53, TSHR, VHL, WT1, and others. Exemplary mutant alleles associated with cancer useful in the embodiments disclosed herein include, but are not limited to those described in publications listed on the world wide web site for COSMIC (Catalogue Of Somatic Mutations In Cancer).

Next-generation sequencing (NGS) is widely used to detect sequence variations and an array of genetic markers for oncological diagnostic research and, in combination with bioinformatics, is increasingly used to analyze multiple biomarkers in a low-cost, time-effective manner[1]. However, one of the challenges in detecting cancer variants with standard NGS analysis is the low frequency of mutant alleles in cancer cells amongst a background of wild type alleles in healthy cells. The adequate resolution of low-frequency SNVs is essential both to improve treatment of cancer and to monitor minimal residue disease status during follow-up. However, typically NGS sensitivity is limited to variants at 0.1-1.0% mainly due to sequencing related background errors. In order to meet clinical standards and to distinguish true variants from sequencing errors, NGS has to be accurate and robust, several solutions have been described. For example, the application of proofreading enzymes (proofreading DNA-polymerase containing 3'-5' exonuclease activity) significantly increased NGS sensitivity by reducing false-positive variant calls at respective genomic positions. And the use of complex barcoding strategies, which enable the separation of true single nucleotide variants (SNVs) from errors. Deep sequencing is another solution to achieve the detection of variant with low frequency, however, deep sequencing increases the systematic error rate arise from sequencing machine and leads to unreliable result[2,3]. In some cases, deep sequencing is still not able to achieve the detection of hotspots covered by low performance primer set amongst large primers pool, which makes deep sequencing a pricy and inefficient method. Detecting the variant with low frequency is still challenging for most of the researcher in this area. In order to reliably distinguish true variants from sequencing-related errors at mutant allele frequencies of <0.1% and to identify suitable markers for cancer disease prognostic detection, A new technology that it enables to detect the "needle" from the "haystack" is needed to face the challenge.

Xenonucleic Acid (XNA) molecular clamp is an innovative nucleic acid molecular oligomers (FIG. 1a) that hybridize by Watson-Crick base pairing to target DNA sequences, which are used during polymerase chain reaction (PCR) to selectively suppress amplification of DNA with wild type alleles and amplify DNA containing mutant alleles (FIG. 1b). Mutants with low allelic frequency will be easily detectable without deep sequencing after enrichment by adding XNA in PCR[4,5,6] (FIG. 1b).

Herein, we introduce a highly sensitive OptiSeq™ Lung and Colorectal Cancer Dual Cancers Panel powered by the proprietary XNA technology to detect low frequency variants in human standard reference samples and lung or colorectal cancer patients' samples. This NGS diagnostic platform with XNA significantly improves the detection sensitivity of variants for diagnosis of cancer mutants even at ultra-low allele frequency.

Here we present results of XNAs mix enrichment effects on cell line genomic DNA samples with low variant allelic frequency, and lung and colorectal cancer patient samples, a benchmarking efforts aimed at enriching variant allelic frequency of samples with low frequency, and made low VAF samples detected by next generation sequencing method reliably and cost-efficiently, thus drawing conclusion confidently without sacrificing the quality of results. Meanwhile, regression models for 17 hotspots were constructed to get the relationship between enriched VAF and original VAF. In this way, original VAF value can be derived from enriched VAF by the corresponding equation, which provides an insight for clinical professionals to draw conclusion based on original VAF, particularly for variants with super low variant frequency, since typically NGS sensitivity is limited to variants at 0.1-1.0% mainly due to sequencing related background errors. Any variant allelic frequency below 1.0% will not be sufficient to draw reliable conclusion about the authenticity of mutations.

From the results of enrichment effects of XNAs mix on cell line genomic DNA samples, the mutant detection powered by the XNAs mix was dramatically boosted. 14 out of 17 hotspots were able to go down to the detection limit 0.10% with detected variant number more than 2. On samples originally with estimated 1.25% of mutants, in 14 of 17 hotspots, observed VAFs were more than 10% after XNA enrichment. This result suggested that XNA is able to enrich mutant alleles and make high confidence calls. The enrichment effects of 13 different XNAs varied based on the characteristics of each XNA. For XNA named EGFR G719, it shows a strong binding affinity towards the wild type and is able to enrich detected VAF up to 94.43% from 1.01%, which is 93.5 times more than the original VAF in the sample. However, for XNA like CTNNB1 S45, detected VAF after adding XNA was less than 1.0%, detected variant number was even less than 1 copy, which is not sufficient enough to draw the confident conclusion about the authenticity of mutant. It indicated that the binding affinity of XNA CTNNB1 S45 was weaker than that of EGFR 5719. It started to show detected variant on the condition of estimated original VAF 0.25% (Variant number was 2) with XNAs mix.

For some of the XNAs, they cover two loci at the same time. For example, NRAS A59 XNA covers two loci NRAS A59 and NRAS Q61, or NRAS G12 XNA covers two loci NRAS G12 and NRAS G13. Summary for covered hotspots by 13 XNAs was summarized in Table 11. Despite one XNA was used to block two loci, the blocking efficiency of XNA towards two loci was not directly related. For example, NRAS A59 XNA showed a good enrichment efficiency towards hotspot NRAS A59T, enriched VAF with XNA was 3.89 at original VAF 0.08, which is 48.6 times more than original VAF. While for hotspots NRAS Q61H, the enriched VAF was 0.16, which was only 3.2 folds than original VAF.

Enough sequencing coverage of each loci is necessary to achieve confident call of mutant, particularly for some mutants with super low frequency, in some rare cases, even pricy deep sequencing fails to detect them. From the results shown in Table 13-A and Table 13-B. The total sequencing coverage of samples with XNAs mix were less than those without XNAs mix. For example, average total coverage of estimated original VAF 0.10% with XNAs mix was 603, while that of same VAF without XNA WAS 2121. Despite the reduction of sequencing depth, enriched VAF for 14 out 17 hotspots were more than 1.00% to draw confident calls. While for same libraries without XNAs mix, only 1 out of 17 hotspots were more than 1.00%. Besides one important criterion "Enriched VAF", actual detected variant number was of same importance as well. Enough variant number ensures the authenticity of mutant call. The average variant number with XNAs mix was 9.1 times of those without XNAs mix. All these results demonstrated XNAs effects on the enrichment of detected VAF, which is of great significance to get reliable call from sequencing machine, since typically NGS sensitivity is limited to variants at 0.1-1.0% mainly due to sequencing related background and PCR errors. Meanwhile, sufficient number of variants were got due to the blocking effects on wild type background noise.

From results of Table 14, we learnt that the higher the original VAF, the lower CV %. The reason that lower VAF leads to higher CV % might due to the sampling issue of the DNA input. Since the real copies of mutant with VAF 0.10% are only 3 copies, which made it hard for experimental operator to pick up exact 3 copies from the stock solution, this sampling issue made a butterfly effect and caused the big variance of variant numbers and VAF in library, thus leading to the high CV %. As the VAF increases up to 1.25%, copies number of mutant was 42 copies, this sampling issue got weakened and high CV % 17.7 was achieved. The trend found in Table 14 was similar to that in Table 14 and it can be explained by sampling issue as well. Since as the original VAF increased, the positive predictive values (PPV) increased and reached 100% when estimated original VAF was 1.25%.

Although regression equations deduced by modeling can help to get the original VAF from enriched VAF with XNAs mix, it only applies when deduced original VAF value falls within confidence interval range (up to VAF 15%). It might applies when out of confidence interval, however, additional data are required to verify this assumption. For example, Lung cancer FFPE sample ID 16A140, original VAF of mutation EGFR L858R was 34.31%, detected enriched VAF for this mutation was 83.76%. If we applied regression equation, calculated VAF was 134.05%, which is beyond 100% and greatly off the true value 83.76%. While for FFPE sample ID 16A011, original VAF of mutation EGFR L858R was 20.37%, despite off of confidence interval limit 12.4%, calculated enriched VAF was 97.81% which is approximately close to detected enriched 91.91%. we acknowledged that It would be better and more comprehensive of this study to get the full regression model from original VAF 0.00% to 100.00% for each hotspots, however, in this study, we only focus on the XNAs enrichment effects on mutations with super low or low variant frequency help detect existed low variant frequency mutations with more cost-efficient method. For original VAF more than 15.0%, it can be detected confidently with normal NGS method.

In summary, XNA molecular clamp technology in combination with NGS have a great potential for cancer molecular diagnosis of cancer mutations in ultra-low allele frequency. OptiSeq™ Lung and Colorectal Cancer Mini Panel powered by XNAs is able to report mutants from 10 ng of input gDNA with allele frequency as low as 0.10% with confident calls for 14 out of 17 hotspots. The relationship between enriched VAF and original VAF were derived using regression model for 17 hotspots. Some of regression equations were verified using clinical patient samples and proved reliable to deduce original VAF from enriched VAF. Significant progress has been made in characterizing and optimizing the use of XNA in conjunction with OptiSeq™ oncology NGS panel, which provides a promising solution to detect mutants with low frequency with improvement sensitivity and confidence. Clinical sensitivity for FFPE is about 100% for lung cancer (14/14 samples) and colorectal cancer samples (10/10 samples), comparing to normal NGS about 85.7% (12/14 lung sample) and 70% (7/10) for colon cancer. For cfDNA its clinical sensitivity is about 100% for lung (10/10) and colon cancer (2/2), but normal NGS is about 70% for lung (3/10) and 0% for colon cancer (0/2 sample)

EXAMPLES

Example 1

The kit described in great detail in this Example is a KRAS mutation detection kit. However, the same type of kit may be assembled to detect mutations in NRAS, EGFR, BRAF, PIK3CA, JAK2, as well as other genes of importance in precision molecular diagnostics.

QCLAMP™ Technology for Mutation Detection

The QCLAMP™ KRAS Mutation Detection Kit is based on xenonucleic acid (XNA) mediated PCR clamping technology. XNA is a synthetic DNA analog in which the phosphodiester backbone has been replaced by a repeat formed by units of (2-aminoethyl)-glycine. XNAs hybridize tightly to complementary DNA target sequences only if the sequence is a complete match. Binding of XNA to its target sequence blocks strand elongation by DNA polymerase. When there is a mutation in the target site, and therefore a mismatch, the XNA:DNA duplex is unstable, allowing strand elongation by DNA polymerase. Addition of an XNA, whose sequence with a complete match to wild-type DNA, to a PCR reaction, blocks amplification of wild-type DNA allowing selective amplification of mutant DNA. XNA oligomers are not recognized by DNA polymerases and cannot be utilized as primers in subsequent real-time PCR reactions.

DNA Isolation

Human genomic DNA must be extracted from tissue or blood, or fixed paraffin-embedded tissue prior to use. Several methods exist for DNA isolation. For consistency, we recommend using a commercial kit, such as Qiagen DNA extraction kit (QIAamp DNA FFPE Tissue Kit, cat No. 56404, for paraffin embedded specimens; DNeasy Blood & Tissue kit, cat. No. 69504 or 69506, for tissue and blood specimens). Follow the genomic DNA isolation procedure according to manufacturer's protocol. Sufficient amounts of DNA can be isolated from FFPE blocks or fresh frozen sections (approx. 2-10 µg).

This QCLAMP™ assay requires a total of 30-60 ng of DNA per sample (5-10 ng/reaction). After DNA isolation, measure the concentration using spectrophotometric analysis (i.e. Nanodrop or UV spectrophotometer) and dilute to it to 1.25-2.5 ng/µl. Make sure A260/A230 value is greater than 2.0 and A260/A280 value between 1.8 and 2.0.

Preparation of Reagents

Each kit contains enough material to run 3 sets (10-sample test kit) or 6 sets (30-sample test kit) of Clamping Controls, Positive Controls and Non-Template Controls. Thaw all Primers, XNAs, Positive Control, WT Clamping Control, water and 2×PCR Mastermix provided. Thaw all reaction mixes at room temperature for a minimum of 1 hour. Vortex all components except the PCR Master Mix the reaction mixes for 5 sec and perform a quick spin. The PCR Master Mix should be mixed gently by inverting the tube a few times. Do not leave kit components at room temperature for more than 4 hours. After thawing, keep materials on ice at all times. The PCR reactions are set up in a total volume of 20 µl/reaction.

Table 1 shows the component volumes for each 20ul reaction.

TABLE 1

QCLAMP ™ Assay Components and Reaction Volume

| Components | Volume/Reaction |
|---|---|
| 2X PCR Master mix | 10 µl |
| Primer Mix | 4 µl |
| XNA | 2 µl |
| DNA sample or Controls | 4 µl |
| Total volume | 20 µl |

For accuracy, 2×PCR Master mix, primers and XNA should be pre-mixed into assay mixes as described in Table 2 below.

Preparation of Assay Mixes

IMPORTANT: Assay mixes should be prepared just prior to use. Do not store assay mixes. Prepare and keep assay mixes on ice, until ready for per. Label 7 micro centrifuge tubes (not provided) according to each corresponding reaction mix shown in Table 2.

TABLE 2

Preparation of Assay Mixes

| | Volume of 2X PCR Master Mix | Volume of Primer Mix | Volume of XNA (†use water for ext control) |
|---|---|---|---|
| Ext Control Mix | 10 µl × (*n + 1) | 4 µl × (*n + 1) | 2 µl × (*n + 1) |
| G12 Mix | 10 µl × (*n + 1) | 4 µl × (*n + 1) | 2 µl × (*n + 1) |
| G13 Mix | 10 µl × (*n + 1) | 4 µl × (*n + 1) | 2 µl × (*n + 1) |
| A59 Mix | 10 µl × (*n + 1) | 4 µl × (*n + 1) | 2 µl × (*n + 1) |
| Q61 Mix | 10 µl × (*n + 1) | 4 µl × (*n + 1) | 2 µl × (*n + 1) |
| K117 Mix | 10 µl × (*n + 1) | 4 µl × (*n + 1) | 2 µl × (*n + 1) |
| A146 Mix | 10 µl × (*n + 1) | 4 µl × (*n + 1) | 2 µl × (*n + 1) |

*n = number of reactions (DNA samples plus 3 controls). Prepare enough for 1 extra sample (n + 1) to allow for sufficient overage for the PCR set.
†Use 2 ul of water provided in the kit as the Ext Control Mix does not require XNA. For accuracy, do not pipette less than 10 ul of the XNA.

Prepare sufficient working assay mixes for the DNA samples, one KRAS Mixed Positive Control, one Nuclease-Free Water for no template control, and one WT Clamping Control, according to the volumes in Table 2. Include reagents for 1 extra sample to allow sufficient overage for the PCR set up. The master mixes contain all of the components needed for PCR except the sample.

Each sample requires one reaction for each mutation site detected by the kit and an external control. The External Control uses Exon 5 primers to determine if an appropriate level of amplifiable DNA is present in the sample, and ensures that that the supplied primers and polymerase are working properly on the sample. The KRAS Codon-Specific kit requires a total of 7 reactions for each sample.

A set of clamping controls must be run with each of the 7 reaction mixes, every time the assay is run. Clamping Controls use wild-type DNA as the template. Wild-type DNA should have no mutations, therefore the XNA probes will bind strongly, blocking the polymerase from making amplicons. However, the External Control Mix with the Clamping Control should make amplicons efficiently, providing another way to monitor performance of the primers, polymerase, and sample.

A set of positive controls must also be run with each of the 7 reaction mixes, every time the assay is run. The Positive Control contains one mutant template for each reaction mix. Positive controls contain mutations; therefore XNA probes will not bind, allowing amplification of the mutant template. Positive controls must show the appropriate values for the reaction to be valid.

A set of no template control (tube NTC) is run with each of the 7 reaction mixes every time the assay is run. Nuclease-Free Water is used in the place of template. The NTC serves as a negative control and assesses potential contamination during assay set-up.

Further quantities of KRAS Wild-Type Genomic Reference DNA Control, and Positive Control mixes can be purchased as a separate item, if desired.

Suggested Run Layout (96-Well Plate, Tube Strips, or Tubes)

Gently vortex the assay mixes for 5 sec and do a quick spin. Add 16 µl of the appropriate assay mix to the plate or tubes. Add 4 µl of template. Prepare and keep on ice until ready for PCR.

In the case of 96-well plates, the exact plate layout can be set to the user's preference. However, take care to remember which wells are for which reaction mixes, to ensure that all potential detected mutations and controls are processed properly. Table 3 is a suggested plate set-up for a single experiment analyzing 3 unknown samples.

TABLE 3

Suggested Plate Layout

|   | 1 | 2 | 3 | 4 | 5 | 6 |
|---|---|---|---|---|---|---|
| A | NTC Ext Ctrl Mix | PC Ext Ctrl Mix | CC Ext Ctrl Mix | S1 Ext Ctrl Mix | S2 Ext Ctrl Mix | S3 Ext Ctrl Mix |
| B | NTC G12 Mix | PC G12 Mix | CC G12 Mix | S1 G12 Mix | S2 G12 Mix | S3 G12 Mix |
| C | NTC G13 Mix | PC G13 Mix | CC G13 Mix | S1 G13 Mix | S2 G13 Mix | S3 G13 Mix |
| D | NTC A59 Mix | PC A59 Mix | CC A59 Mix | S1 A59 Mix | S2 A59 Mix | S3 A59 Mix |
| E | NTC Q61 Mix | PC Q61 Mix | CC Q61 Mix | S1 Q61 Mix | S2 Q61 Mix | S3 Q61 Mix |
| F | NTC K117 Mix | PC K117 Mix | CC K117 Mix | S1 K117 Mix | S2 K117 Mix | S3 K117 Mix |
| G | NTC A146 Mix | PC A146 Mix | CC A146 Mix | S1 A146 Mix | S2 A146 Mix | S3 A146 Mix |

PC: Positive Control,
NTC: No Template Control (water),
CC: Clamping Control (Wild-type DNA),
S1-3: Samples 1-3.
NOTE:
For setup on the Rotor-Gene Q Platforms, the layout must be changed such that the first well contains Positive Control.

When all reagents have been loaded, tightly close the PCR tubes or seal the 96-well plate to prevent evaporation. Spin at 2000 rpm for 1 minute to collect all the reagents. Place in the real-time PCR instrument immediately or store on ice until the instrument is ready.

Instrument Set-Up
Roche LightCycler 96 or RocheLightCycler 480
1. Select New empty experiment >create
2. In the Run Editor>Measurement, choose SYBR Green 1 (470/514) channel on (LC96), SYBR Green 1/HRM Dye on (LC480)
3. Set up run profile using parameters in Table 7. Ramp rates for the LC 96 and LC480 should match settings below.
4. During the analysis set threshold to Auto.

6. Click on Plate Setup in the left navigation panel 7. Select the Assign Targets and Samples tab and assign samples to the wells
8. Select NONE for the Passive Reference Dye
9. Click on Run Method on the left panel, set reaction volume to 20ul
10. Setup the cycling parameters as shown in the table below
11. Add Melt Curve at the end of the Cycling Stage. Use continuous and leave default setting for data collection
12. During the analysis set threshold to 0.5 (ABI 7900) and 5000 (ABI 7500).

TABLE 4

Roche Light Cycler, LC96 and LC480 Parameters

| Step | Temperature (° C.) | Time (Seconds) | Cycles | Ramp Rate | Mode | Acquisition Mode |
|---|---|---|---|---|---|---|
| PreIncubation | 95 | 300 | 1 | 4.4 | | None |
| Denaturation | 95 | 20 | X40 | 2.2 | Standard | None |
| XNA Annealing | 70 | 40 | | 2.2 | | None |
| Primer Annealing | 64 | 30 | | 2.2 | | None |
| Extension | 72 | 30 | | 1.0 | | Single |
| Melting | 95 | 10 | 1 | 4.4 | | None |
| | 65 | 60 | | 2.2 | | None |
| | 97 | 1 | | 0.20 | | Continuous (5 readings/° C.) |
| Cooling | 37 | 30 | 1 | 2.2 | | None |

*An HRM curve or melt analysis should be run at the end of the PCR reaction. This helps to verify the PCR amplification results and with troubleshooting.

Applied Biosystems Platforms

1. Select File>New Experiment
2. Enter an experiment name and select 7500 (96 wells) or as appropriate
3. Select Quantitation—Standard Curve
4. Select SYBR Green Reagents
5. Select Standard Ramp Rate if available

TABLE 5

Applied Biosystems Platforms Cycling Parameters

| Step | Temperature (° C.) | Time (Seconds) | Cycles | Data Collection |
|---|---|---|---|---|
| PreIncubation | 95 | 300 | 1 | OFF |
| Denaturation | 95 | 20 | X40 | OFF |
| XNA Annealing | 70 | 40 | | OFF |

TABLE 5-continued

Applied Biosystems Platforms Cycling Parameters

| Step | Temperature (° C.) | Time (Seconds) | Cycles | Data Collection |
|---|---|---|---|---|
| Primer Annealing | 66 | 30 | | OFF |
| Extension | 72 | 30 | | ON |
| Melt Curve | Default | | | Continuous |

Rotor-Gene Q Platforms
In the instrument software version 2.1 and above
1. Select File>New, Select Three Step with Melt and click New
2. Select 72-Well Rotor, check the Locking Ring Attached box, click Next
3. Set Reaction volume to 20ul, click next
4. Set Temperature profile as shown in Table 6.
5. Channel Setup: Select Green Source 470 nm, Detector 510 nm, Gain 7
a. Click Gain Optimization
b. Set Temperature to 70 C
c. Perform Optimization before 1st acquisition
d. Click optimize acquiring
e. In the pop-up box enter
i. Target Sample Range 5FL up to 10FL
ii. Acceptable Gain Range −10 to 10
f. Click OK, Click Close, Click Next
6. Start-run
7. During the analysis set threshold to Auto.

TABLE 6

Rotor-Gene Q Platforms Cycling Parameters

| Hold | | 95° C. | 5 minutes | X1 | Not Acquiring |
|---|---|---|---|---|---|
| Cycling | Timed Step | 95° C. | 20 seconds | X40 | Not Acquiring |
| | Timed Step | 70° C. | 40 seconds | | Not Acquiring |
| | Timed Step | 64° C. | 30 seconds | | Not Acquiring |
| | Timed Step | 72° C. | 40 seconds | | Acquiring to Cycling A on Green |
| Melt | | | Ramp from 65 to 95, rising by 1degree each step | | Acquire to melt A on green |
| | | | Wait for 90 sec of pre-melt conditioning on first step | | |
| | | | Wait for 5 seconds for each step afterwards Gain Optimization | | |
| | | | Check optimize gain before melt on all tubes | | |
| | | | The gain giving the highest fluorescence less than 95 will be selected. | | |

Assessment of Real-Time PCR Results

For the analysis use Absolute Quantitation, automatic baseline. The threshold to be used with each instrument is listed above. Check threshold to ensure that the Threshold is within the exponential growth phase of the amplification plot. If not, the threshold maybe adjusted depending on the run.

The real-time PCR instrument generates a Cq value. Cq is the cycle threshold, the cycle number at which a signal is detected above background fluorescence. The lower the cycle number at which signal rises above background, the stronger the PCR reaction it represents No Template Controls Verify that there is no amplification in no-template controls for each of the reaction mixes. Cq should be undetermined. For some mixes a Cq of 36 or higher may be observed in the NTC. In such cases, check the melting curves obtained. If the melting curve indicates the presence of primer dimers, the reaction may be acceptable. SYBR green binds to primer dimers, resulting in a peak with a lower melting temperature, than the desired amplicon. In many cases formation of primer dimers can be avoided by setting up the PCR reactions on ice, until ready to load into the PCR instrument.

Analysis of Clamping and Positive Controls

The Cq values of the Positive Control (mixed mutant templates) should amplify in the presence of XNAs and yield Cq values given in Table 7.

TABLE 7

Acceptable Cq Ranges for Positive Controls

| | Positive Control Acceptable Cq Range |
|---|---|
| Ext Control | 20 ≤ Cq ≤ 26 |
| G12 Mix | ≤32 |
| G13 Mix | ≤32 |
| A59 Mix | ≤32 |
| Q61 Mix | ≤30 |
| K117 Mix | ≤34 |
| A146 Mix | ≤30 |

The Cq value of the Clamping Control (WT DNA) with the Ext Control Mix should be within 20 and 26.
In addition, the Cq of the Clamping Control with each of the mutation reaction mixes should be at least 3 Cq greater than the Cq of Positive Control with the same reaction mix. If these criteria are not met, the reaction has failed and the results are not valid.

PASS: Cq of Clamping Control with mutation reaction mix−Cq of Positive Control with same mutation reaction mix ≥3

FAIL: Cq of Clamping Control with mutation reaction mix−Cq of Positive Control with same mutation reaction mix ≤3

Judging Validity of Sample Data Based on External Control Mix Results

The Cq value of the Ext Control Mix can serve as an indication of the purity and the concentration of DNA. Thus, the validity of the test can be decided by the Cq value of the Ext Control Mix. Cq values of any sample with Ext Control Mix should be in the range of 20-27. If the Cq values fall outside the range given in Table 8, the test results should be considered invalid. The experiment should be repeated.

TABLE 8

Acceptable Cq Ranges for Samples with External Control Mix

| Validity | Cq Value of Ext Control Mix | Descriptions and Recommendations |
|---|---|---|
| Optimal | 20 < Cq < 27 | The amplification and amount of DNA sample were optimal. |
| Invalid | Cq ≤20 | Possibility of a false positive is high. Repeat the PCR reaction with less DNA. |
| Invalid | Cq ≥27 | Not enough DNA or DNA not pure. The amplification is not optimal. Check DNA amount and purity. Repeat the experiment |

Scoring Mutational Status
IMPORTANT: Refer to the Macro Sheet for QCLAMP™ Cq Mutation Analysis for scoring mutational status. Macro maybe requested by contacting information@diacarta.com
If a Cq value is undetermined, assign a Cq of 40 and proceed to analysis.
The table below should be used to determine mutational status

TABLE 9

Scoring Mutational Status

| Mutation | | G12 | G13 | A59 | Q61 | K117 | A146 |
|---|---|---|---|---|---|---|---|
| Strong Positive: Mutation Content >5% | Cq | ≤32 | ≤32 | ≤32 | ≤30 | ≤33 | ≤30 |
| Weak Positive: | Cq | 32-35* | 32-35* | 30-35* | 30-35* | 33-35* | 30-35* |
| Mutation Content 1-5% | ΔCq | ≤10 | ≤9 | ≤8 | ≤8 | ≤10 | ≤8 |
| Negative | Cq | ≥35 | ≥35 | ≤30 | ≥35 | ≥35 | ≥35 |

*If reaction has been set-up with 5 ng of DNA, it is recommended that the experiment be repeated with 10 ng of template DNA to confirm the results.
*Refer to Table 9 for interpretation of A59/Q61 Mutational Status If the Cq value suggests mutation content between 1%-5%, a further calculation of ΔCq should be performed to determine mutational status.
ΔCq=[Cq value of sample with mutant reaction mix]−[Cq value of sample with Ext Control Mix]
For ex: ΔCq=[Cq of sample with G12 mutant reaction mix]−[Cq of sample with Ext Control Mix]
Refer to the table above to confirm mutational status of weak positives.
Differentiating A59/Q61 Mutational Status
The Q61 reaction mix detects both A59 and Q61 mutations, whereas the A59 reaction mix detects only A59 mutations. Therefore, in order to differentiate between A59 and Q61 Mutations a combination of results from the 2 mixes should be used, as described in Table 10 below.

TABLE 10

Interpretation of A59/Q61 Mutational Status

| Reaction Mix | Result Based on Table 12 | Mutational Status |
|---|---|---|
| A59 Reaction Mix | Positive | A59 Mutation |
| Q61 Reaction Mix | Positive | |
| A59 Reaction Mix | Negative | Q61 Mutation |
| Q61 Reaction Mix | Positive | |
| A59 Reaction Mix | Negative | Q61 Mutation |
| Q61 Reaction Mix | Positive | |

HRM Curves as a Tool to Confirm Analyses
In High Resolution Melting Analysis (HRM), the region of interest amplified by PCR is gradually melted. SYBR green is a dsDNA binding dye that is released as the dsDNA amplicon is melted. Emitted fluorescence is measured to generate a characteristic curve. The Tm (Melting Temperature) is characteristic of the GC content, length and sequence of a DNA product and is a useful tool in product identification. The resulting melt profile reflects the mix of amplicons present.

Wild-type DNA (clamping control) is provided. Some amplification may occur in these reactions. Melt profiles of unknown samples should be compared to wild-type and positive controls. Enrichment of one or more peaks, resulting in a melt profile distinct from wild-type DNA profile, can serve as an indication of specific amplification of a mutation target. If the melt profile of an unknown sample is similar to wild-type DNA, and has been scored as a mutation due to Cq, the analysis should be repeated. The resulting PCR product can be sent for Sanger sequencing for further clarification.

HRM curves obtained from unknown samples can be compared to HRM curves obtained from positive controls. Amplicons of similar length and sequence will exhibit the same melt profile.

Example 2

PCR based enrichment of mutant DNA template sequences from template DNA derived from a lung cancer tumor biopsy sample is shown below using a xeno-nucleic acid clamping probe specific for KRAS Exon 2 codon 12. Only codon 12 mutant sequences are amplified as shown by the melting profile of the PCR amplicons generated before enrichment and after XNA clamped PCR enrichment:

The PCR product from the XNA clamped mutant enriched PCR reaction can be isolated and used directly in a Sanger sequencing or Pyrosequencing reaction or else it can be processed for next generation sequencing (NGS) by ligation of adapters and after removal of excess adapters can be used directly for NGS without the need for another PCR amplification step.

Example 3

Figure 3:
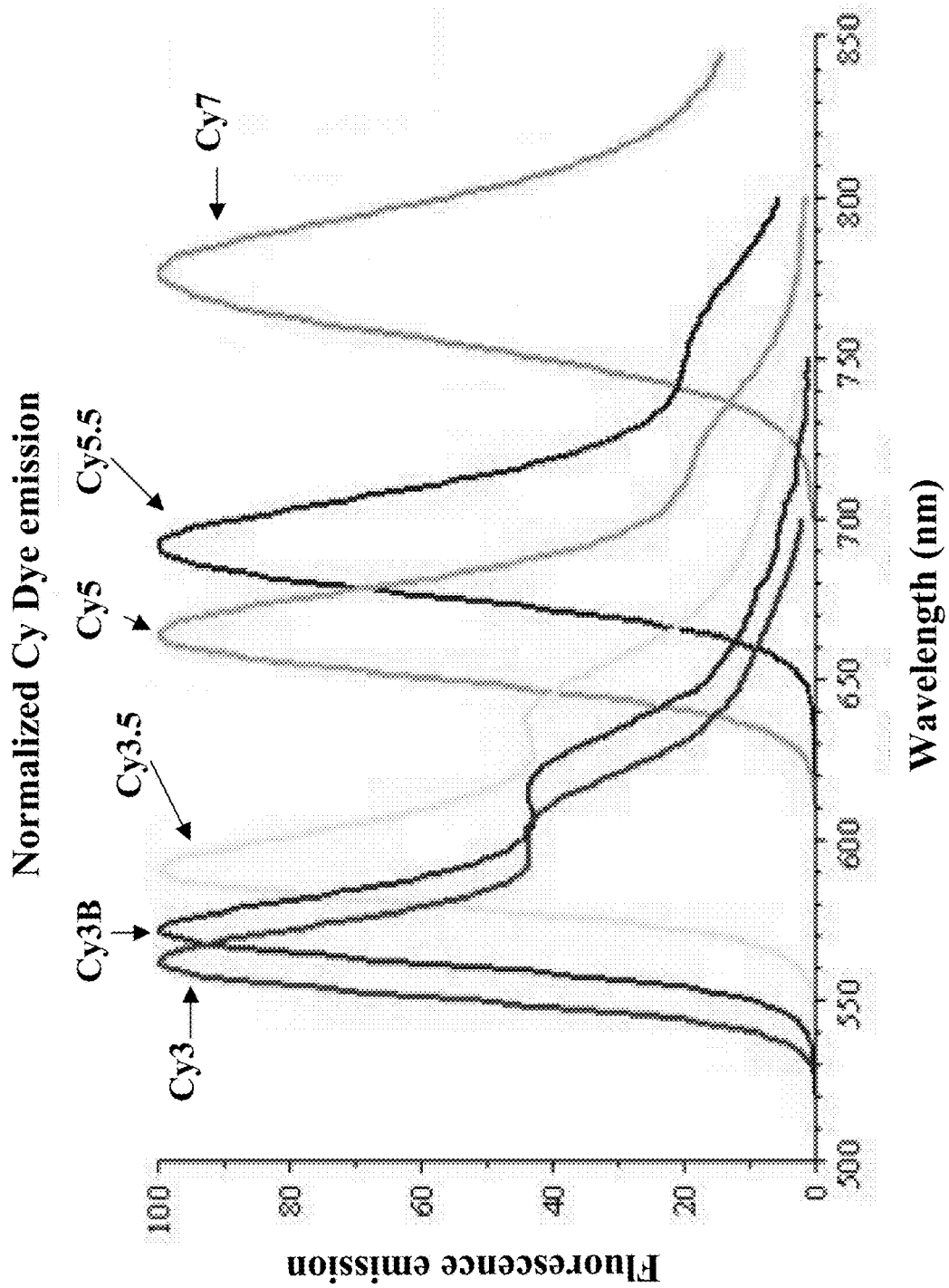
FIG. 3 show specific hydrolysis probe having a different fluorophore (and quencher) selected from the available fluorophores for multiplex applications.

Multiplex Detection of KRAS Mutations.
In this example of this invention, locus specific hydrolysis probes are designed to detect mutant amplicons in the KRAS proto-oncogene. Locus specific probes are designed for the following mutant amplicons in KRAS:
Probe 1 KRAS Exon 2 codon 12,
Probe 2 KRAS Exon 2 codon 13,
Probe 3 KRAS Exon 3 codon 59
Probe 4 KRAS Exon3 codon 61,
Probe 5 KRAS Exon 4 codon 117,
Probe 6 KRAS Exon 4 codon 146
and a control probe for a coding sequence in KRAS that has no mutations—Probe 7 KRAS Control probe Each locus specific hydrolysis probe has a different fluorophore (and quencher) selected from the available fluorophores for multiplex applications (see FIGS. 3 and 4).

Figure 5:
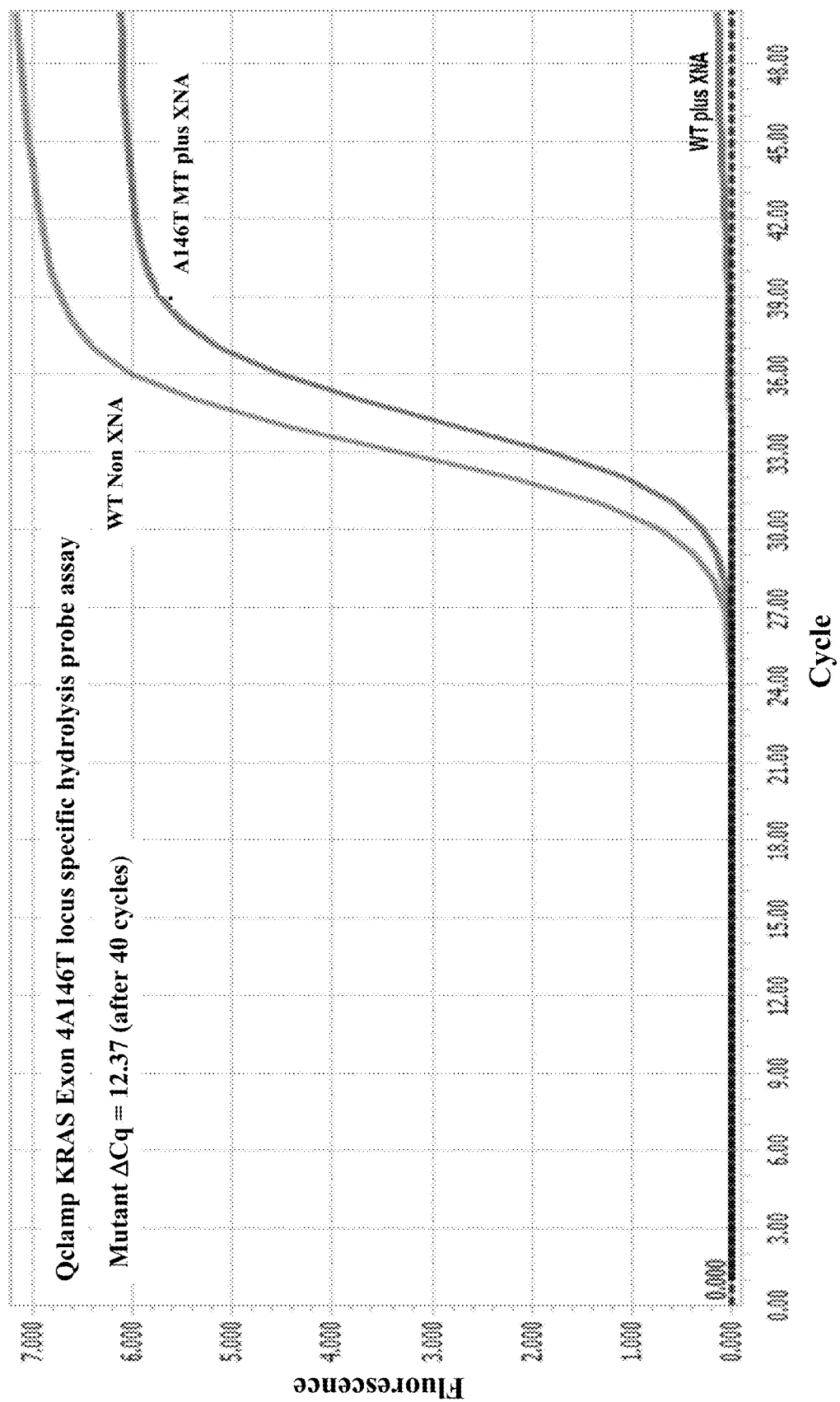
FIG. 5 shows a specific locus specific hydrolysis probe assay.

For the KRAS multiplex assay, KRAS c12, c59, c117 and c146 and KRAS control are detected in a one tube and KRAS c13 and c61 and KRAS control in a separate tube. So that all mutations in the KRAS proto-oncogene can be detected using only 2 PCR reaction tubes. FIG. 5 is an Example of the Exon 4 locus specific probes assay.

Example 4

This example of the invention describes the use of mutation specific capture probes covalently attached to optically bar-coded beads via an amino-linker spacer. Mutant specific probes and control probes for the detection of mutations in KRAS Exon 2 codons 12 and 13 are shown below:

| | | | |
|---|---|---|---|
| 1. | G12A | SEQ ID NO: 1 | AGCTG<u>C</u>TGGCGTA |
| 2. | G12R | SEQ ID NO: 2 | AGCTC<u>C</u>GTGGCGTA |
| 3. | G12D | SEQ ID NO: 3 | AGCTG<u>A</u>TGGCGTA |
| 4. | G12C | SEQ ID NO: 4 | AGCT<u>T</u>GTGGCGTA |
| 5. | G12I | SEQ ID NO: 5 | GAGCT<u>AT</u>TGGCGT |
| 6. | G12L | SEQ ID NO: 6 | GAGCT<u>CT</u>TGGCGT |
| 7. | G12S | SEQ ID NO: 7 | AGCT<u>A</u>GTGGCGTA |
| 8. | G12V | SEQ ID NO: 8 | AGCTG<u>T</u>TGGCGTA |
| 9. | G13C | SEQ ID NO: 9 | TGGT<u>T</u>GCGTAGGC |
| 10. | G13D | SEQ ID NO: 10 | TGGTG<u>A</u>CGTAGGC |
| 11. | G13A | SEQ ID NO: 11 | TGGTG<u>C</u>CGTAGGC |
| 12. | G13V | SEQ ID NO: 12 | TGGTG<u>T</u>CGTAGGC |
| 13. | G13S | SEQ ID NO: 13 | TGGT<u>A</u>GCGTAGGC |
| 14. | G13R | SEQ ID NO: 14 | TGGT<u>C</u>GCGTAGGC |

The control Capture Probes are:

| | | | |
|---|---|---|---|
| 15. | (HLA-)DRA Match | SEQ ID NO: 15 | GGAGACGGTCTGG |
| 16. | (HLA-)DRA Mismatch | SEQ ID NO: 16 | GGAGACG<u>C</u>TCTGG |
| 17. | KRAS Wild type: | SEQ ID NO: 17 | CT<u>GGTGGC</u>GTAGG |
| 18. | KRAS PCR control | SEQ ID NO: 18 | AAGGCCTGCTGAA |

All probes contain a 5'-amino-linker for bar-coded bead conjugation. After, performing XNA clamping PCR reaction is done to eliminate wild-type KRAS using the following primers: KRAS Exon 2 Forward: SEQ ID NO: 19 5'-GTACTGGTGGAGTATTTGATAGTG-3' KRAS Exon 2 Reverse: SEQ ID NO: 20 5'-ATCGT-CAAGGCACTCTTGCCTAC-3' and XNA Clamp Probe Blocker specific for KRAS Exon 2 12/13 optically bar-coded mutation specific capture beads are added and incubated for hybridization capture. After washing detection is performed with Streptavidin Phycoerythrin (SAPE) and measured on DigiPlex analyzer.

Example 5

QCLAMP™ Sample DNA Preparation Protocol

Genomic DNA should be obtained either from whole blood, cells, purified peripheral blood lymphocytes of whole blood, polynuclear cells, or granulocytes, tissue biopsies or FFPE sections. For comparable results it is recommended that the same cellular fraction and DNA extraction method are used. DNA extraction can be performed using a home-brew method or a commercially available kit.

Carefully transfer FFPE section(s) or equivalent amount of fresh tissue, cells (100 to 100,000 cells) or 200 μl whole blood to a clean 1.7 ml polypropylene micro-centrifuge tube and add the required volume of lysis solution. For FFPE sections add 50 μL of lysis Solution. For liquid or moist cells or tissues add 2× volume of the sample volume.

For FFPE samples warm each sample in heating block at 95° C. until paraffin melts and then vortex each warm sample for 10 seconds. Return the sealed sample preparation tubes to the heating block and heat at 95° C. for 20 minutes make sure to carefully remove the tubes every 5 min and vortex each tube for 10 s and return to heating block.

Remove sample preparation tube from heating block and immediately add an equivalent volume of lysis solution as the volume added of lysis solution from step 1 above. For example, if 50 μL of lysis solution was added, add 50 μL of lysis solution.

Vortex each sample for 10 seconds. Spin down the sample preparation tubes in a microcentrifuge and allow to cool. Use the resultant lysis solution lysate supernatant directly in the PCR reaction.

The extracted DNA needs to be diluted to a concentration of 5 ng/μl in 1× TE buffer at pH 8.0 and then stored at +4 to +8° C. for 1 week or at −20° C. if longer term storage is required. The QCLAMP™ qPCR reaction is optimized for DNA samples containing 5-20 ng of purified genomic DNA.

The sequences in the Table below show exemplary primers and xenonucleic acids (XNA's).

| Sequence Name | | |
|---|---|---|
| 1047SSF001NEW | SEQ ID NO: 21 | CGAAAGACCCTAGCCTTAGATAAAACT |
| 1047SSR0012NEW | SEQ ID NO: 22 | ATTGTGTGGAAGATCCAATCCATTT |
| 146R002f | SEQ ID NO: 23 | ACGTTGGATGTGTACCATACCTGTCTGGTCTT |
| 21FW1S | SEQ ID NO: 24 | GTTTTCCCAGTCACGACACGTTGGATGCAGCCAGGAACGTACTGGTGA |
| BIOBRAFCONTRLFP | SEQ ID NO: 25 | /5Biosg/CTCCAGATCTCAGTAAGGTACGG |
| BIOKRASCONTRLFP | SEQ ID NO: 26 | /5Biosg/TGAGGGAGATCCGACAATACAG |

-continued

| Sequence Name | | |
|---|---|---|
| BRAFAZFPNEW02 | SEQ ID NO: 27 | ACAGTAAAAATAGGTGATTTTGGTCTAGCTA |
| BRAFAZFPNew02s | SEQ ID NO: 28 | GTTTTCCCAGTCACGACACGTTGGATGACAGTAAAAATA GGTGATTTTGGTCTAGCTA |
| BRAFAZRP001 | SEQ ID NO: 29 | CATCCACAAAATGGATCCAGACAA |
| BRAFAZRP001s | SEQ ID NO: 30 | CAGGAAACAGCTATGACACGTTGGATGCATCCACAAAAT GGATCCAGACAA |
| BRAFCONTRLFP | SEQ ID NO: 31 | CTCCAGATCTCAGTAAGGTACGG |
| BRAFCONTRLRP | SEQ ID NO: 32 | GGGAAAGAGTGGTCTCTCATC |
| C790F002f | SEQ ID NO: 33 | ACGTTGGATGTCCACCGTGCAGCTCATC |
| C790F002fS | SEQ ID NO: 34 | GTTTTCCCAGTCACGACACGTTGGATGTCCACCGTGCAG CT |
| C790R001Bf | SEQ ID NO: 35 | ACGTTGGATGGTCTTTGTGTTCCCGGACAT |
| C790R001BfS | SEQ ID NO: 36 | CAGGAAACAGCTATGACACGTTGGATGGTCTTTGTGTTC CC |
| Ex19NewFS | SEQ ID NO: 37 | GTTTTCCCAGTCACGACACGTTGGATGCTCTCTGTCATA GGGACTCTGGATCC |
| Ex19NewFwd | SEQ ID NO: 38 | CTCTCTGTCATAGGGACTCTGGATCC |
| Ex19NewRev | SEQ ID NO: 39 | AGCAAAGCAGAAACTCACATCGAG |
| Ex19NewRS | SEQ ID NO: 40 | CAGGAAACAGCTATGACACGTTGGATGAGCAAAGCAGAA ACTCACATCGAG |
| Exon18NewFS | SEQ ID NO: 41 | GTTTTCCCAGTCACGACACGTTGGATGGCTCCCAACCAA GCTCTCTTGA |
| Exon18NewFwd | SEQ ID NO: 42 | GCTCCCAACCAAGCTCTCTTGA |
| Exon18NewRev | SEQ ID NO: 43 | CTGTGCCAGGGACCTTACCTTATAC |
| Exon18NewRS | SEQ ID NO: 44 | CAGGAAACAGCTATGACACGTTGGATGCTGTGCCAGGGA CCTTACCTTATAC |
| Exon2FowardNew | SEQ ID NO: 45 | TTTGCCAAGGCACGAGTAACAAG |
| Exon2ReverseNew | SEQ ID NO: 46 | CCCAAGGACCACCTCACAGTTAT |
| JAK2XN9F001 | SEQ ID NO: 47 | TTAACTGCAGATGCACATCATTACCT |
| KRAS117F002 | SEQ ID NO: 48 | GGACTCTGAAGATGTACCTATGG |
| KRAS117F002s | SEQ ID NO: 49 | GTTTTCCCAGTCACGACACGTTGGATGGGACTCTGAAGA TGTACCTATGG |
| KRAS117R002 | SEQ ID NO: 50 | GCTAAGTCCTGAGCCTGTTT |
| KRAS117R002s | SEQ ID NO: 51 | CAGGAAACAGCTATGACACGTTGGATGGCTAAGTCCTGA GCCTGTTT |
| KRAS146F003 | SEQ ID NO: 52 | ACACAAAACAGGCTCAGGAC |
| KRAS146F003s | SEQ ID NO: 53 | GTTTTCCCAGTCACGACACGTTGGATGACACAAAACAGG CTCAGGAC |
| KRAS146R002 | SEQ ID NO: 54 | CAGTGTTACTTACCTGTCTTGTCTT |
| KRAS146R002s | SEQ ID NO: 55 | CAGGAAACAGCTATGACACGTTGGATGCAGTGTTACTTA CCTGTCTTGTCTT |
| KRASBIOFP002 | SEQ ID NO: 56 | AAGGCCTGCTGAAAATGACTG |
| KRASBioFP002s | SEQ ID NO: 57 | GTTTTCCCAGTCACGACACGTTGGATGAAGGCCTGCTGA AAATGACTG |
| KRASC12RP002s | SEQ ID NO: 58 | CAGGAAACAGCTATGACACGTTGGATGTCAAGGCACTCT TGCCTACGC |

-continued

| Sequence Name | | |
|---|---|---|
| KRASc13F001 | SEQ ID NO: 59 | ACTTGTGGTAGTTGGAGCTGGT |
| KRASC13F001s | SEQ ID NO: 60 | GTTTTCCCAGTCACGACACGTTGGATGACTTGTGGTAGT TGGAGCTGGT |
| KRASC13NEWR001 | SEQ ID NO: 61 | TCATGAAAATGGTCAGAGAAACCTT |
| KRASC13NewR001s | SEQ ID NO: 62 | CAGGAAACAGCTATGACACGTTGGATGACTTGTGGTAGT TGGAGCTGGT |
| KRASC59R001 | SEQ ID NO: 63 | ATTGCACTGTACTCCTCTTGACC |
| KRASC59R001s | SEQ ID NO: 64 | CAGGAAACAGCTATGACACGTTGGATGATTGCACTGTAC TCCTCTTGACC |
| KRASc61F001 | SEQ ID NO: 65 | CTCTTGGATATTCTCGACACAGCAGGT |
| KRASC61F001s | SEQ ID NO: 66 | GTTTTCCCAGTCACGACACGTTGGATGCTCTTGGATATT CTCGACACAGCAGGT |
| KRASc61F003 | SEQ ID NO: 67 | CCAGACTGTGTTTCTCCCTT |
| KRASC61F003s | SEQ ID NO: 68 | GTTTTCCCAGTCACGACACGTTGGATGCCAGACTGTGTT TCTCCCTT |
| KRASCONTRLFP | SEQ ID NO: 69 | TGAGGGAGATCCGACAATACAG |
| KRASCONTRLRP | SEQ ID NO: 70 | TCTGCCAAAATTAATGTGCTGAACT |
| L858RBR001 | SEQ ID NO: 71 | TTCTCTTCCGCACCCAGC |
| L858RBR001S | SEQ ID NO: 72 | CAGGAAACAGCTATGACACGTTGGATGTTCTCTTCCGCA CCCAGC |
| L858RNewFS | SEQ ID NO: 73 | GTTTTCCCAGTCACGACACGTTGGATGTGAAAACACCGC AGCATGTCAAGA |
| L858RNewFwd | SEQ ID NO: 74 | TGAAAACACCGCAGCATGTCAAGA |
| L858RNewRev | SEQ ID NO: 75 | CCTTACTTTGCCTCCTTCTGCATG |
| L858RNewRS | SEQ ID NO: 76 | CAGGAAACAGCTATGACACGTTGGATGCCTTACTTTGCC TCCTTCTGCATG |
| NC12FP004 | SEQ ID NO: 77 | TGGTGGGATCATATTCATCTACAAAG |
| NC12FP004_G13_Rev | SEQ ID NO: 78 | TGGTGGGATCATATTCATCTACAAAG |
| NC12FP004s | SEQ ID NO: 79 | CAGGAAACAGCTATGACACGTTGGATGTGGTGGGATCAT ATTCATCTACAAAG |
| NRAS117F001 | SEQ ID NO: 80 | AGTAAAAGACTCGGATGATGTACCTAT |
| NRAS117F002f | SEQ ID NO: 81 | ACGTTGGATGACCTATGGTGCTAGTGGGAAAC |
| NRAS117F003 | SEQ ID NO: 82 | ACGTTGGATGTCCCGTTTTTAGGGAGCAGA |
| NRAS117F004 | SEQ ID NO: 83 | CCCGTTTTTAGGGAGCAGAT |
| NRAS117R002 | SEQ ID NO: 84 | CAGTTCGTGGGCTTGTTTTG |
| NRAS117R004 | SEQ ID NO: 85 | CTTGCACAAATGCTGAAAGC |
| NRASc12F001 | SEQ ID NO: 86 | AAACTGGTGGTGGTTGGAGCA |
| NRASC12F001s | SEQ ID NO: 87 | GTTTTCCCAGTCACGACACGTTGGATGAAACTGGTGGTG GTTGGAGCA |
| NRASC13F001 | SEQ ID NO: 88 | GGTGGTGGTTGGAGCAGGT |
| NRASC13F001s | SEQ ID NO: 89 | GTTTTCCCAGTCACGACACGTTGGATGGGTGGTGGTTGG AGCAGGT |
| NRASC59F001 | SEQ ID NO: 90 | ACACCCCCAGGATTCTTACAGA |

-continued

| Sequence Name | | |
|---|---|---|
| NRASC59F001s | SEQ ID NO: 91 | GTTTTCCCAGTCACGACACGTTGGATGACACCCCCAGGA TTCTTACAGA |
| NRASC59R001 | SEQ ID NO: 92 | ATGGCACTGTACTCTTCTTGTCC |
| NRASC59R001s | SEQ ID NO: 93 | CAGGAAACAGCTATGACACGTTGGATGATGGCACTGTAC TCTTCTTGTCC |
| NRASc61F001 | SEQ ID NO: 94 | GTTGGACATACTGGATACAGCTGGA |
| NRASC61F001s | SEQ ID NO: 95 | GTTTTCCCAGTCACGACACGTTGGATGGTTGGACATACT GGATACAGCTGGA |
| NRASXN3REVSet4 | SEQ ID NO: 96 | CCGCAAATGACTTGCTATTA |
| NRASXN3RevSet4s | SEQ ID NO: 97 | CAGGAAACAGCTATGACACGTTGGATGCCGCAAATGACT TGCTATTA |
| NRASXN5FwSet1 | SEQ ID NO: 98 | ACACACTGGTAAGAGAAATAC |
| NRASXN5REVSet1 | SEQ ID NO: 99 | CTGAGTCCCATCATCACT |
| BR001 | SEQ ID NO: 100 | ATCGAGATTTCACTGTAGCTAGAC |
| DPCA001 | SEQ ID NO: 101 | ACTTCAGGCAGCGTCTTCA |
| DPCA002 | SEQ ID NO: 102 | TGTTCAGAGCACACTTCAG |
| DPCA003 | SEQ ID NO: 103 | CTGGTGGTTGAATTTGCTG |
| DPCA004 | SEQ ID NO: 104 | CATGAGCTCCAGCAGGATGAAC |
| DPCA005 | SEQ ID NO: 105 | CCGAAGTCTCCAATCTTGG |
| DPCA006 | SEQ ID NO: 106 | TAGATGTCTCGGGCCATCC |
| DPCBRC001 | SEQ ID NO: 107 | GGGACACTCTAAGAT |
| DPCBRC002 | SEQ ID NO: 108 | TTCTGTCCTGGGATTCTC |
| DPCBRC003 | SEQ ID NO: 109 | AGATTTTCCACTTGCTGT |
| DPCBRCA001-2 | SEQ ID NO: 110 | CCAGATGGGACACTCTAAGATTTTC |
| DPCBRCA002-2 | SEQ ID NO: 111 | CCTTTCTGTCCTGGGATTCTCTT |
| DPCBRCA003-2 | SEQ ID NO: 112 | GACAGATTTTCCACTTGCTGTGCTAA |
| DPCBRCA004 | SEQ ID NO: 113 | CATAAAGGACACTGTGAAGGCC |
| DPCBRCA004B | SEQ ID NO: 114 | D-LYS-O-GGCCTTCACAGTGTCCTTTATG |
| DPCCKT002 | SEQ ID NO: 115 | D-LYS-O-CATTCTTGATGTCTCTGGCTAG |
| DPCE001 | SEQ ID NO: 116 | GAGCCCAGCACTTT |
| DPCE001B | SEQ ID NO: 117 | D-LYS-O-CGGAGCCCAGCACTTTGAT |
| DPCE001B1 | SEQ ID NO: 118 | D-LYS-O-CGGAGCCCAGCACTTTGAT |
| DPCE002 | SEQ ID NO: 119 | NH(2)-AGATGTTGCTTCTCTTAA-CONH(2) |
| DPCE002B | SEQ ID NO: 120 | D-LYS-O-AGATGTTGCTTCTCTTAA |
| DPCE002C | SEQ ID NO: 121 | D-LYS-O-CGGAGATGTTGCTTCTCTTAATTCC |
| DPCE004 | SEQ ID NO: 122 | CAGTTTGGCCAGCCCA |
| DPCE004B | SEQ ID NO: 123 | CAGTTTGGCCAGCCCA-O-D-LYS |
| DPCE004C | SEQ ID NO: 124 | D-LYS-O-TTTGGCCAGCCCAAAATCTGT |
| DPCE004D | SEQ ID NO: 125 | D-LYS-O-GGCCAGCCCAAAATCTGT |
| DPCE005 | SEQ ID NO: 126 | ACCCAGCAGTTTGGC |

| Sequence Name | | |
|---|---|---|
| DPCE005B | SEQ ID NO: 127 | D-LYS-O-ACCCAGCAGTTTGGC |
| DPCE006 | SEQ ID NO: 128 | GCTGCGTGATGAG |
| DPCE007 | SEQ ID NO: 129 | GCTGCGTGATGA |
| DPCE008 | SEQ ID NO: 130 | AGCTCATCACGCAGCTCATG |
| DPCE008B | SEQ ID NO: 131 | D-LYS-O-CAGCTCATCACGCAGCTCATGC |
| DPCE008C | SEQ ID NO: 132 | D-LYS-O-TCATCACGCAGCTCATGCCCTT |
| DPCE008D | SEQ ID NO: 133 | D-LYS-O-CTCATCACGCAGCTCATG |
| DPCE008E | SEQ ID NO: 134 | D-LYS-O-TGAGCTGCGTGATG |
| DPCE009B | SEQ ID NO: 135 | D-LYS-O-TCCACGCTGGCCATCACGTA |
| DPCE009B-1 | SEQ ID NO: 136 | TCCACGCTGGCCATCACGTA-O-D-LYS |
| DPCE010B | SEQ ID NO: 137 | TGGGGGTTGTCCAC-O-D-LYS |
| DPCE011 | SEQ ID NO: 138 | GCACACGTGGGGGTT-O-D-LYS |
| DPCE012 | SEQ ID NO: 139 | D-LYS-O-ACAACCCCCACGTGTGC |
| DPCH001 | SEQ ID NO: 140 | CTGAGCCAGGAGAAAC |
| DPCH002 | SEQ ID NO: 141 | GTAAACTGAGCCAGGAG |
| DPCH003 | SEQ ID NO: 142 | ATGGCACTAGTAAACTGAGC |
| DPCH004 | SEQ ID NO: 143 | ATCCATATAACTGAAAGCCAA |
| DPCH005 | SEQ ID NO: 144 | ACCACATCATCCATATAACTGAA |
| DPCHRAS001B | SEQ ID NO: 145 | D-LYS-O-O-TTGCCCACACCGCCGGC |
| DPCHRAS002 | SEQ ID NO: 146 | D-LYS-O-O-TCTTGCCCACACCGCC |
| DPCHRAS003 | SEQ ID NO: 147 | D-LYS-O-O-TACTCCTCCTGGCCGGC |
| DPCJ001 | SEQ ID NO: 148 | CGTCTCCACAGACACATACTCCA |
| DPCJ002B | SEQ ID NO: 149 | CGTCTCCACAGACACATACTCCA-O-D-LYS |
| DPCK001B | SEQ ID NO: 150 | GCCTACGCCACCAGCTCCAAC-O-D-LYS |
| DPCK001B2 | SEQ ID NO: 151 | GCCTACGCCACCAGCTCCAAC-O-O-D-LYS |
| DPCK001C | SEQ ID NO: 152 | CTACGCCACCAGCTCCAACTACCA |
| DPCK001C2 | SEQ ID NO: 153 | CTACGCCACCAGCTCCAACTACCA-O-D-LYS |
| DPCK002 | SEQ ID NO: 154 | TCTTGCCTACGCCACCAGCTCCA |
| DPCK003 | SEQ ID NO: 155 | TGTACTCCTCTTGACCTGCTGTG |
| DPCK003B | SEQ ID NO: 156 | D-LYS-O-TGTACTCCTCTTGACCTGCTGTG |
| DPCK004 | SEQ ID NO: 157 | NH(2)-GGCAAATCACATTTATTTCCTAC-CONH(2) |
| DPCK004B | SEQ ID NO: 158 | D-LYS-O-GGCAAATCACATTTATTTCCTAC |
| DPCK005B | SEQ ID NO: 159 | D-LYS-O-TGTCTTGTCTTTGCTGATGTTTC |
| DPCK005 | SEQ ID NO: 160 | TGTCTTGTCTTTGCTGATGTTTC |
| DPCK005C | SEQ ID NO: 161 | D-LYS-O-TGTCTTGTCTTTGCTGATGTTTC |
| DPCK006 | SEQ ID NO: 162 | NH(2)-CTCTTGACCTGCTGTGTCGAG-CONH(2) |
| DPCN001 | SEQ ID NO: 163 | TCCCAACACCACCTGCTCCAA |
| DPCN001B | SEQ ID NO: 164 | D-LYS-O-CAACACCACCTGCTCCAACCACCAC |
| DPCN002 | SEQ ID NO: 165 | CTTTTCCCAACACCACCTGCTCC |

-continued

| Sequence Name | | |
|---|---|---|
| DPCN002B | SEQ ID NO: 166 | D-LYS-O-TGCGCTTTTCCCAACACCACCTGCT |
| DPCN003B | SEQ ID NO: 167 | GGCACTGTACTCTTCTTGTCCAG |
| DPCN004B | SEQ ID NO: 168 | D-LYS-O-TCTGGTCTTGGCTGAGGTTTC |
| DPCN006 | SEQ ID NO: 169 | NH(2)-GGCAAATCACACTTGTTTCCCAC-CONH(2) |
| DPCN006B | SEQ ID NO: 170 | D-LYS-O-GGCAAATCACACTTGTTTCCCAC |
| DPCN007 | SEQ ID NO: 171 | NH(2)-TTCTTGTCCAGCTGTATCCAGTATG-CONH(2) |
| DPCPKA003B | SEQ ID NO: 172 | D-LYS-O-AGATCCTCTCTCTGAAATCAC |
| DPCPKA004 | SEQ ID NO: 173 | D-LYS-O-TCTTTCTCCTGCTCAGTGATTTCA |
| DPCPKA005 | SEQ ID NO: 174 | D-LYS-O-AATGATGCACATCATGGTGGCTG |
| NRASN003C | SEQ ID NO: 175 | D-LYS-O-GGCACTGTACTCTTCTTGTCCAG |
| QMDXNA001 | SEQ ID NO: 176 | NH(2)-O-TTCATCAACCGCACTCTGTTTATCTC |
| QMDXNA002 | SEQ ID NO: 177 | NH(2)-O-TGGCGACGACAATGGACCCAATTAT |
| QMDXNA003 | SEQ ID NO: 178 | NH(2)-O-AGATGTAGTTAGCAATCGGTCCTTGTTGTA |
| QMDXNA004 | SEQ ID NO: 179 | NH(2)-O-GGGTAATTGAGGTAACGTAGGTATCAAGAT |
| QMDXNA005 | SEQ ID NO: 180 | NH(2)-O-TACTATCGACTGACATGAGGCTTGTGT |
| XNADE001 | SEQ ID NO: 181 | D-LYS-O-AGTCCGACGATCTGGAATTC |
| XNADE002 | SEQ ID NO: 182 | D-LYS-O-ACTGGAGTTCAGACGTGTG |
| XNADE003 | SEQ ID NO: 183 | D-LYS-O-CTCTTCCGATCAGATCGGAA |
| XNADE003b | SEQ ID NO: 184 | D-LYS-O-CTCTTCCGATCAGATCGGAAG |
| XNAFGFR001 | SEQ ID NO: 185 | D-LYS-O-O-AGCGCTCCCCGCACC |
| XNAFGFR001 | SEQ ID NO: 186 | D-LYS-O-O-AGCGCTCCCCGCACC |
| XNAFGFR002 | SEQ ID NO: 187 | D-LYS-O-GGGGAGCGCTCTGT-O-TTTTT |
| XNAFGFR003 | SEQ ID NO: 188 | D-LYS-O-O-AGCGCTCCCCGCACC-O-TTTTTT |
| XNAFGFR004 | SEQ ID NO: 189 | D-LYS-O-TGCATACACACTGCCCGCCT |

Other sequences of interest in connection with the invention include the following exons:

BRAF Ex 15 NCBI NG_007873.3;DNA;Wildtype
SEQ ID NO: 190
TAGAAATTAG ATCTCTTACC TAAACTCTTC ATAATGCTTG CTCTGATAGG AAAATGAGAT

CTACTGTTTT CCTTTACTTA CTACACCTCA GATATATTTC TTCATGAAGA CCTCACAGTA

AAAATAGGTG ATTTTGGTCT AGCTACAGTG AAATCTCGAT GGAGTGGGTC CCATCAGTTT

GAACAGTTGT CTGGATCCAT TTTGTGGATG GTAAGAATTG AGGCTATTTT CCACTGATT

AAATTTTTGG CCCTGAGATG CTGCTGAGTT ACTAGAAAGT CATTGAAGGT CTCAACTATA

GTATTTTCAT AGTTCCCAGT ATTCACAAAA ATCAGTGTTC TTATTTTTTA TGTAAATAGA

EGFR Ex18 GeneGenBank: AF288738.1 NCBI NM_005228.3; DNA;Wildtype
SEQ ID NO: 191
TAGAGAAGGC GTACATTTGT CCTTCCAAAT GAGCTGGCAA GTGCCGTGTC CTGGCACCCA

AGCCCATGCC GTGGCTGCTG GTCCCCCTGC TGGGCCATGT CTGGCACTGC TTTCCAGCAT

GGTGAGGGCT GAGGTGACCC TTGTCTCTGT GTTCTTGTCC CCCCCAGCTT GTGGAGCCTC

```
TTACACCCAG TGGAGAAGCT CCCAACCAAG CTCTCTTGAG GATCTTGAAG GAAACTGAAT

TCAAAAAGAT CAAAGTGCTG GGCTCCGGTG CGTTCGGCAC GGTGTATAAG GTAAGGTCCC

TGGCACAGGC CTCTGGGCTG GGCCGCAGGG CCTCTCATGG TCTGGTGGGG AGCCCAGAGT

CCTTGCAAGC TGTATATTTC CATCATCTAC TTTACTCTTT GTTTCACTGA GTGTTTGGGA

AACTCCAGTG TTTTTCCCAA GTTATTGAGA GGAAATCTTT TATAACCACA GTAATCAGTG
```

EGFR Ex19 GeneGenBank: AF288738.1 NCBI NM_005228.3; DNA;Wildtype
SEQ ID NO: 192

```
AGCCCAACAG CTGCAGGGCT GCGGGGGCGT CACAGCCCCC AGCAATATCA GCCTTAGGTG

CGGCTCCACA GCCCCAGTGT CCCTCACCTT CGGGGTGCAT CGCTGGTAAC ATCCACCCAG

ATCACTGGGC AGCATGTGGC ACCATCTCAC AATTGCCAGT TAACGTCTTC CTTCTCTCTC

TGTCATAGGG ACTCTGGATC CCAGAAGGTG AGAAAGTTAA AATTCCCGTC GCTATCAAGG

AATTAAGAGA AGCAACATCT CCGAAAGCCA ACAAGGAAAT CCTCGATGTG AGTTTCTGCT

TTGCTGTGTG GGGGTCCATG GCTCTGAACC TCAGGCCCAC CTTTTCTCAT GTCTGGCAGC

TGCTCTGCTC TAGACCCTGC TCATCTCCAC ATCCTAAATG TTCACTTTCT ATGTCTTTCC
```

EGFR Ex20 GeneGenBank: AF288738.1 NCBI NM_005228.3; DNA;Wildtype
SEQ ID NO: 193

```
AAAATTCCCG TCGCTATCAA GGAATTAAGA GAAGCAACAT CTCCGAAAGC CAACAAGGAA

ATCCTCGATG AAGCCTACGT GATGGCCAGC GTGGACAACC CCCACGTGTG CCGCCTGCTG

GGCATCTGCC TCACCTCCAC CGTGCAGCTCATCACGCAGC TCATGCCCTT CGGCTGCCTC

CTGGACTATG TCCGGGAACA CAAAGACAAT ATTGGCTCCC AGTACCTGCT CAACTGGTGT

GTGCAGATCG CAAAGGGCAT GAACTACTTG GAGGACCGTC GCTTGGTGCA CCGCGACCTG

GCAGCCAGGA ACGTACTGGT GAAAACACCG CAGCATGTCA AGATCACAGA TTTTGGGCTG

GCCAAACTGC TGGGTGCGGA AGAGAAAGAA TACCATGCAG AAGGAGGCAA AGTGCCTATC

AAGTGGATGG CATTGGAATC AATTTTACAC AGAATCTATA CCCACCAGAG TGATGTCTGG
```

EGFR Ex21 GeneGenBank: AF288738.1 NCBI NM_005228.3; DNA;Wildtyp
SEQ ID NO: 194

```
GGCATCTGCC TCACCTCCAC CGTGCAGCTC ATCACGCAGC TCATGCCCTT CGGCTGCCTC

CTGGACTATG TCCGGGAACA CAAAGACAAT ATTGGCTCCC AGTACCTGCT CAACTGGTGT

GTGCAGATCG CAAAGGGCAT GAACTACTTG GAGGACCGTC GCTTGGTGCA CCGCGACCTG

GCAGCCAGGA ACGTACTGGT GAAAACACCG CAGCATGTCA AGATCACAGA TTTTGGGCTG

GCCAAACTGC TGGGTGCGGA AGAGAAAGAA TACCATGCAG AAGGAGGCAA AGTGCCTATC

AAGTGGATGG CATTGGAATC AATTTTACAC AGAATCTATA CCCACCAGAG TGATGTCTGG

AGCTACGGGG TGACCGTTTG GGAGTTGATG ACCTTTGGAT CCAAGCCATA TGACGGAATC
```

HRAS Ex3 NCBI Reference Sequence: NG_007666.1; DNA;Wildtype
SEQ ID NO: 195

```
CTGCAGGATT CCTACCGGAA GCAGGTGGTC ATTGATGGGG AGACGTGCCT GTTGGACATC

CTGGATACCG CCGGCCAGGA GGAGTACAGC GCCATGCGGG ACCAGTACAT GCGCACCGGG

GAGGGCTTCC TGTGTGTGTT TGCCATCAAC AACACCAAGT CTTTTGAGGA CATCCACCAG

TACAGGTGAA CCCCGTGAGG CTGGCCCGGG AGCCCACGCC GCACAGGTGG GGCCAGGCC
```

JAK2 NCBI Reference Sequence: NG_009904.1; DNA; wildtype
SEQ ID NO: 196

```
CTGACATCTACCTCTAGTTGTACTTCTGTCCTCTATTTCAGGTGTTATGGGTCAAGCCTGTTTGA

CTGGCATTATTCATGATTCCTGTACCACTCTTGCTCTCTCTCACTTTGATCTCCATATTCCAGGC

TTACACAGGGGTTTCCTCAGAACGTTGATGGCAGTTGCAGGTCCATATAAAGGGACCAAAGCACA

TTGTATCCTCATCTAGTCATGCTGAAAGTAGGAGAAAGTGCATCTTTATTATGGCAGAGAGAATT

TTCTGAACTATTTATGGACAACAGTCAAACAACAATTCTTTGTACTTTTTTTTTTCCTTAGTCTT
```

-continued

TCTTTGAAGCAGCAAGTATGATGAGCAAGCTTTCTCACAAGCATTTGGTTTTAAATTATGGAGTA

TGTGTCTGTGGAGACGAGAGTAAGTAAAACTACAGGCTTTCTAATGCCTTTCTCAGAGCATCTGT

TTTTGTTTATATAGAAAATTCAGTTTCAGGATCACAGCTAGGTGTCAGTGTAAACTATAATTTAA

CAGGAGTTAAGTATTTTTGAAACTGAAAACACTGTAGGACTATTCAGTTATATCTTGTGAAAAG

GAAAGCAATGAAGTTAAAAGTAGAAGGTTACAATGCCCAAACAATAGAGTATTATAGTAAACAAA

TGTCTATAAAACATTTTGTGTTCATGATAGCAAAAGAGATTATGGCAGGTTCAACATAACATTGG

AATAACTGGCCTTTTCAGTACAAACTTATCTGGAATTATGAAGACAAAGCATA

KRAS Ex2 NCBI Reference Sequence: NG_007524.1; DNA; wildtype
SEQ ID NO: 197
GGTACTGGTG GAGTATTTGA TAGTGTATTA ACCTTATGTG TGACATGTTC TAATATAGTC

ACATTTTCAT TATTTTTATT ATAAGGCCTG CTGAAAATGA CTGAATATAA ACTTGTGGTA

GTTGGAGCTG GTGGCGTAGG CAAGAGTGCC TTGACGATAC AGCTAATTCA GAATCATTTT

GTGGACGAAT ATGATCCAAC AATAGAGGTA AATCTTGTTT TAATATGCAT ATTACTGGTG

KRAS Ex3 NCBI Reference Sequence: NG_007524.1; DNA; wildtype
SEQ ID NO: 198
CTTCTCAGGA TTCCTACAGG AAGCAAGTAG TAATTGATGG AGAAACCTGT CTCTTGGATA

TTCTCGACAC AGCAGGTCAA GAGGAGTACA GTGCAATGAG GGACCAGTAC ATGAGGACTG

GGGAGGGCTT TCTTTGTGTA TTTGCCATAA ATAATACTAA ATCATTTGAA GATATTCACC

ATTATAGGTG GGTTTAAATT GAATATAATA AGCTGACATT AAGGAGTAAT TATAGTTTTT

KRAS Ex4 NCBI Reference Sequence: NG_007524.1; DNA; wildtype
SEQ ID NO: 199
GTGCTATAAC TTTTTTTTCT TTCCCAGAGA ACAAATTAAA AGAGTTAAGG ACTCTGAAGA

TGTACCTATG GTCCTAGTAG GAAATAAATG TGATTTGCCT TCTAGAACAG TAGACACAAA

ACAGGCTCAG GACTTAGCAA GAAGTTATGG AATTCCTTTT ATTGAAACAT CAGCAAAGAC

AAGACAGGTA AGTAACACTG AAATAAATAC AGATCTGTTT TCTGCAAAAT CATAACTGTT

ATGTCATTTA ATATATCAGT TTTTCTCTCA ATTATGCTAT ACTAGGAAAT AAAACAATAT

KRAS Ex5 NCBI Reference Sequence: NG_007524.1; DNA; wildtype
SEQ ID NO: 200
AATGCAACAG ACTTTAAAGA AGTTGTGTTT TACAATGCAG AGAGTGGAGG ATGCTTTTTA

TACATTGGTG AGGGAGATCC GACAATACAG ATTGAAAAAA ATCAGCAAAG AAGAAAAGAC

TCCTGGCTGT GTGAAAATTA AAAAATGCAT TATAATGTAA TCTGGTAAGT TTAAGTTCAG

NRAS Exon 2 NCBI Reference Sequence: NG_007572.1; DNA; wildtype
SEQ ID NO: 201
GTGTTTTTGC GTTCTCTAGT CACTTTAAGA ACCAAATGGA AGGTCACACT AGGGTTTTCA

TTTCCATTGA TTATAGAAAG CTTTAAAGTA CTGTAGATGT GGCTCGCCAA TTAACCCTGA

TTACTGGTTT CCAACAGGTT CTTGCTGGTG TGAAATGACT GAGTACAAAC TGGTGGTGGT

TGGAGCAGGT GGTGTTGGGA AAAGCGCACT GACAATCCAG CTAATCCAGA ACCACTTTGT

AGATGAATAT GATCCCACCA TAGAGGTGAG GCCCAGTGGT AGCCCGCTGA CCTGATCCTG

TCTCTCACTT GTCGGATCAT CTTTACCCAT ATTCTGTATT AAAGGAATAA GAGGAGAGAA

AGTAAAAAGT TATTTTGGGT ATACATTCAG TTATGCAATA AGCTTAACGT GTTTATAGAG

AACAGTTCAT TTTTATTAGC TGCTGAAGTT CTAAAACCT GTCCAGTTTT TAACAGTTCT

NRAS Exon 3 NCBI Reference Sequence: NG_007572.1; DNA; wildtype
SEQ ID NO: 202
TGGGCTTGAA TAGTTAGATG CTTATTTAAC CTTGGCAATA GCATTGCATT CCCTGTGGTT

TTTAATAAAA ATTGAACTTC CCTCCCTCCC TGCCCCCTTA CCCTCCACAC CCCCAGGATT

CTTACAGAAA ACAAGTGGTT ATAGATGGTG AAACCTGTTT GTTGGACATA CTGGATACAG

-continued

CTGGACAAGA AGAGTACAGT GCCATGAGAG ACCAATACAT GAGGACAGGC GAAGGCTTCC

TCTGTGTATT TGCCATCAAT AATAGCAAGT CATTTGCGGA TATTAACCTC TACAGGTACT

AGGAGCATTA TTTTCTCTGA AAGGATGATC TTTGTGTTCT GAATCTTTAT GGGGAAATGA

GGTTACCACA CTAGGGAAGA TAGAGCTTTT TAATTATGGG AAGAGTTGGT TTTAGGTTGT

TTGACATTGA GAATCTAGGG TAATTACTGA AAGTTAATAC TGGAATTTAT TTTACATAAT

NRAS Exon 4 NCBI Reference Sequence: NG_007572.1; DNA; wildtype
SEQ ID NO: 203
TGGATACAGC TGGACAAGAA GAGTACAGTG CCATGAGAGA CCAATACATG AGGACAGGCG

AAGGCTTCCT CTGTGTATTT GCCATCAATA ATAGCAAGTC ATTTGCGGAT ATTAACCTCT

ACAGGGAGCA GATTAAGCGA GTAAAAGACT CGGATGATGT ACCTATGGTG CTAGTGGGAA

ACAAGTGTGA TTTGCCAACA AGGACAGTTG ATACAAAACA AGCCCACGAA CTGGCCAAGA

GTTACGGGAT TCCATTCATT GAAACCTCAG CCAAGACCAG ACAGGGTGTT GAAGATGCTT

TTTACACACT GGTAAGAGAA ATACGCCAGT ACCGAATGAA AAAACTCAAC AGCAGTGATG

ATGGGACTCA GGGTTGTATG GGATTGCCAT GTGTGGTGAT GTAACAAGAT ACTTTTAAAG

204 PIK3CA Ex9 NCBI Reference Sequence: NG_012113.2; DNA; wildtype
SEQ ID NO: 204
TGTAAAATTT ATTGAAAATG TATTTGCTTT TTCTGTAAAT CATCTGTGAA TCCAGAGGGG

AAAAATATGA CAAAGAAAGC TATATAAGAT ATTATTTTAT TTTACAGAGT AACAGACTAG

CTAGAGACAA TGAATTAAGG GAAAATGACA AGAACAGCT CAAAGCAATT TCTACACGAG

ATCCTCTCTC TGAAATCACT GAGCAGGAGA AAGATTTTCT ATGGAGTCAC AGGTAAGTGC

TAAAATGGAG ATTCTCTGTT TCTTTTTCTT TATTACAGAA AAAATAACTG AATTTGGCTG

ATCTCAGCAT GTTTTTACCA TACCTATTGG AATAAATAAA GCAGAATTTA CATGATTTTT

PIK3CA Ex20NCBI Reference Sequence: NG_012113.2; DNA; wildtype
SEQ ID NO: 205
TAGCTATTCG ACAGCATGCC AATCTCTTCA TAAATCTTTT CTCAATGATG CTTGGCTCTG

GAATGCCAGA ACTACAATCT TTTGATGACA TTGCATACAT TCGAAAGACC CTAGCCTTAG

ATAAAACTGA GCAAGAGGCT TTGGAGTATT TCATGAAACA AATGAATGAT GCACATCATG

GTGGCTGGAC AACAAAAATG GATTGGATCT TCCACACAAT TAAACAGCAT GCATTGAACT

GAAAAGATAA CTGAGAAAAT GAAAGCTCAC TCTGGATTCC ACACTGCACT GTTAATAACT

PIK3CA Ex16 NCBI Reference Sequence: NG_012113.2; DNA; wildtype
SEQ ID NO: 206
GTTGTAAATCTTTGTAACACTTCAAAAAGCTATATTGTATTTATATTTTAAAATAAATTTCAGGG

TAAAATAATAATAAAGCAAAGGTACCTAGTAAAGTTTTTAACTATTTTAAAGGCTTGAAGAGTGT

CGAATTATGTCCTCTGCAAAAAGGCCACTGTGGTTGAATTGGGAGAACCCAGACATCATGTCAGA

GTTACTGTTTCAGAACAATGAGATCATCTTTAAAAATGGGGATGGTAAGGAAGAGTATTAATGAG

CTTATGATGCATGAATTTAGCTATCTTTTTATACACAGGATATTTATGAACCATGAAAACTACTG

AAAGCCATTTAAGGAATATACACATGTGATAAAATATGTAATATTTATCAGATGTCTTGACCTTT

GAAATATGCATGTATAATCAATGAAAAGAAAAGAAGTACTAGGTTTAGATCAGAAGTCCTGAAAT

CAGTTTTTTGTTTTTTCTTTTTCCTGTTCCCTGCC

Other XNA sequences used in the invention and more in particular with respect to Example 6 of the invention includes:

```
EGFR G719
                                    SEQ ID NO: 207
D-Lys-O-CG_OAGA_AAGCCC_OAAGCACTTTGAT

EGFR Ex19Del
                                    SEQ ID NO: 208
D-Lys-O-C_OAG_OAG_OAA_OAG_OAATGTTGCT_OAT_OACTCTTAATTCC

EGFR T790
                                    SEQ ID NO: 209
D-Lys-O-T_AAC_AAA_AATCAC_OAGC_OAAGCTC

EGFR L858
                                    SEQ ID NO: 210
D-Lys-O-GGCCAGC_OAC_OACAAAAT_AACTGT

NRAS G12
                                    SEQ ID NO: 211
D-Lys-O-C_OAAA_OACAC_AAC_AAAC_OACTGCTCCAACCACCAC

NRAS A59
                                    SEQ ID NO: 212
D-Lys-O-TTC_OATTGTC_OACA_OAGCT_AAGTAT_AACCAGTATG

KRAS G12
                                    SEQ ID NO: 213
D-Lys-O-C_AATACGCCACC_OAAGCTC_OACAACTACCA

KRAS A59
                                    SEQ ID NO: 214
D-Lys-O-C_OATCTTGACCT_OAGCT_OAGTGT_AACGAG

KRAS A146
                                    SEQ ID NO: 215
D-Lys-O-T_OAGTCTTTAAGCTG_OAATGT

APC E1309
                                    SEQ ID NO: 216
D-Lys-O-C_AATGAC_OACTAGT_OATCCAAT_AACTTTTCTT

PIK3CA H1047
                                    SEQ ID NO: 217
D-Lys-O-A_OAATGAT_AAGCACATCAT_OAGGTGGCTG

CTNNB1 S45
                                    SEQ ID NO: 218
D-Lys-O-C_AATCCTT_OACTCTAAGAG_OATG

BRAF V600
                                    SEQ ID NO: 219
D-Lys-O-A_OATC_OAGAGATAATT_OACACT_AAGTAGCTAGAC
```

In sequences 207 through 219 the subscripts designations OA and AA stand for oxy-aza and aza-aza moieties in the Xenonucleic acid.

Example 6

The Following is exemplary of XNA Oligomer Synthesis: Part I. Synthetic Procedure of the Fmoc Oxy-Aza-T XNA Monomer.

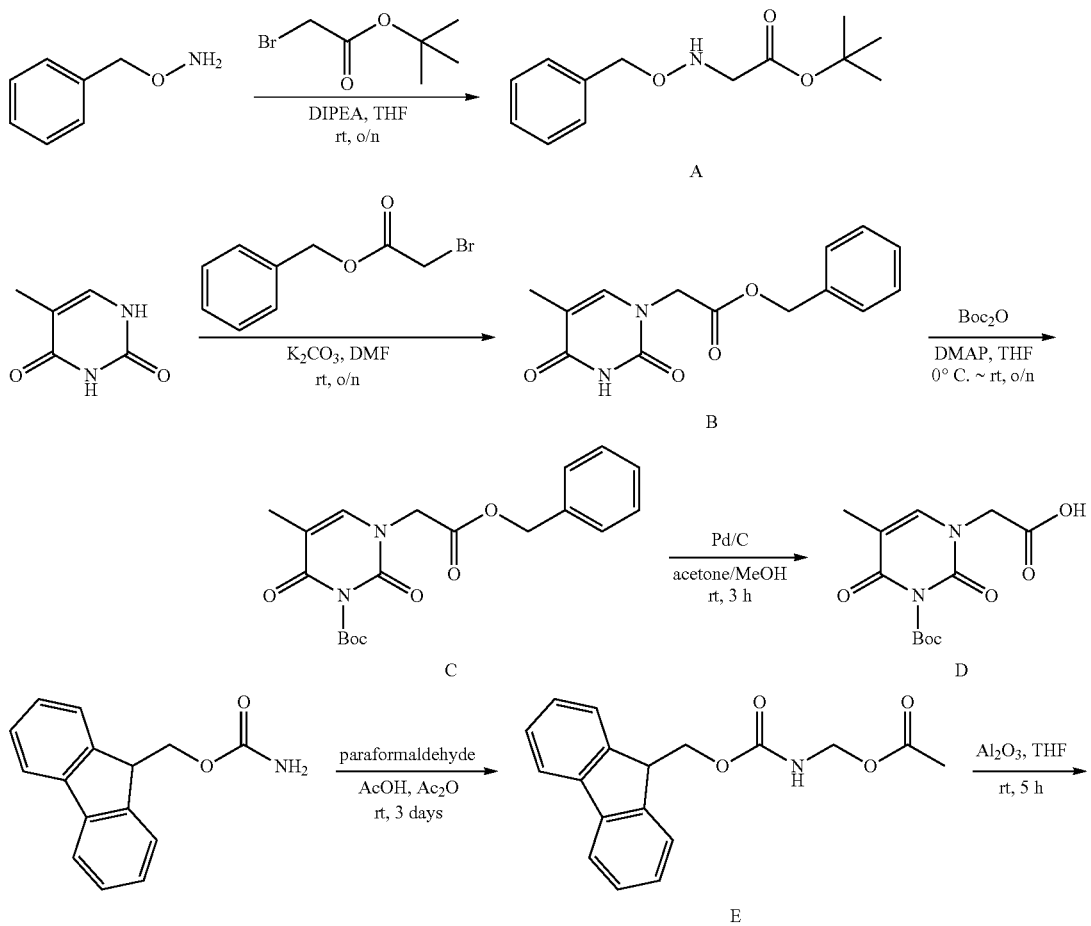

-continued
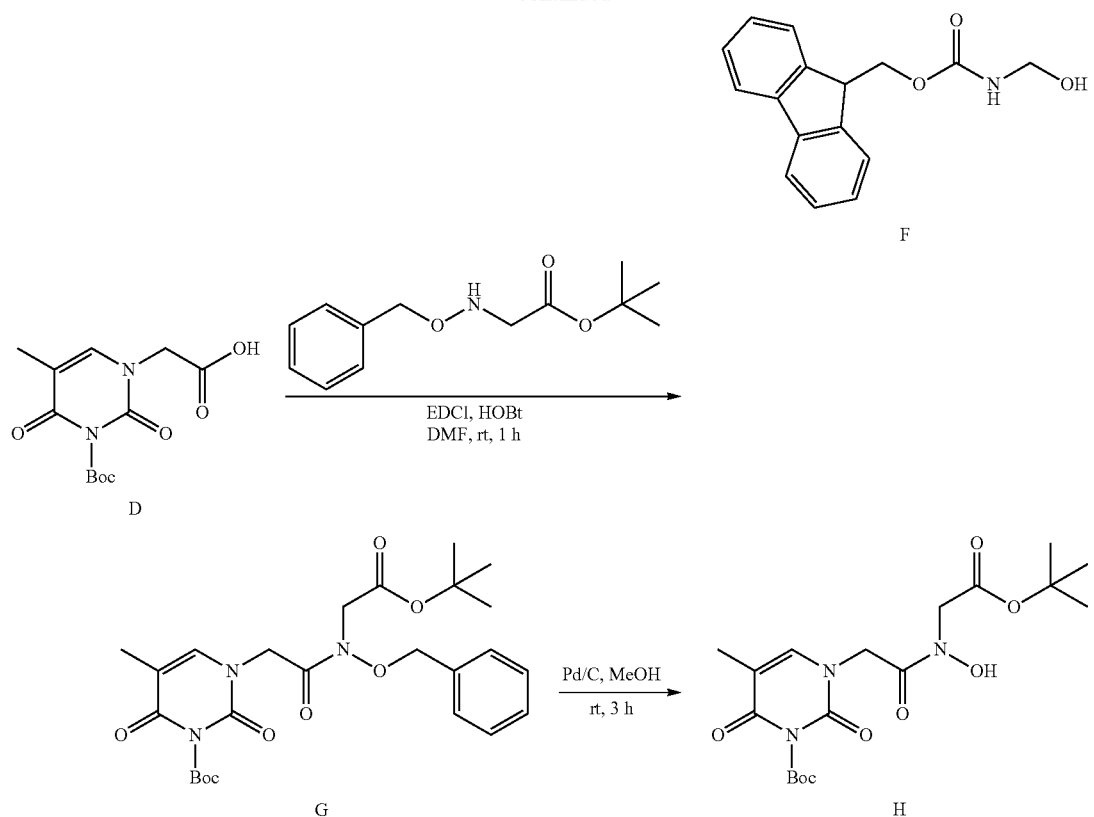
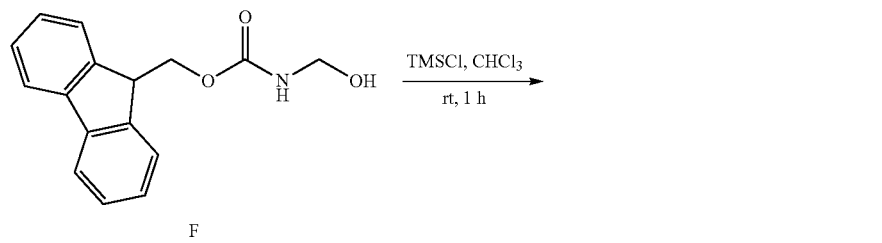
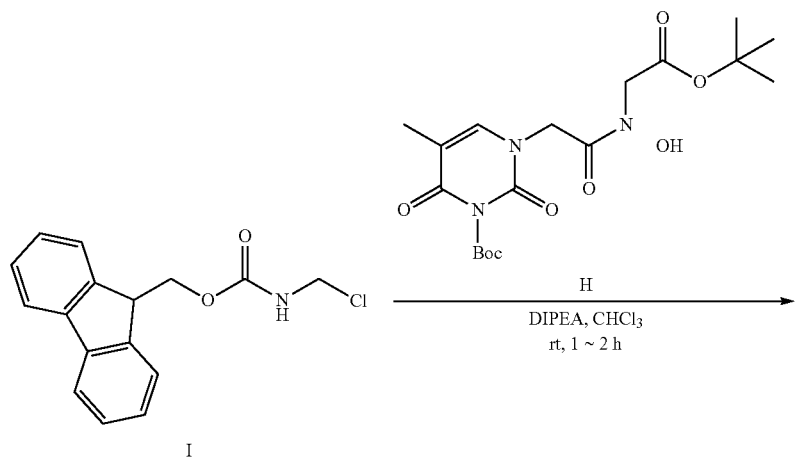

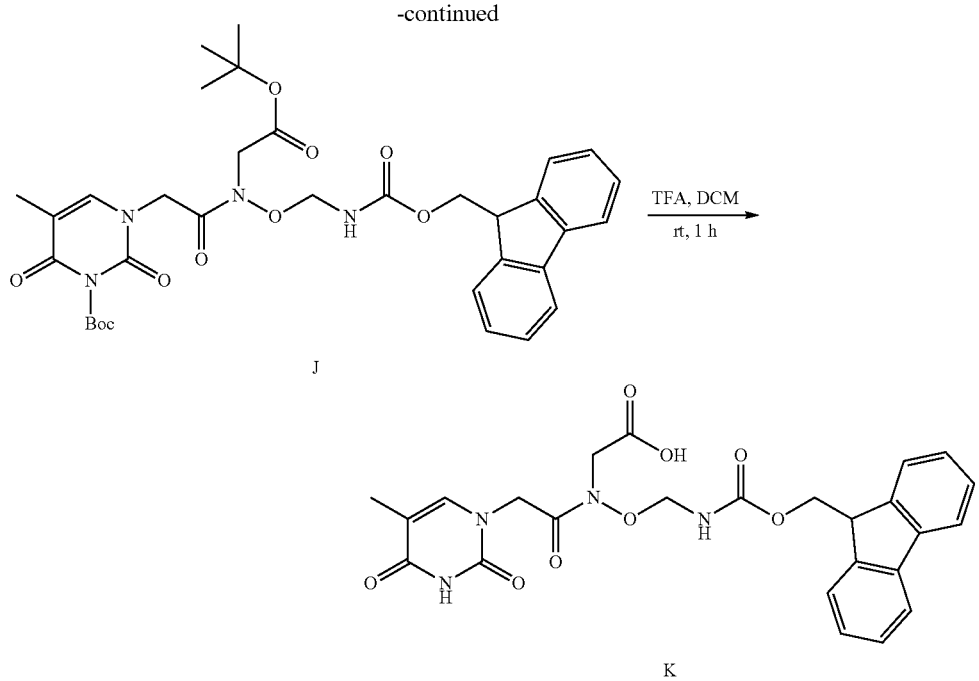

The other oxy-aza nucleotide Monomers A, C and G are prepared similarly with suitable protecting groups on the nucleoside bases.

Step 1:

To a solution of O-benzylhydroxylamine (2.00 g, 15.9 mmol) and diisopropylethylamine (3.08 mL, 17.51 mmol) in THF (25 mL) was added dropwise tert-butyl 2-bromoacetate (2.5 mL, 16.71 mmol) in THF (10 mL). The reaction mixture was stirred at 50° C. for 4 hours then at room temperature overnight. Solvent was removed under vacuum to obtain crude which was purified by Biotage Isolera flash column to obtain title compound A (1.17 g, 29.4%) as a colorless oil.

Step 2:

Thymine (3.00 g, 23.0 mmol) and potassium carbonate (3.30 g, 24.0 mmol) were dissolved in dry N,N-dimethylformamide (~70 mL). Benzyl bromoacetate (3.50 mL, 22.0 mmol) was added dropwise and the reaction mixture was stirred at room temperature overnight. The suspension was filtered and solvent was removed to obtain a residue which was purified by Biotage flash column to obtain compound B (4.09 g, 61.4%) as a white solid.

Step 3:

Benzyl 2-(5-methyl-2,4-dioxo-3,4-dihydropyrimidin-1(2H)-yl)acetate (3.00 g, 10.0 mmol), di-tert-butyl decarbonate (4.92 mL, 22.0 mmol), and 4-dimethylaminopyridine (2.56 g, 22 mmol) were added to THF (~30 mL) at 0° C. The reaction mixture was stirred at 0° C. for 30 minutes and then at room temperature overnight. The solvent was removed. The residue was dissolved in dichloromethane (100 mL) and washed with water, brine, and dried over anhydrous $MgSO_4$, filtered and concentrated. The crude was purified by Biotage flash column to obtain compound C (2.91 g, 71.1%) as a white solid.

Step 4:

To a solution of tert-butyl 3-(2-(benzyloxy)-2-oxoethyl)-5-methyl-2,6-dioxo-2,3-dihydropyrimidine-1(6H)-carboxylate (2.91 g, 7.38 mmol) in methanol (30 mL) and acetone (30 mL), 5% Pd/C (582 mg) was added. The reaction mixture was degassed with hydrogen 3 times and stirred at room temperature under hydrogen for 3 hours. The mixture was filtered with celite and washed with methanol and acetone. The filtrate was concentrated to obtain crude compound D (1.84 g, 83.3%).

Step 5:

(9H-fluoren-9-yl)methyl carbamate (3.00 g, 12.0 mmol) and paraformaldehyde (0.43 g, 14.0 mmol), were suspended in a mixture of acetic acid (22.5 mL) and acetic anhydride (70 mL). The reaction mixture was stirred at room temperature for 3 days and then filtered. The solvent was removed by distillation in vacuum and the crude was purified by flash column to get compound E (3.46 g, 85.9%) as a white solid.

Step 6:

((((9H-fluoren-9-yl)methoxy)carbonyl)amino)methyl acetate (3.40 g, 10.0 mmol) was dissolved in THF (~10 mL) and loaded on a 68-gram neutral alumina column. The loaded cartridge was allowed to stand for 5 hours then eluted by THF, and thereafter concentrated to obtain compound F (1.28 g, 43.5%) as a white solid.

Step 7:

N,N-diisopropylethylamine (1.15 mL, 6.49 mmol) was added to a solution of 2-(3-(tert-butoxycarbonyl)-5-methyl-2,4-dioxo-3,4-dihydropyrimidin-1(2H)-yl)acetic acid (1.03 g, 3.245 mmol), tert-butyl 2-((benzyloxy)amino)acetate (0.89 g, 3.57 mmol), 1-Ethyl-3-(3-dimethylaminopropyl) carbodiimide-HCl (3.38 g, 17.13 mmol) and hydroxybenzotriazole hydrate (2.68 g, 17.13 mmol) in N,N-dimethylformamide (~40 mL). The reaction mixture was stirred at room temperature overnight and diluted with dichloromethane (~50 mL). The solution was washed with water, brine, dried over anhydrous $MgSO_4$, filtered and concentrated. The crude was purified by flash column to obtain compound G (1.08 g, 59.5%) as a white solid.

Step 8:

To a solution of tert-butyl 3-(2-((benzyloxy)(2-(tert-butoxy)-2-oxoethyl)amino)-2-oxoethyl)-5-methyl-2,6-dioxo-2,3-dihydropyrimidine-1(6H)-carboxylate (Compound G;

1.08 g, 2.04 mmol) in methanol (10 mL), 5% Pd/C (216 mg) was added. The reaction mixture was degassed with hydrogen for 3 times and stirred at room temperature under hydrogen for 3 hours. The mixture was filtered by celite and washed with methanol. The filtrate was concentrated to obtain a crude compound H (865 mg, 97.6%) as white foam.

Steps 9 and 10:

To a solution of (9H-fluoren-9-yl)methyl (hydroxymethyl)carbamate (Compound F; 1.03 g, 3.63 mmol) in chloroform (40 mL), trimethylsilyl chloride (0.93 mL, 7.267 mmol) was added dropwise and stirred at room temperature for 1 hour. After 1 hour, tert-butyl 3-(2-((2-(tert-butoxy)-2-oxoethyl)(hydroxy)amino)-2-oxoethyl)-5-methyl-2,6-dioxo-2,3-dihydropyrimidine-1(6H)-carboxylate (1.74 g, 4.00 mmol) and N,N-diisopropylethylamine (2.58 mL, 14.53 mmol) were added to the above solution. The reaction mixture was stirred at room temperature for 1 hour. The reaction mixture was washed with water, brine, dried over anhydrous $Na_2SO_4$, filtered, and concentrated to get the residue which was purified by flash column to get compound J (762 mg, 30.0%) as a white solid.

Step 11:

To a solution of tert-butyl 3-(7-(2-(tert-butoxy)-2-oxoethyl)-1-(9H-fluoren-9-yl)-3,8-dioxo-2,6-dioxa-4,7-diazanonan-9-yl)-5-methyl-2,6-dioxo-2,3-dihydropyrimidine-1 (6H)-carboxylate (0.60 g, 0.857 mmol) in dichloromethane (~12 mL), trifluoroacetic acid was added (~5 mL, 85.8 mmol) at 0~5° C. The reaction mixture was stirred at room temperature for 1 hour. The mixture was concentrated to obtain a residue which was purified by Biotage Isolera flash column to obtain the title compound (220 mg, 48.0%) as an off-white solid.

$^1$H NMR (300 MHz, CDCl3): 10.3 (s, 1H), 8.75 (s, 1H), 7.88 (d, J=7.5 Hz, 2H), 7.69 (d, J=7.3 Hz, 2H), 7.44-7.29 (m, 5H), 4.92 (d, J=6.1 Hz, 2H), 4.66 (s, 2H), 4.40-4.37 (m, 2H), 4.25 (t, J=6.4 Hz, 1H), 4.08-3.97 (m, 2H), 1.73 (s, 3H) ppm. LC-MS $[M+Na]^+$: 508.97, $[M+Na]^+$: 531.23. HPLC purity: 95.7% at 254 nm.

Part II. Synthesis of Chemically-Modified EGFR c797S XNA, Using Fmoc Oxy-Aza-T XNA Monomer (Bold Red) to Replace the Regular Fmoc-T Monomer (Bold Black) as Specified Below:

```
EGFR c797S
Regular-T original sequence:
                                   SEQ ID NO: 246
5'-D-LYS-O-TTCGGCTGCCTCCTGG-3'

Partial Oxy-Aza-T Replacement Sequence:
                                   SEQ ID NO: 247
5'-D-LYS-O-TTCGGCT_OAGCCT_OACCTGG-3' where OA is oxy-aza.
``` a) Solid-Phase Synthesis Step

This step has been conducted on an INTAVIS MultiPep automatic synthesizer (INTAVIS Bioanalytical Instruments AG, Cologne, Germany), coupled with a compact Welch vacuum pump (4 m$^3$ per hour ventilation rate), a 20-liter stainless steel waste container, and a long ventilation hose to discharge the solvent vapor and smell from the system into a nearby chemical fume hood.

In a typical 24-port (4×6) array plate, a micro column (0.5-ml capacity) with PTFE filters was inserted tightly into a chosen port. A certain weight of TentaGel resin (1 micromole, namely 10.0 mg resin at 0.10 mmol/gram loading capacity) was loaded to this column.

Four regular monomers (Fmoc-T/A/C/G) and O-linker monomer (Fmoc-AEEA-OH) were purchased commercially (98+% purity) and prepared freshly as 0.3 M solutions in N-methyl 2-pyrrolidone (NMP); Fmoc-D-Lysine(t-Boc) monomer as a 0.5 M solution in NMP. This unconventional Fmoc Oxy-Aza-T monomer was also made as a 0.3 M solution in a smaller 15-ml polypropylene vial (100 mg about 0.2 mmol dissolved in 600 uL of NMP solvent), and was accordingly given a new code of monomer in the program (perhaps like "oaT"?). All other reagents (from Sigma-Aldrich if not specified otherwise, with purity of 98% or higher) include 0.5 M DMF solution of HATU (from P3 BioSyetems Inc, 1-[Bis(dimethylamino)-methylene]-1H-1,2,3-triazolo[4,5-b]pyridinium 3-oxid hexafluorophosphate, Hexafluoro-phosphate Azabenzotriazole Tetramethyl Uronium) for carboxy activation, a base solution containing 1.2 M DIPEA and 1.8 M 2,6-lutidine(1:1, v/v) in DMF for acid scavenger, a 20% piperidine solution in DMF (v %) for Fmoc group deprotection, 5% (v %) acetic anhydride in DMF for amino capping procedure, NMP and methylene chloride and ethanol for column wash use.

After the preparative procedures above are completed, the XNA sequence was input to the operating PC's INTAVIS program with double check. The automatic synthesis on the TentaGel resin was started from the 3' terminal of XNA sequence (namely from C-terminal) following this program, using a pre-set 1-micromole-scale double-coupling synthesis method. Briefly, in a typical cycle, a double deprotection, a double coupling and a single capping procedure was included to assure the sufficiently high-yielding and clean synthesis; a molar ratio of HATU/Base/monomer/amino=5:25:5:1 was chosen in general. The synthesizer was programmed to automatically repeat the cycles from 3' end to 5' end, till the 5' end of the sequence that is the D-lysine terminus here. At this last cycle, the resin was thoroughly washed and then dried. Resin weight was found to increase obviously.

b) Resin Cleavage and Side-Chain Deprotection

The dried resin was transferred to a 50-ml polypropylene centrifuge vial, using methylene chloride as the suspension medium for an easy and complete transfer, then dried in vacuum. A cocktail of TFA/m-cresol/TIPS/water (90:5:2.5:2.5, v %) was added (1000 uL for 1 umol resin), the cleavage/deprotection procedure was carried out at room temperature on an orbital shaker for 3 hrs at 160 cpm. The resin was then filtered out, the filtrate (~1 mL) was mixed with 40-mL of cold anhydrous ether (0-5 Celsius degree), a significant amount of off-white loose precipitate appeared. The precipitate was collected and vacuum-dried after high-speed centrifuge (4500 cpm, 20 minutes) on a WAVERLY fixed-angle centrifuge. The crude solid was redissolved in about 300 ul of water for HPLC purification.

c) HPLC Purification of Fmoc-ON XNA

Our Agilent HPLC 1100 system consists of a G1322A degasser, G1311A Quaternary Pump, G1313A automatic sampler, G1316A column compartment with temperature control and G1315B diode array detector.

A typical HPLC purification run is conducted as below on a Aeris peptide XB-C18 RP-HPLC column (100×4.5 mm, 3.6 um particle size): 5%-29% gradient of mobile phase B in 0-28 minutes (mobile phase A: 0.1% TFA in water; mobile phase B: 0.1% TFA in acetonitrile) for elation of the XNA product and byproduct peaks, followed by 29%-60% wash for 4 minutes (28-32 min), and then 60%-5% wash back to equilibrate the column for the next run (32-36 min). Other parameters: 1.0 ml/min flow rate, column temperature 50.0+/−0.5 Celsius degree, UV detection at 260 nm and 205 nm simultaneously (detecting DNA base and TFA impurity respectively), a single sample injection as 100 ul each run.

The XNA product peak fractions (a main and sharp peak usually in the range of 17-23 min) were collected and combined, as the eluted solution of purified XNA (Fmoc-ON version).

d) Lyophilization of Fmoc-ON XNA

The purified Fmoc-ON XNA solution (in mixed solvent of water and acetonitrile, with 0.1% TFA) was transferred to a 50-ml centrifuge vial (polypropylene) and frozen either in cold bath of dry-ice/acetone or −80 Celsius degree freezer, then subjected to lyophilization.

A 1200-ml LABCONCO flask including the frozen sample vial(s) was attached to a port of multifold of a LABCONCO desktop lyophilizer (Freezone 4.5 model) which was already stabilized at −40 Celsius degree and approximately 100 microbar (0.1 mmHg). The process continued usually for 8-48 hours depending on total sample volume. Upon completion of this process, a loose and white solid was obtained as the dried XNA product (Fmoc-ON version).

This version of purified XNA can be used directly after being re-dissolved in water or TE buffer. The product quantity can be calculated by the base concentration measured at 260 nm and the XNA solution total volume, then the synthetic yield (%) can be calculated. MALDI-TOF mass spectrum of the synthesized XNA (Fmoc-ON version) was measured on Shimadzu Axima MALDI-TOF mass spectrometer and data was recorded, using sinapinic acid as the matrix and the bovine cytochrome C protein as the molecular weight reference standard. If even higher water solubility is mandatory, then the deprotection of the terminal Fmoc group of the purified XNA above can be further processed, see Step (e) and Step (f) below.

e) Additional D-Lysine Fmoc Deprotection and Further HPLC Purification

The purified XNA above is redissolved in small amount of DMF (e.g. 300 ul for each micromole), then a calculated amount of piperidine was added in at room temperature so as to make it a 10% piperidine/DMF solution, the deprotection only took a few minutes to complete. Following the deprotection, 40-ml of cold anhydrous ether is added to precipitate the crude product.

Another round of HPLC was repeated with the conditions listed above, the Fmoc-OFF XNA peak comes out earlier, usually in the range of 10-15 min window due to its increased hydrophilicity and thus less stronger adsorption on the RP-HPLC column. All product fractions were collected and combined.

f) Further Lyophilization and Formulation

Lyophilization procedure is similar to the procedure (d) described above, during which the acetonitrile and TFA can be completely removed, leaving a final powder product of XNA (Fmoc-OFF version).

The product quantity can be calculated by the base concentration measured at 260 nm and the XNA solution total volume, and then the synthetic yield (%) can be calculated.

MALDI-TOF mass spectrum of the synthesized XNA (Fmoc-OFF version) was measured on Shimadzu Axima MALDI-TOF mass spectrometer and data was recorded, using sinapinic acid as the matrix and the bovine cytochrome C protein as the molecular weight reference standard.

The powder XNA is then redissolved in either pure water or TE buffer, as an aqueous solution of typically 200 micromolar concentration. The resulting solution can be either directly used for the subsequent XNA clamping-based qPCR or aliquoted (e.g. 50 ul=10 nmol) for lyophilization again to store for long term.

Other XNA oligomers can be synthesized in a similar fashion composed partially or entirely of oxy-aza, aza-aza and/or sulfa-aza (thio-aza) XNA monomers.

Example 7

XNA-Based OPTISEQ™ Lung and Colorectal Cancer Dual Cancer Panel, a High Sensitivity Method for Cancer Diagnostic Patient Eligibility Patient eligibility criteria included, histological or cytological diagnosis of advanced solid cancer, potential candidates for phase I/II clinical trials, at least one biopsiable lesion, laboratory parameters safe for tumor biopsy and written voluntary informed consent.

DNA Extraction

The DNA of lung/Colorectal Cancer patients' samples were manually extracted using QIAamp DNA FFPE Tissue Kit (Qiagen, Venlo, Limburg, Netherlands) following the manufacturer's protocol. Eluted DNA was measured using Qubit™ dsDNA HS Assay kit (ThermoFisher Scientific Corp., Waltham, Mass., USA), according to the manufacturer's recommendations. At least 10 ng DNA was obtained for each sample for following amplicon sequencing.

Preparation of Genomic DNA Reference Standard Mix

17 Cell line genomic DNA containing specific human cancer mutation were obtained from Horizon Discovery (Horizon Discovery Group plc, Waterbeach, UK) and other commercial vendors. Wild type human gDNA controls were obtained from Bioline (London, UK). Human gDNA containing cancer mutants were pooled in equal amount, and then mixed with wild type controls to reconstitute human tumor samples containing 0.00%, 0.10% 0.25%, 0.50% and 1.25% of mutant alleles in 17 hotspots mutants covered by OptiSeq™ lung and colorectal cancer mini panel. 10 ng of tumor samples/reference genomic DNA standard mix were used for library preparation.

Primers and XNA Mix

The experiment was conducted using OptiSeq™ lung and colorectal cancer mini panel in the presence and absence of XNA oligomers pool (a mixture of 13 XNAs). OptiSeq™ lung and colorectal cancer mini panel contains PCR primers for amplification of 13 amplicons, which cover 17 hotspots in 7 frequently mutated oncogenes. 17 mutations and corresponding drug therapy and related diseases were summarized in Table 18 (Supplementary to Table 11). Primer sequences and corresponding hotspot covered information were listed in Table 19 (Supplementary to Table 12). It also contains 13 XNAs individually designed and optimized for enrichment of mutant alleles targeted by 13 amplicons. These genes, hotspots and XNAs covered by OptiSeq™ Nano panel V2 are illustrated in Table 11. PCR primer concentration of OptiSeq™ lung and colorectal cancer dual cancer panel in reaction was 100 nM.

For some of XNAs, they are able to target for more than one mutant hotspot present in same amplicon, due to close approximate locations. For example, XNA "NRAS A59" are able to target for hotspots "NRAS A59" and "NRAS Q61". In this case, only a single XNA "NRAS A59" is applied to enrich these two hotspots. The classifications of mutation type of each hotspot are included in Table 11, as well.

Library Preparation

Libraries were prepared by using in-house developed protocol. The protocol is for targeted enrichment sequencing.

The details of protocol was attached as supplementary file at the end of this article. There are six steps in total and required reagents and vendors' information were listed in Table 12. Amongst 6 steps, two PCR reaction steps are included 1st Target PCR Amplification and 2nd Indexing PCR Amplification. 1st Target PCR Amplification: 95° C. for 10 mins; 18 cycles for 98° C. for 15 sec; 60° C. for 5 mins; then 10° C. until being used for next 1st Beads Clean-up Step. While for PCR protocol of 2nd Indexing PCR Amplification: 98° C. for 30 sec; 12 cycles at 98° C. for 10 sec; 60° C. for 20 sec; 72° C. for 10 sec; Keep samples at 10° C. until being used for next 3rd Beads Clean-up Step. At 3rd Beads Clean-up, 10 μL elution nuclease-free water is used to elute and dissolve the library. Qubit 4 Fluorometer instrument (Thermo Fisher Scientific, MA, USA) was applied to quantify library. All libraries for one sequencing run were pooled together with equimolar amount. Pooled library was quantified by Qubit as well. Agilent 2100 BioAnalyzer (Agilent Technologies, CA, USA) was applied to make sure the targeted amplicons of pooled library fall within the expected range.

TABLE 11

Gene and Hotspots covered OptiSeq ™ Nano Panel V2 as well as corresponding XNA information

| Hotspots # | Gene Name | Hotspots Covered by XNA | Mutation Type | XNA # | XNA Name | XNA Concentration, nM |
|---|---|---|---|---|---|---|
| 1 | NRAS | A59 | SNV | 1 | NRAS A59 | 200 |
| 2 | NRAS | Q61 | SNV | | | |
| 3 | NRAS | G12 | SNV | 2 | NRAS G12 | 8 |
| 4 | NRAS | G13 | SNV | | | |
| 5 | CTNNB1 | S45 | Deletion | 3 | CTNNB1 S45 | 100 |
| 6 | PIK3CA | H1047 | SNV | 4 | PIK3CA H1047 | 15 |
| 7 | APC | E1309 | Deletion | 5 | APC E1309 | 200 |
| 8 | EGFR | G719 | SNV | 6 | EGFR G719 | 300 |
| 9 | EGFR | E746-A750 | Deletion | 7 | EGFR E746-A750 | 300 |
| 10 | EGFR | T790 | SNV | 8 | EGFR T790 | 30 |
| 11 | EGFR | L858 | SNV | 9 | EGFR L858 | 100 |
| 12 | BRAF | V600 | SNV | 10 | BRAF V600 | 70 |
| 13 | KRAS | A146 | SNV | 11 | KRAS A146 | 250 |
| 14 | KRAS | A59 | SNV | 12 | KRAS A59 | 550 |
| 15 | KRAS | Q61 | SNV | | | |
| 16 | KRAS | G12 | SNV | 13 | KRAS G12 | 30 |
| 17 | KRAS | G13 | SNV | | | |

Sample Sequencing and Data Analysis

MiSeq Sequencing System (Illumina Inc., US) was applied to sequence the libraries. Sample sheet was generated by using Illumina Experiment Manager version 1.11.0. "Fastq Only" was chosen as the application of this sequencing run. TruSeq HT was chosen as the selected barcodes. Cluster density of sequenced pooled libraries should fall within the range from 800-1200 K/mm$^2$, otherwise being deemed as failing QC criteria. Besides cluster density, clusters passing filter (>90%) and Q30 score (>90%) are included in quality control criteria to evaluate the sequencing quality. After sequencing is done, resulting fastq data of each sample was analyzed using Biomedical Genomics Workbench (Qiagen, Hilden, Germany) to generate calls and allele frequency reports. The experiment and data analysis workflows are shown in FIG. 14.

TABLE 12

Brief summary of library preparation protocols and required reagents/volume information

| Step Name | Reagents (Volume, μL) | Vendor |
|---|---|---|
| 1st Target PCR Amplification | 2X mPCR Premix (5) | DiaCarta, Inc |
| | OptiSeqTM Lung and Colorectal Cancer Mini Panel (1) | DiaCarta, Inc |
| | | DiaCarta, Inc |
| | OptiSeq ™ XNA Mix (1) | Horizon Discovery Group plc |
| | DNA Template (1~3) | GE Healthcare Life Science |
| | Nuclease-free Water (0~2) | N/A |
| | Total (10) | |
| 1st Bead Cleanup | PlexPure Magnetic Beads (13) | DiaCarta, Inc |
| | 70% Ethanol (Details in | DiaCarta, Inc |

TABLE 12-continued

Brief summary of library preparation protocols and required reagents/volume information

| Step Name | Reagents (Volume, μL) | Vendor |
|---|---|---|
| | Supplementary) | GE Healthcare Life Science |
| | Nuclease-free Water | |
| Non-Specific Amplicon Digestion | 20X mPCR Cleanup Mix (1) | DiaCarta, Inc |
| | 10× mPCR Cleanup Buffer (2) | DiaCarta, Inc |
| | 10× Cleanup Stop Buffer (2) | DiaCarta, Inc |
| | Nuclease-free Water (7) | GE Healthcare Life Science |
| 2$^{nd}$ Bead Cleanup | PlexPure Magnetic Beads (29) | DiaCarta, Inc |
| | 70% Ethanol | DiaCarta, Inc |
| | Nuclease-free Water | GE Healthcare Life Science |
| 2$^{nd}$ Indexing PCR Amplification | 2X Indexing PCR Premix (10) | DiaCarta, Inc |
| | Index Primer (10 μM) (2) | DiaCarta, Inc |
| 3$^{rd}$ Bead Cleanup | PlexPure Magnetic Beads (18) | DiaCarta, Inc |
| | 70% Ethanol | DiaCarta, Inc |
| | Nuclease-free Water | GE Healthcare Life Science |

Investigate the XNA Enrichment Effects on Variant Allelic Frequency

Effects of 13 XNAs mix on blocking wild type alleles and enrichment of mutant alleles were investigated by performing multiplexing PCR on control cell line human tumor gDNA samples containing low percentage of cancer mutant variant alleles frequency (VAF, 0.00%, 0.10%, 0.25%, 0.50%, and 1.25%) in wild type background, in the presence and absence of XNA oligomers. Results from six experimental replicates were obtained for each type of human standard reference sample mix to evaluate assay reproducibility. After indexing PCR, libraries were pooled and sequenced using Illumina MiSeq and resulting fastq data of each sample was analyzed using Biomedical Genomics Workbench to generate calls and allele frequency reports. The experiment and data analysis workflows are shown in FIG. 14.

Figure 13:
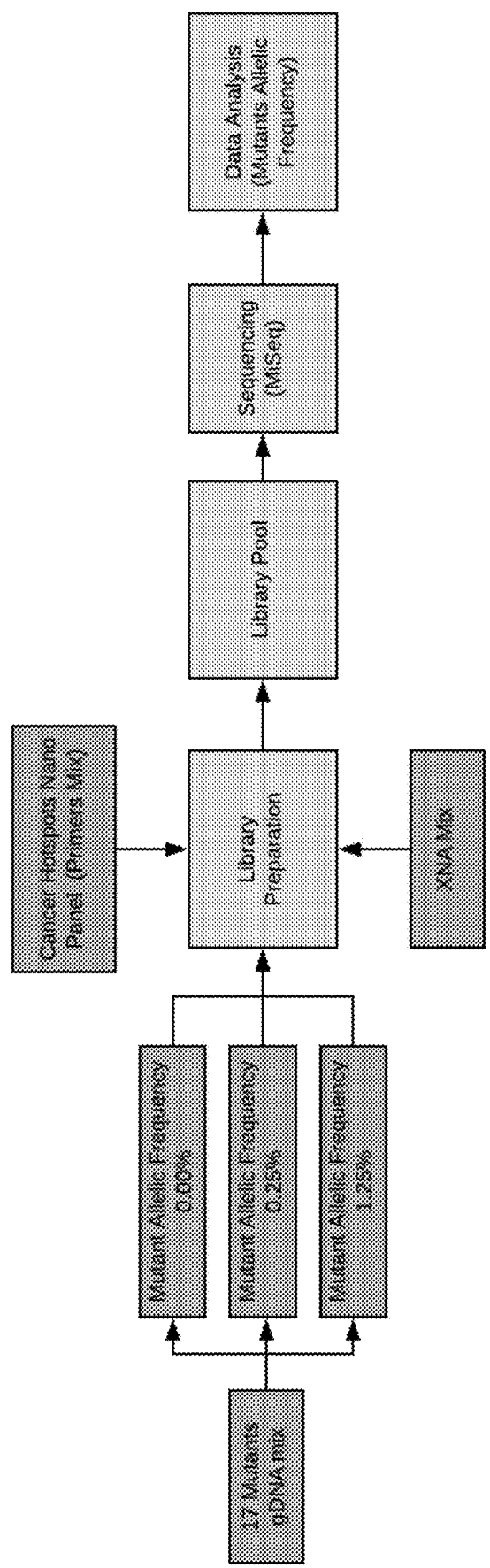
FIG. 13 shows experimental and data analysis workflows for study of XNA effects on enrichment of variant alleles.
Figure 14A:
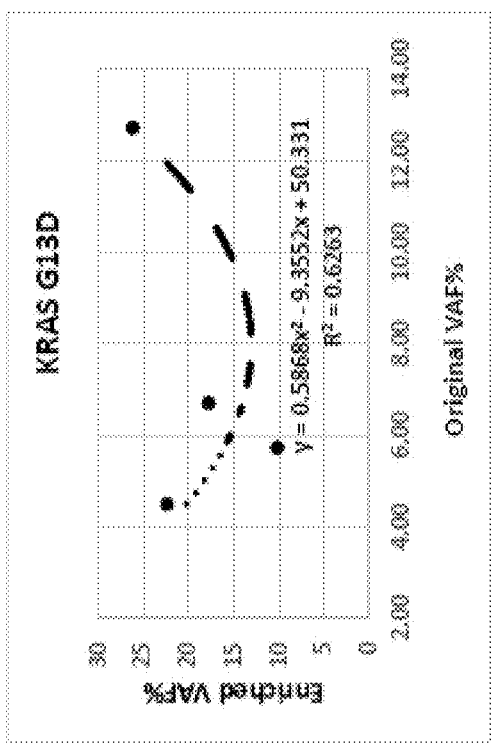
FIGS. 14A to 14Q shows the correlation of enriched variants allelic frequency (Enriched VAF) and original variant allelic frequency (more than 2.00%) (Original VAF) with corresponding regression equations.
Figure 14B:
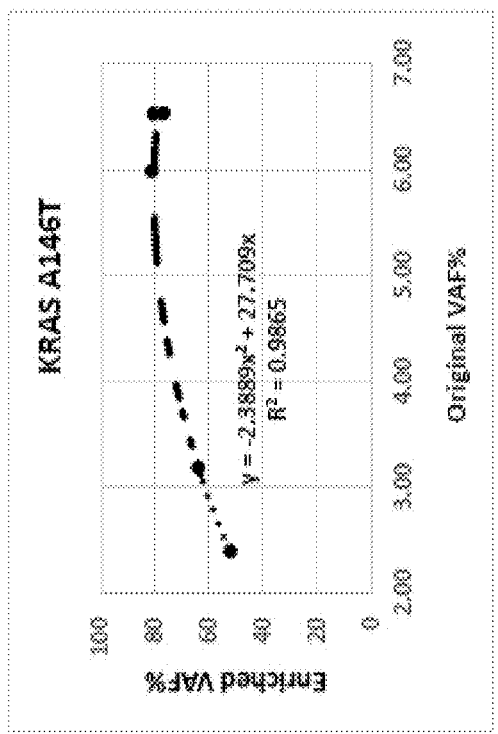
Figure 14C:
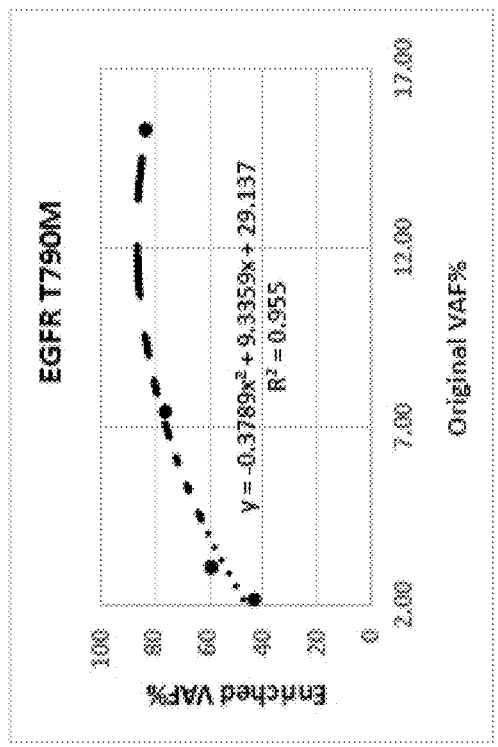
Figure 14D:
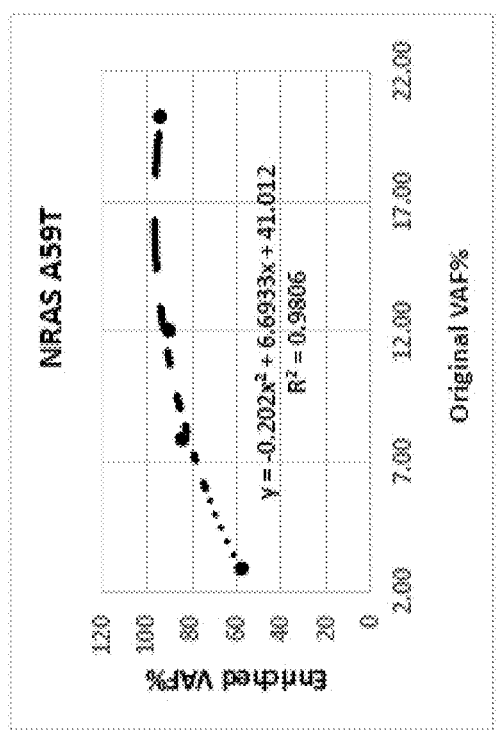
Figure 14E:
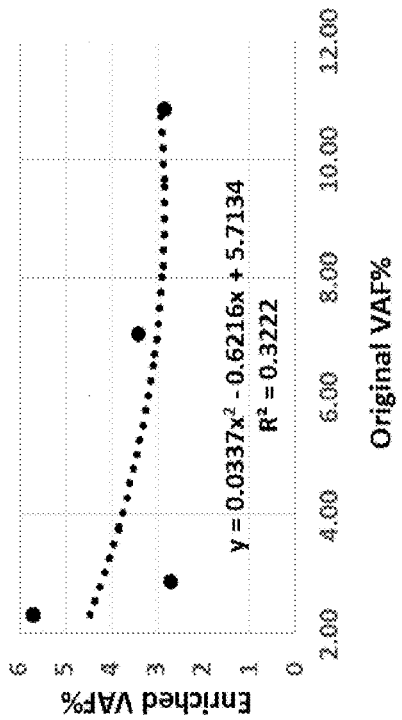
Figure 14F:
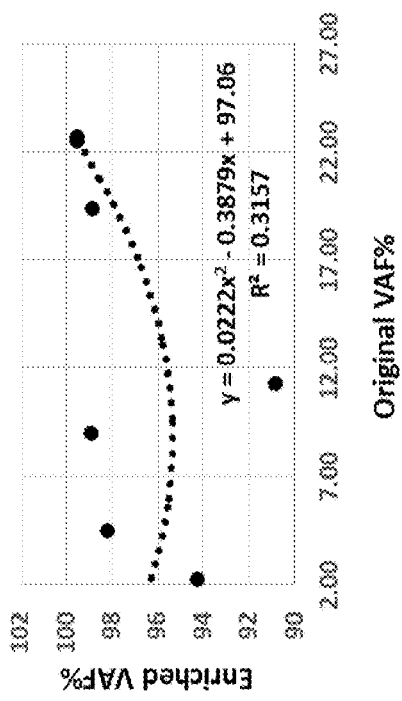
Figure 14H:
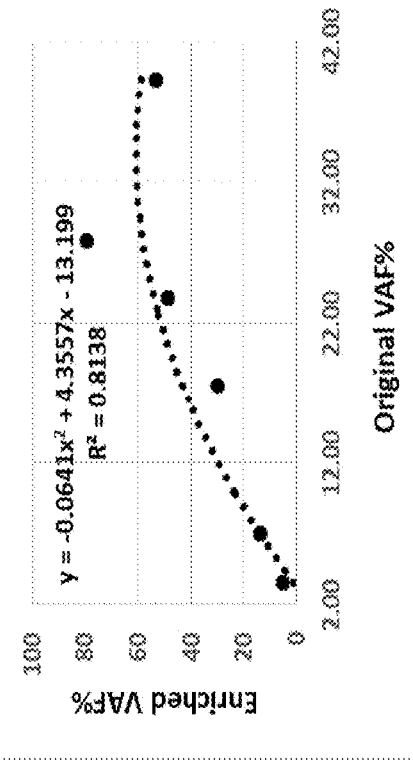
Figure 14G:
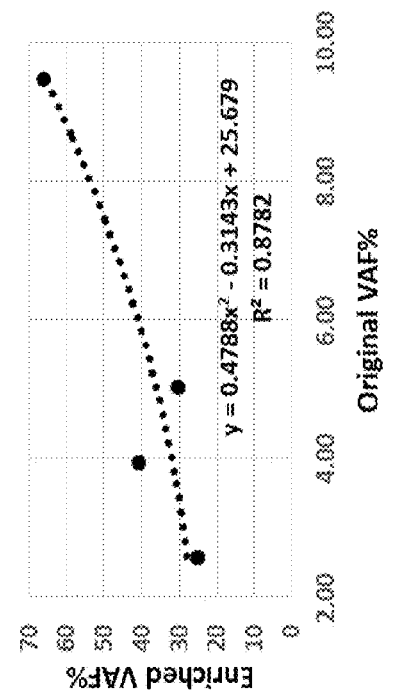
Figure 14I:
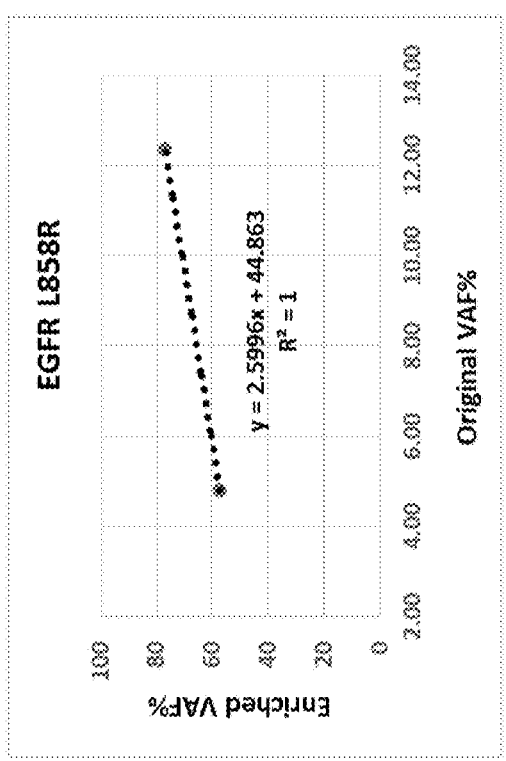
Figure 14J:
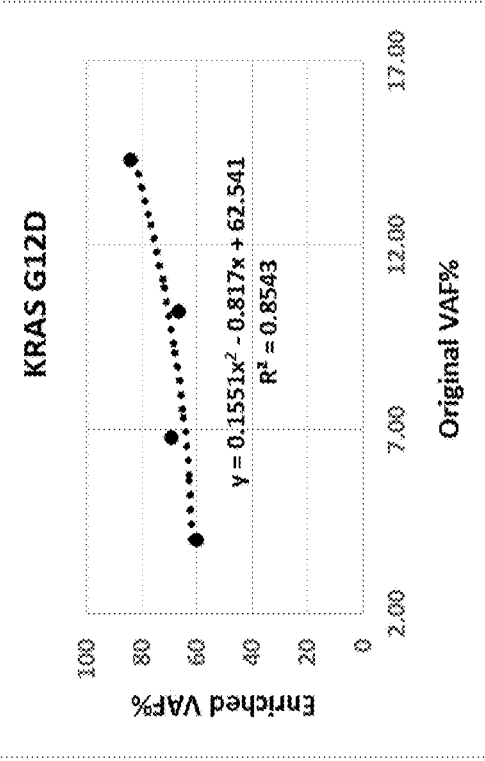
Figure 14K:
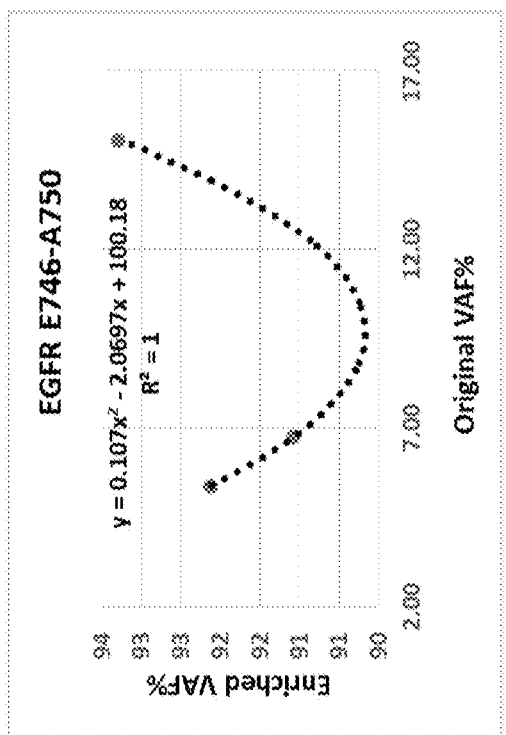
Figure 14L:
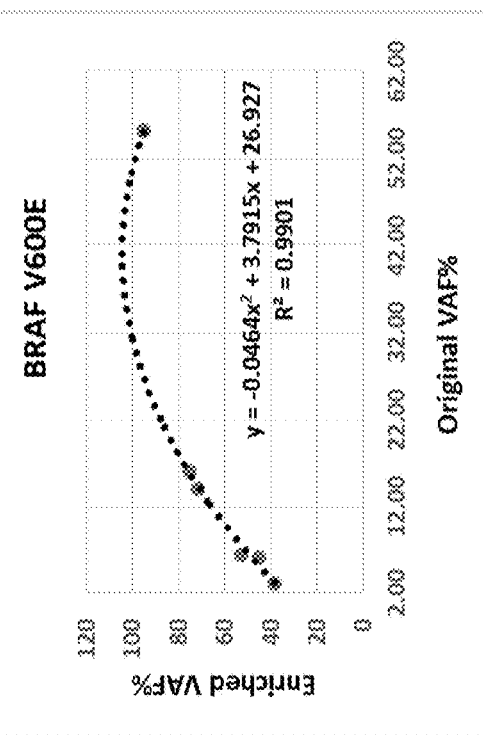
Figure 14M:
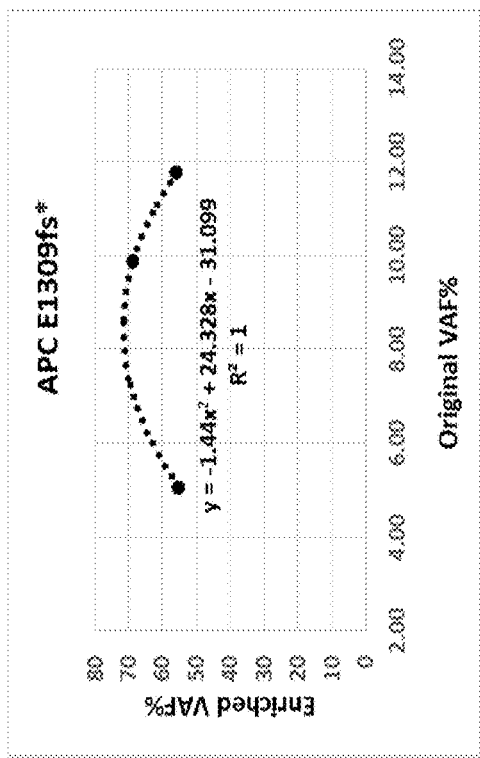
Figure 14N:
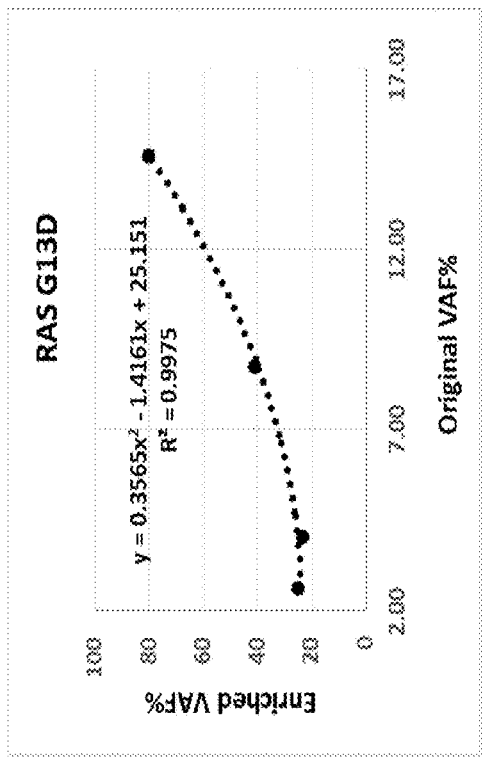
Figure 14O:
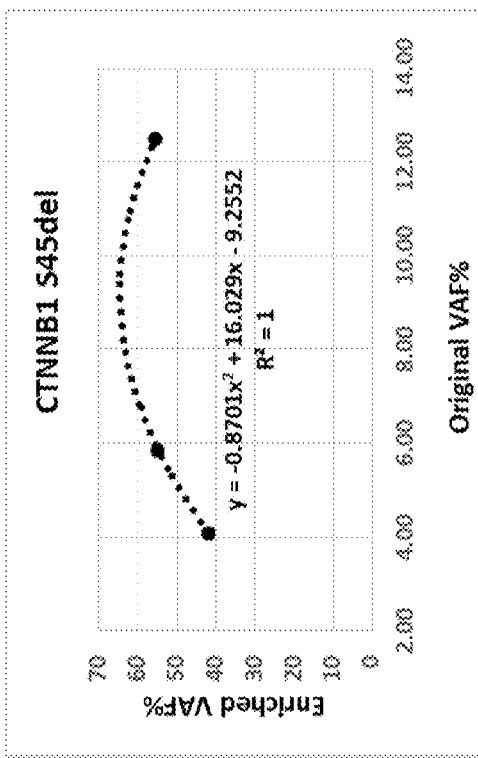
Figure 14P:
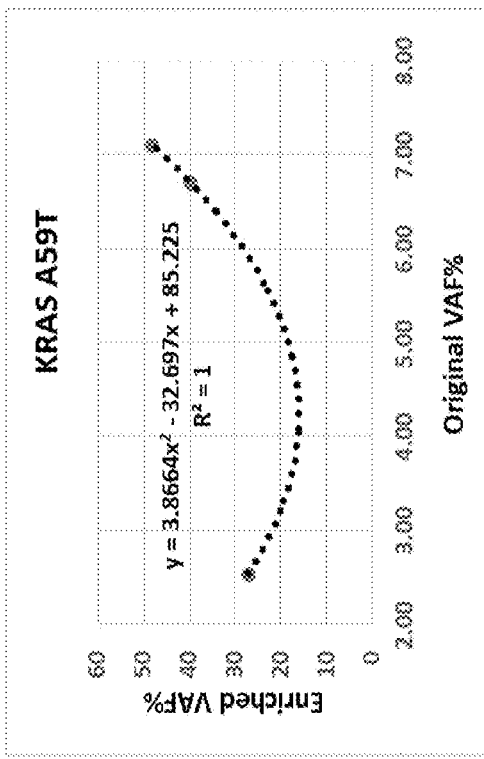
Figure 14Q:
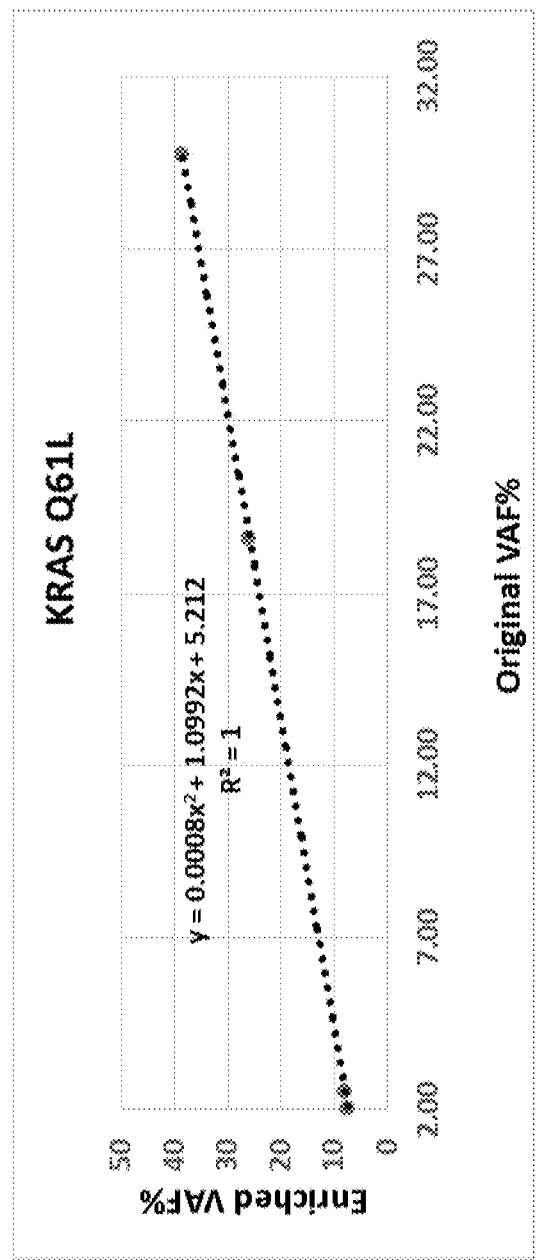

Determine the Correlation of Enriched Variant Frequency and Original Variant Frequency To determine the relationship between enriched variant allelic frequency (Enriched VAF) and original allelic frequency (Original VAF), cell line human tumor gDNA samples containing same frequency cancer mutant alleles (0.00%, 0.50%, 1.00%, 2.50%, 5.00%, 10.00% and 15.00% VAF) were prepared in wild type background, in the presence and absence of XNA oligomers. Six experimental replicates were obtained for each condition. After indexing PCR, libraries were pooled and sequenced using Illumina MiSeq and resulting fastq data of each sample was analyzed using Qiagen Biomedical Genomics Workbench to generate calls and allele frequency reports. The experiment and data analysis workflows are shown in supplementary FIG. 13.

Verification Study of XNA Enrichment Effects on Patients' Samples

Effects of 13 XNAs mix on detecting the VAF % of lung and colorectal cancer patients' samples were also investigated. Total 36 patient samples were investigated in this study (14 lung cancer and 10 colorectal Formalin-Fixed, Paraffin-Embedded (FFPE) patients, 10 lung Cancer and 2 colorectal cell-free DNA patients' samples were investigated in this validation experiment. 2 replicates of each patient samples were included. 10 ng DNA (Maximum DNA amount of cfDNA samples input were used due to the limited amount of the DNA, Maximum amount DNA is 10 ng) for each library construction procedure. The experiment and data analysis workflows are the same as the above protocols.

Xenonucleic Acids Structure and its Function

Xenonucleic acids (XNA), are innovative new nucleic acid molecular oligomers that hybridize by Watson-Crick base pairing to target DNA sequences yet have a modified chemical backbone. XNA oligomers are highly effective at hybridizing to targeted normal DNA sequences and can be employed as molecular clamps in quantitative real-time polymerase chain reactions (PCR) or as highly specific molecular probes for detection of nucleic acid target sequences. The XNA tightly binds to the wild-type sequence that is 100% complementary in sequence and blocks DNA polymerase from DNA elongation; only the mutant target sequence gets amplified because the XNA:mutant DNA duplex is not stable due to mismatch and fall off from the template in PCR reactions.

Effects of XNAs Mix on Enrichment of Mutants in Human Reference Standard gDNA Mix Samples XNAs mix was spiked into the PCR reaction containing OptiSeq™ Dual Cancer Panel primer mix and human reference standard gDNA control samples containing mutants at different abundance levels. The estimated VAFs of 17 hotspots in human tumor samples were at 0.00%, 0.10%, 0.25%, 0.50% and 1.25%, respectively, of which mutant copy number at 5 different frequency were 0, 3, 8, 17 and 42, respectively.

Figure 8:
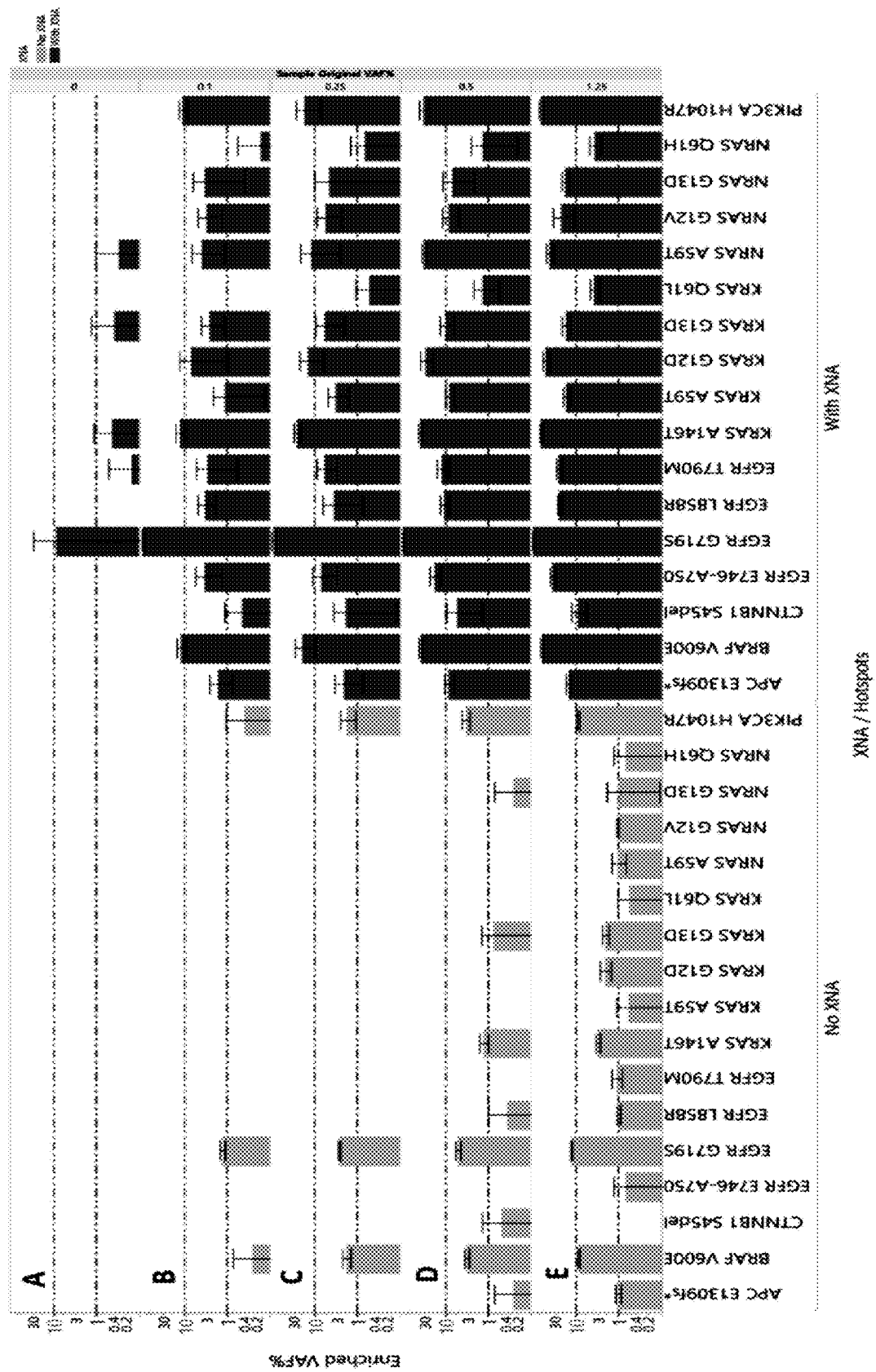
FIG. 8 describes the effects of XNA mix on Variant Allelic Frequency (VAF) using OPTISEQ™ Dual Cancer Panel.

The detected VAFs by Next Generation Sequencing are shown in FIG. 8. The mutant detection powered by the XNAs mix was dramatically boosted. There were, on average, 32.0, 23.7, 25.0 and 18.4 folds of increase in VAF for synthetic tumor samples with 0.10%, 0.25%, 0.50% and 1.25% mutants, respectively.

On samples originally with 1.25% of mutants, in 14 of 17 hotspots, observed VAFs were more than 10% after XNA enrichment. This result suggested that XNA is able to enrich mutant alleles and make high confidence calls. It is also noticeable that some hotspots were enriched less efficiently than others. For example, "CTNNB1 S45del" was enriched from 0.96% to 7.82%. In addition, "KRAS Q61L" was merely enriched from 1.16% to 2.80%. Furthermore, "NRAS Q61H" was enriched from 0% to 1.15%, after adding XNA. These results suggested that the design of XNA and/or experimental condition should be further improved.

In samples containing 0.00% mutants or negative controls, the VAFs were either small or undetectable. The reason for detection of mutants in negative control in the presence of XNA is likely due to low level of DNA contamination from environment or some unknown mutations present in cell line DNA controls from commercial vendors.

XNA-NGS Reduce the Sequencing Coverage to Achieve Required Sensitivity

Figure 9:
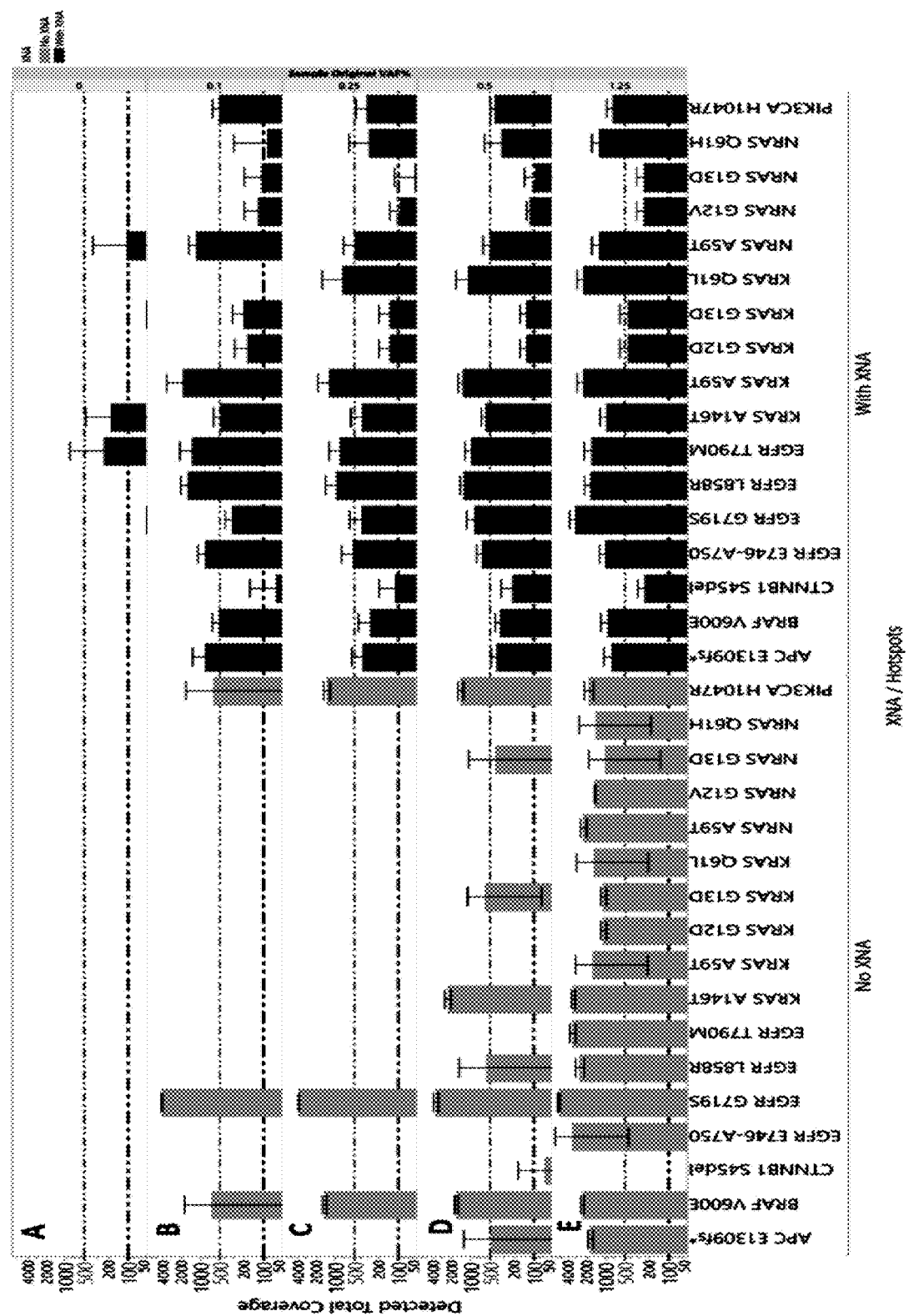
FIG. 9 illustrates the effects of XNA mix on total coverage using OPTISEQ™ Dual Cancer Panel.

Sufficient sequencing coverage is necessary to get reliable results for mutant detection. One of the concerns of using XNA for blocking wild type DNA amplification is that it may also eliminate amplicons for mutant detection. The total coverage of each locus after XNA enrichment PCR is displayed in FIG. 9 and Table 13, and Table 20 (Supplementary to Table 13). Average coverage per hotspot in reference standard gDNA mix samples containing 0.10%, 0.25%, 0.50% and 1.25% of mutants upon XNA enrichment were, 603x, 434x, 556x, and 1156x, respectively. Although the average total coverage of sample was relatively low compared to those without XNA, average variant number per hotspot gets boosted by 9.1×, 5.3×, 8.4×, and 10.9×, respectively after XNA enrichment in gDNA samples with original VAF % 0.10%, 0.25%, 0.50% and 1.25%. Hence, there is enough confidence to identify mutants 0.1% VAF even at relative lower coverage 500×. comparing to classic NGS (without XNA) needs 2000× coverage to achieve 1% sensitivity.

Effects of XNAs Mix Enhance NGS Mutation Reading Number

Figure 7A:
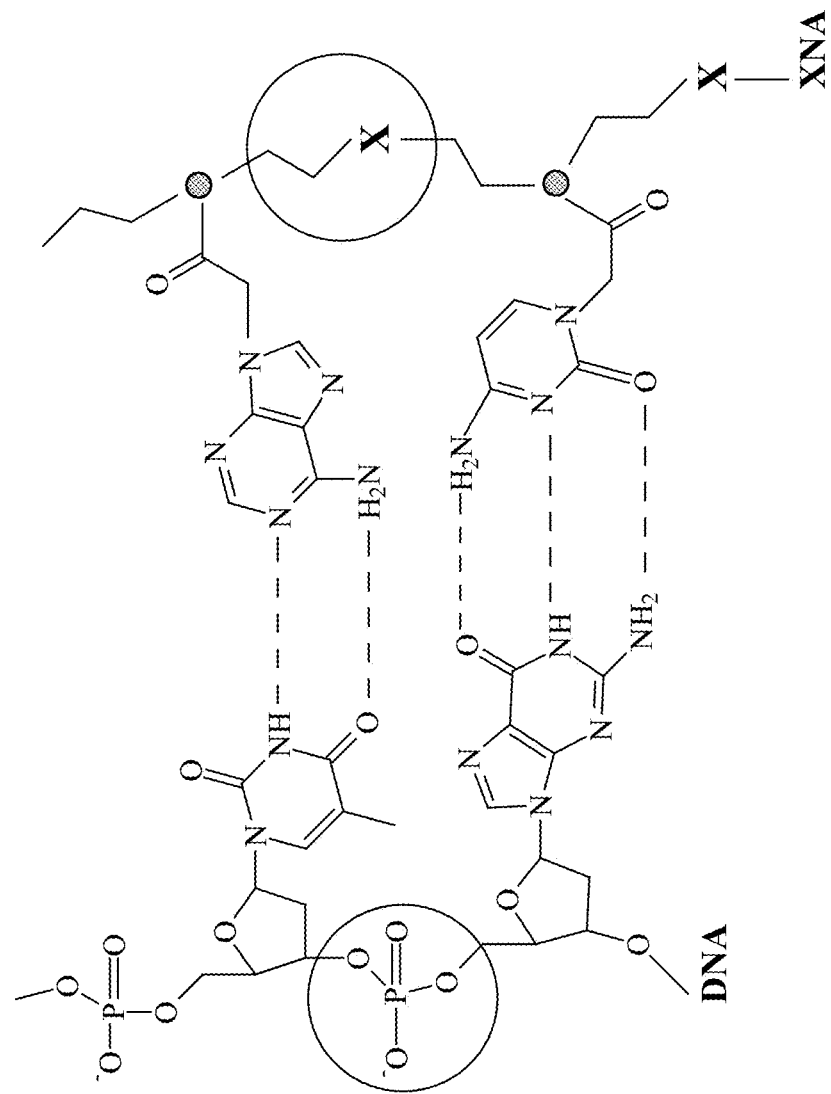
FIG. 7A. illustrates a Xenonucleic Acid (XNA) structure.
Figure 7B:
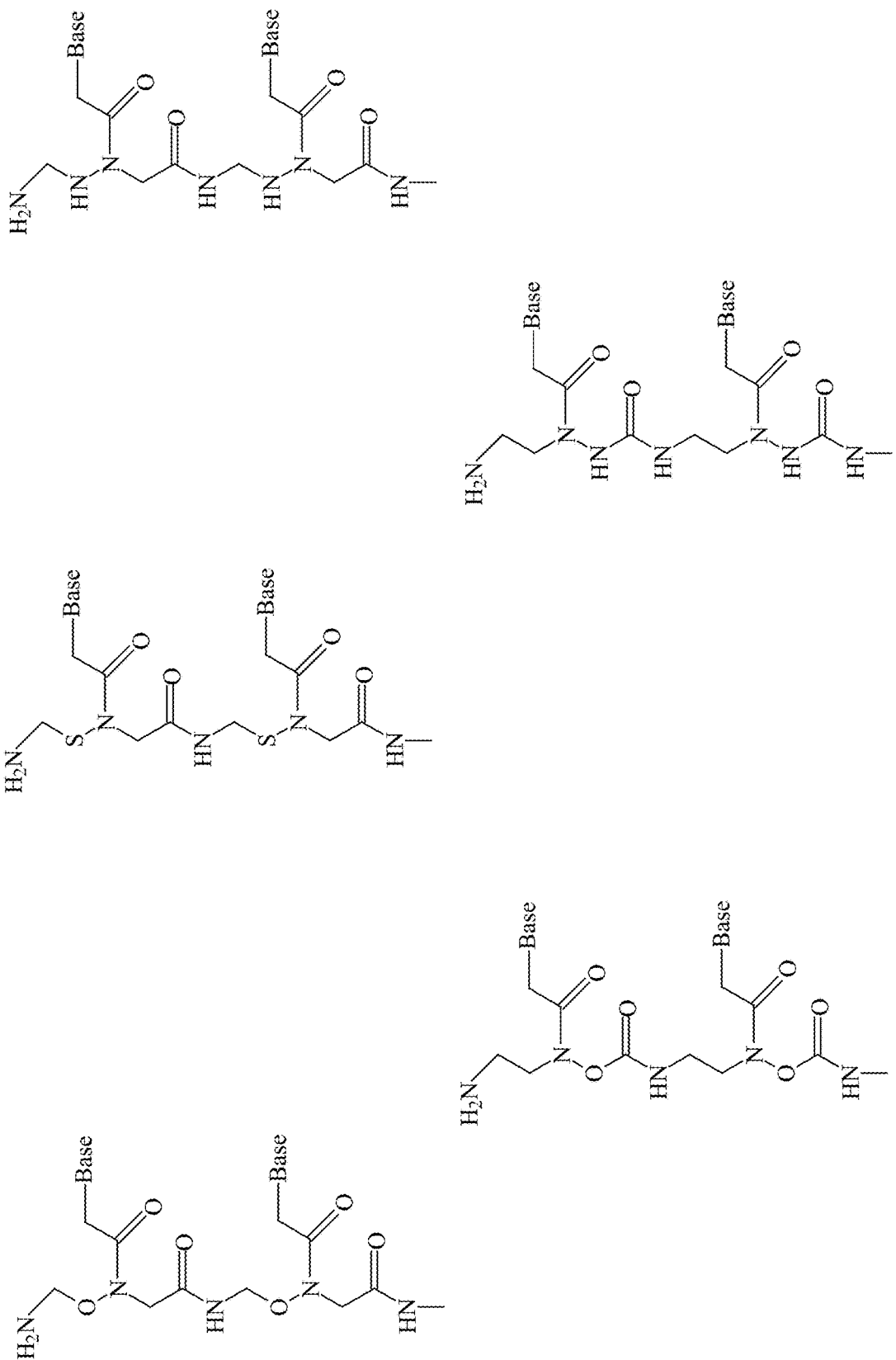
FIG. 7B shows preferred Xenonucleic acids having oxy-aza, aza-aza and sulfa-aza (thio-aza) bonding for use in the present invention.
Figure 7C:
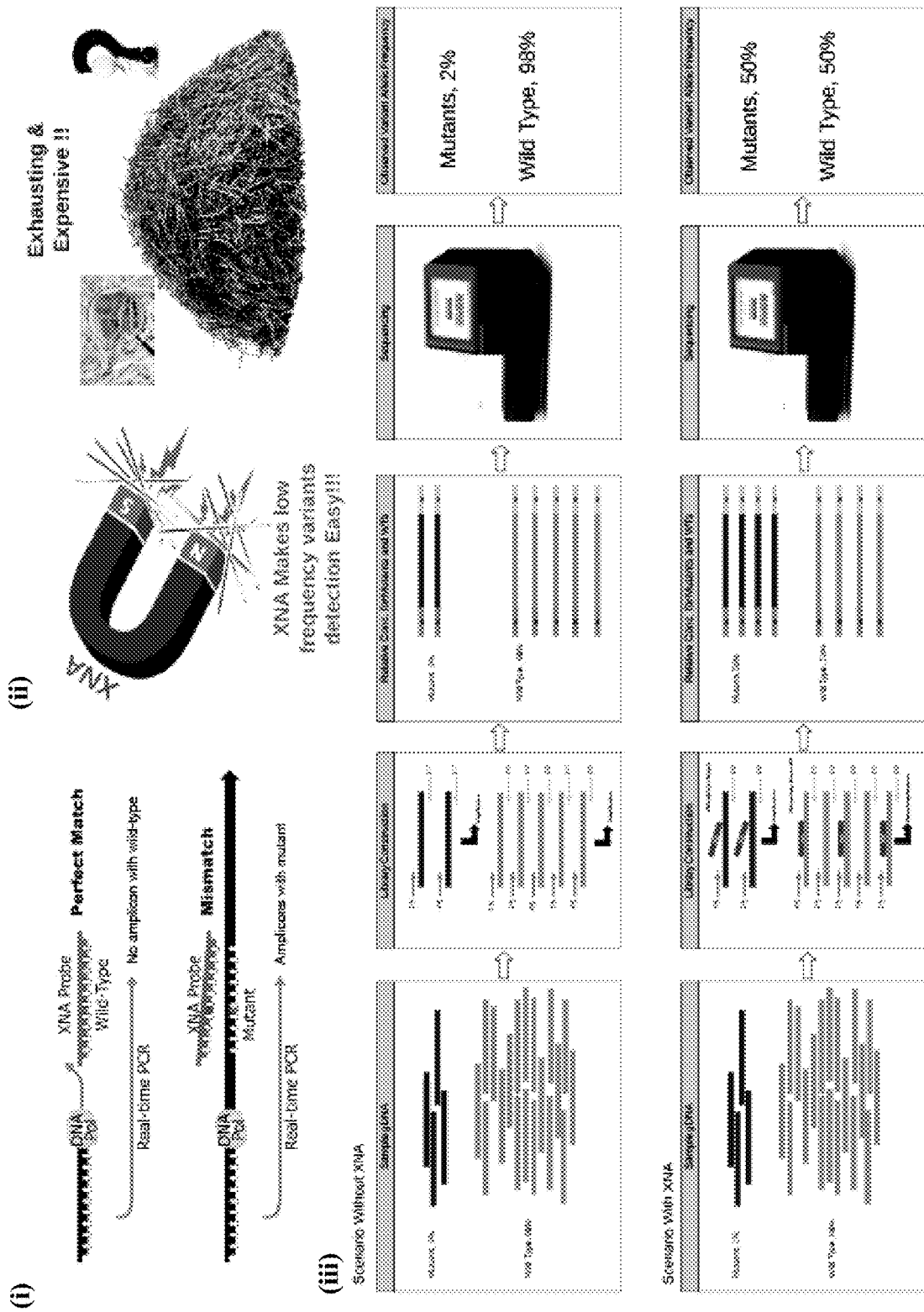
FIG. 7C illustrates the following: (i) the mechanism of XNA Molecular Clamp Technology, (ii) how XNA makes Low Frequency variant detection easy, and (iii) target enrichment for NGS analysis.

XNA is designed for blocking amplification of wild type DNA, which leads to increase of the percentage mutant DNA in amplified product. This mutant enrichment mechanism is illustrated in FIG. 7c. As a result, it is expected that more variants will be detected in library prepared after XNA enrichment than library prepared without XNA enrichment, on the same sample and in same number of reads.

Figure 10:
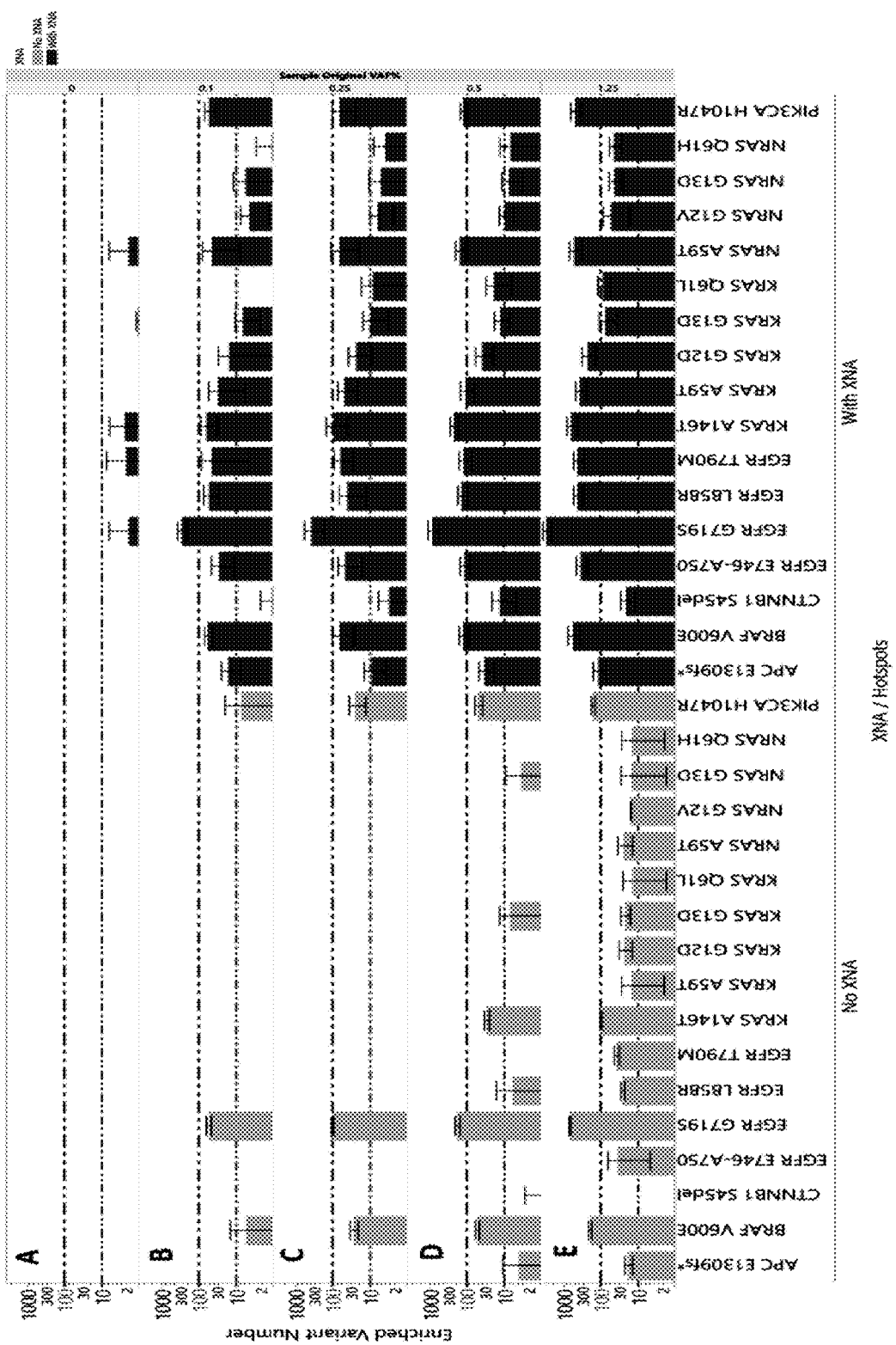
FIG. 10 shows the effects of XNA mix on variant number using OPTISEQ™ Dual Cancer Panel.

From FIG. 10, Table 13 and Table 20 (Supplementary to Table 13), on average, the NGS read number of mutants at each hotspot in samples with mutant VAF of 0.10% were 7 and 41, without or with XNA enrichment, respectively. Similarly, for samples with mutant VAF at 0.25%, 0.50%, and 1.25%, average number of NGS reads containing mutant alleles at each hotspot were 17 and 49, 33 (without XNA) and 125, and 83 and 443 with XNA enrichment, respectively, which results in 9.1, 5.3, 8.4, and 10.9 folds enrichment. This result demonstrated that XNA can selectively block amplification of wild type DNA, which leads to increase of VAF of mutants in amplified library.

Figure 11:
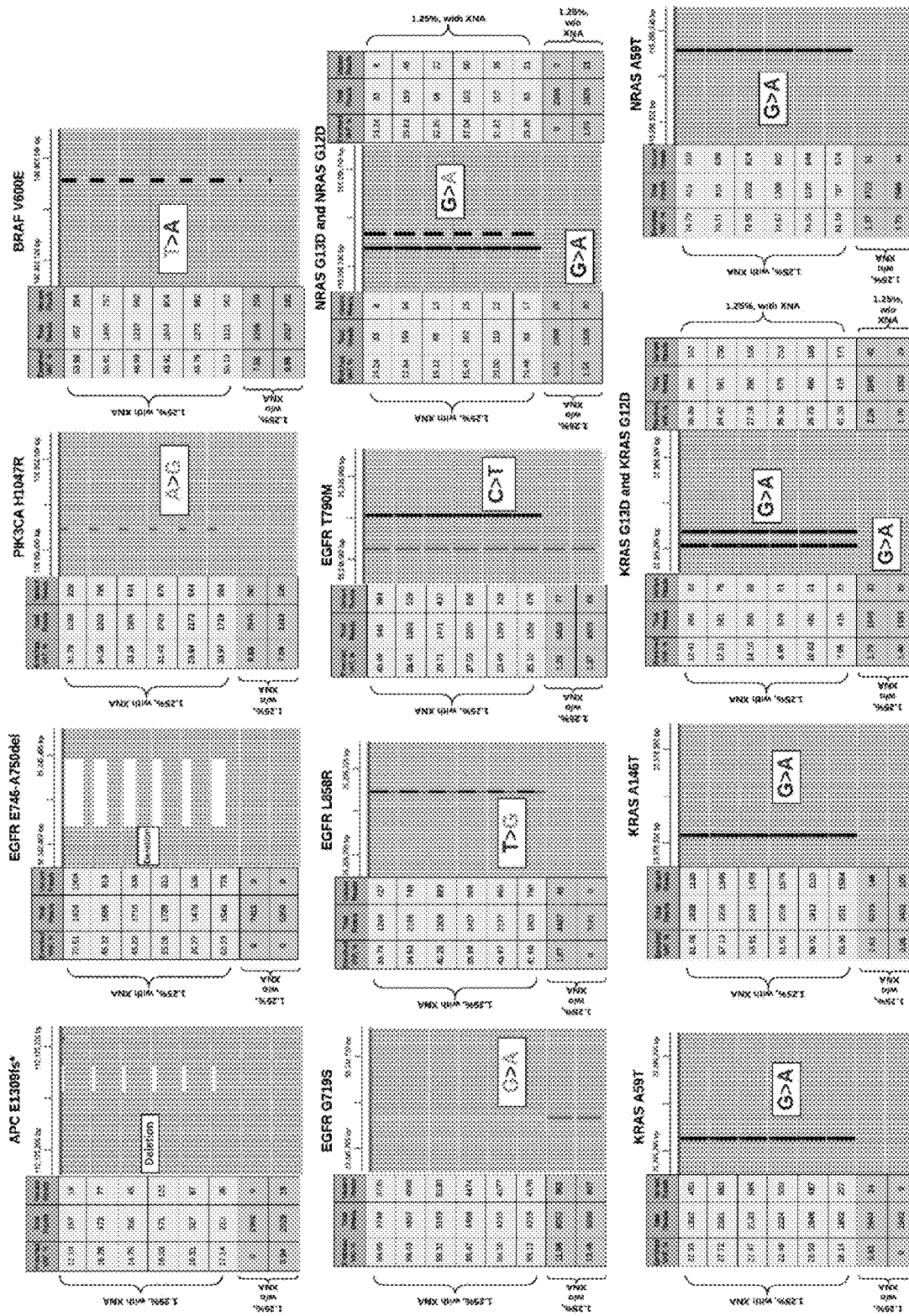
FIG. 11 features the effects of XNA mix on VAF enrichment and variant number using OPTISEQ™ Dual Cancer Panel.
Figure 12B:
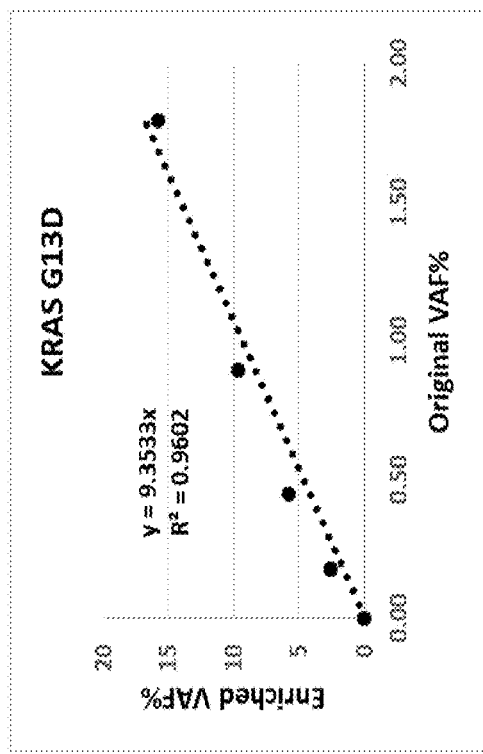
FIGS. 12A to 12P describes the correlation of Enriched VAF and original VAF 2.00%) with corresponding reggression equations.
Figure 12D:
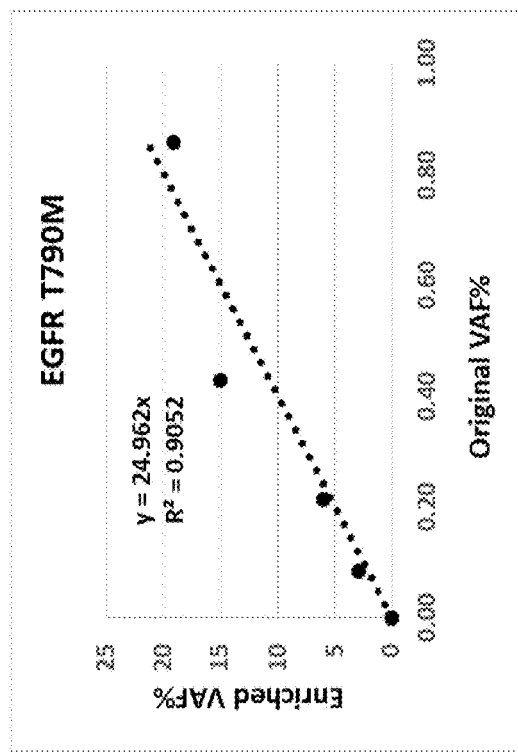
Figure 12A:
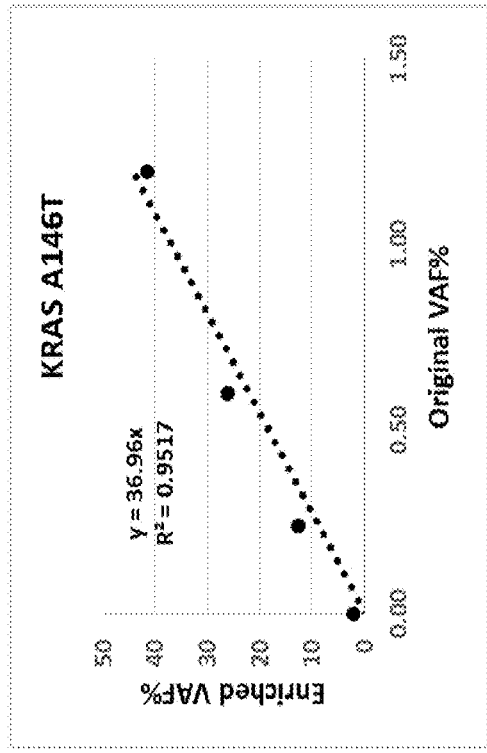
Figure 12C:
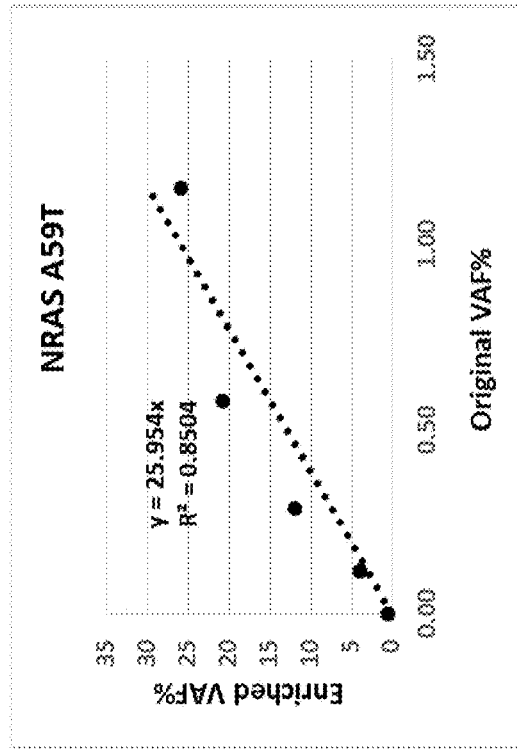
Figure 12E:
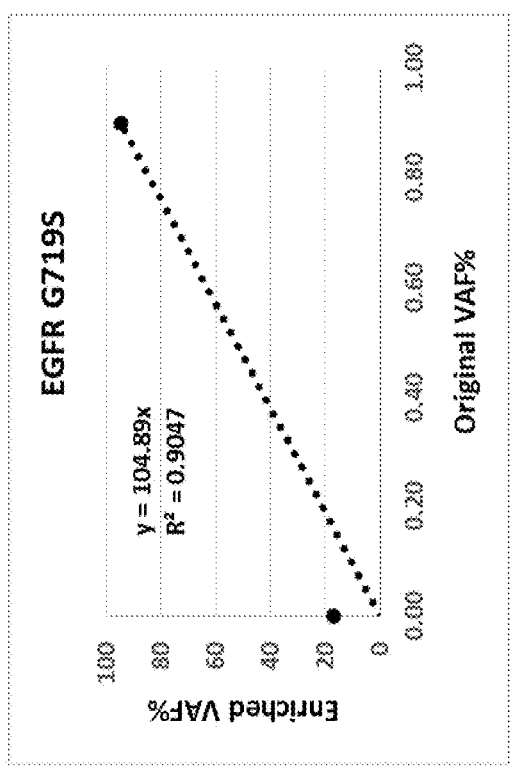
Figure 12F:
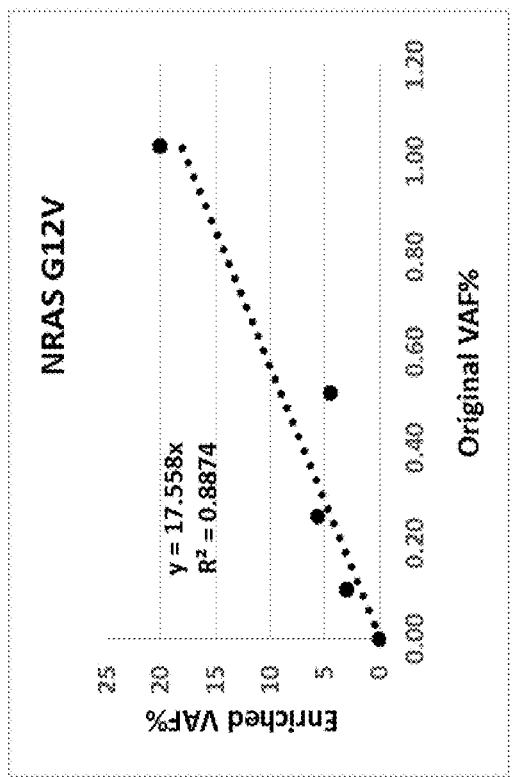
Figure 12G:
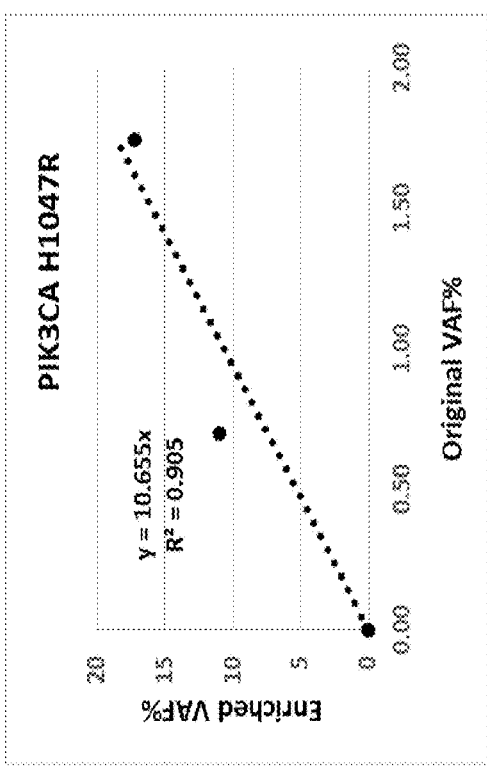
Figure 12H:
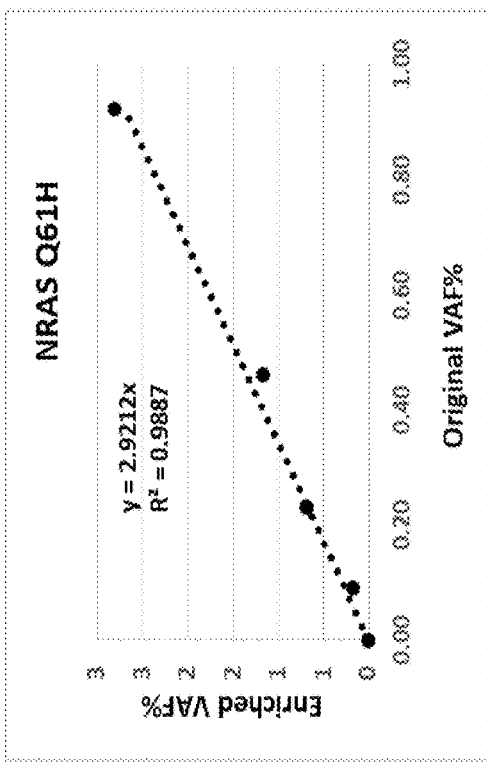
Figure 12I:
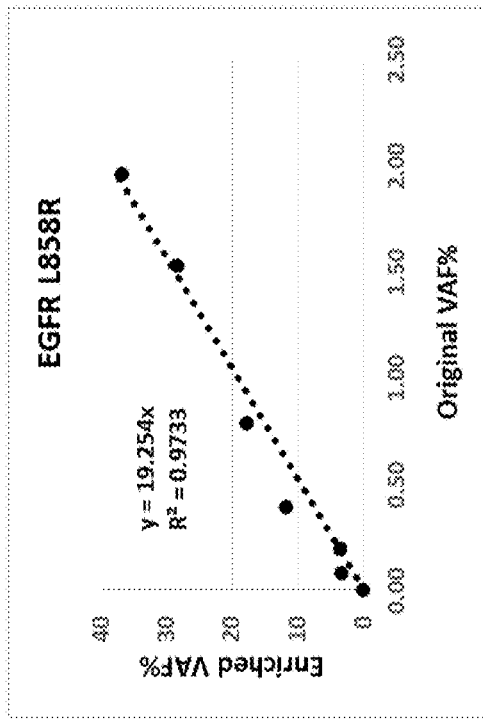
Figure 12J:
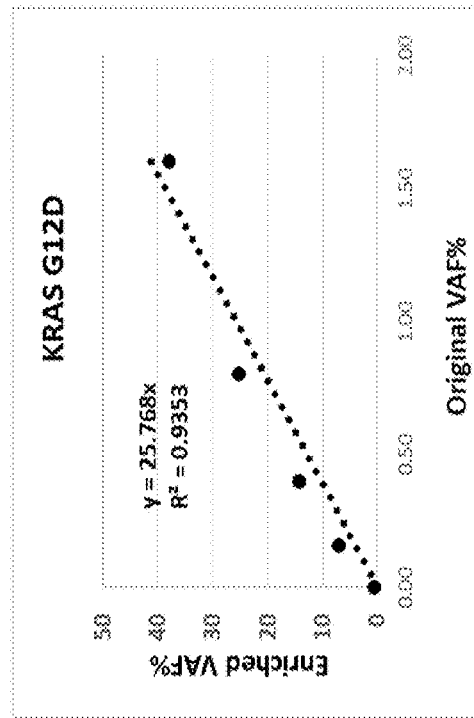
Figure 12K:
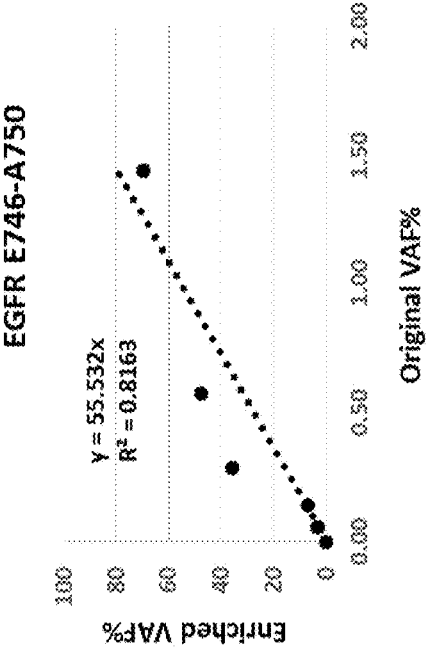
Figure 12L:
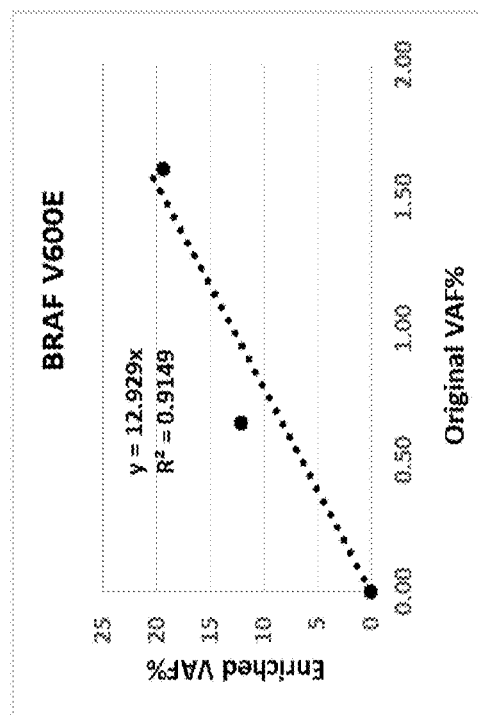
Figure 12M:
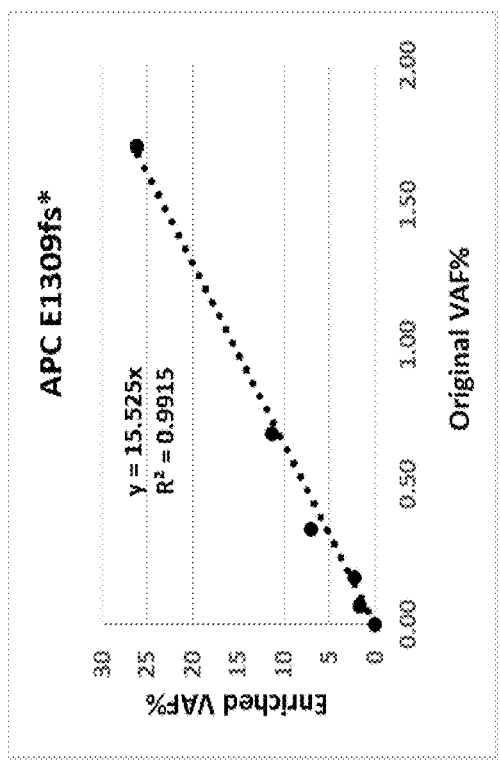
Figure 12N:
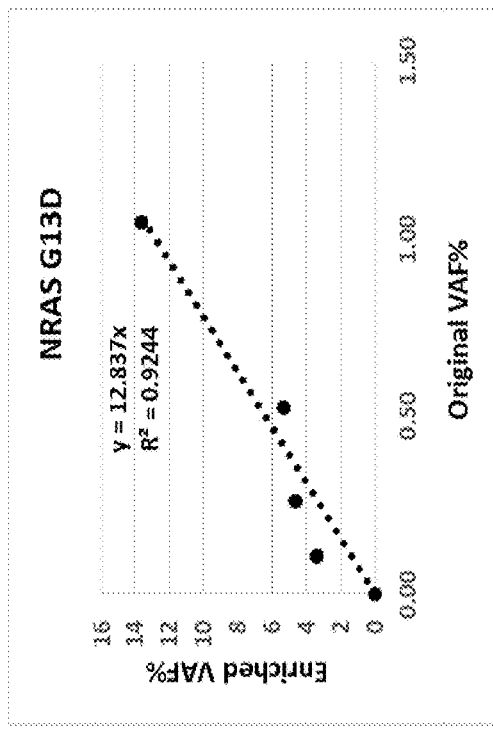
Figure 12O:
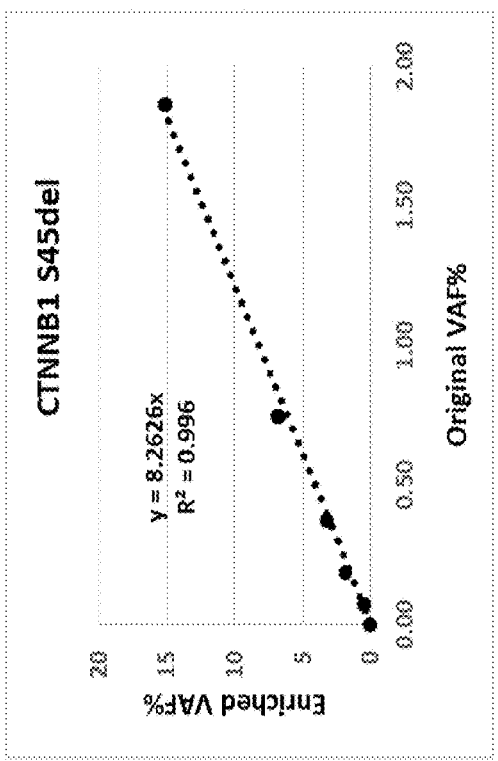
Figure 12P:
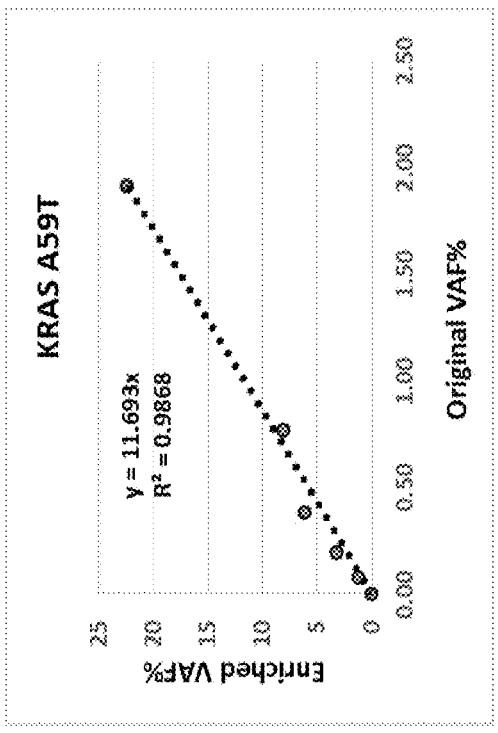

Detected VAF of 14 hotspots in gDNA reference standard samples with original VAF at 1.25% without or with XNA enrichment are shown in FIG. 11. There are 14 panels, each containing summary of analysis results of one mutant targeted by XNA. For instance, panel in column 1 (from left) and row 2 (from top) is a summary for "EGFR G719S" mutation. The table displayed on left side of the panel contains detected VAF %, total coverage, and variant number of EGFR G719S mutation. The IGV allele coverage plots (noise allele frequency cut off at 4%) on the right side of the panel contains 8 tracks, each from a single sample. The top six tracks are from 6 replicates in XNA enrichment experiment. The bottom two tracks are from two control experiments without XNA enrichment. The wild type reference and mutant alleles for "EGFR G719S" are G (Brown Color) and A (Green Color), respectively. They are shown as G>A in the inset of the plot. It is clear to see that XNA enrichment is specific to the targeted alleles in each amplicon and the effect of enrichment is very robust in all hotspots shown in the figure.

The Correlation of Enriched Variant Frequency (Enriched VAF) and Original Variant Frequency (Original VAF)

XNAs mix was spiked into the PCR reaction containing OptiSeq™ Dual Cancer Panel primer mix and human reference standard gDNA control samples containing mutants at different abundance levels. The estimated VAFs of 17 hotspots in human tumor samples were at 0.00%, 0.50%, 1.00%, 2.50%, 5.00%, 10.00% and 15.00% respectively, of which mutant copy number at 7 different frequency were 0, 17, 83, 167, 333, and 500 copies, respectively.

The average (Mean) variant allelic frequency (VAFs) with by Next Generation Sequencing, in present and absent of XNAs mix are summarized in Table 21 (Supplementary to Table 14)-A and Table 14-B. As expected, mutant detection powered by XNAs mix was dramatically boosted. To get the relationship between enriched VAF and original VAF of the sample, 17 graphs for 17 hotspots (Enriched VAF against Original VAF) were drafted in the FIG. 12 and S. FIG. 8. From the experiment results, we found out relationship between enriched VAF and original VAF tends to be linear when original VAF is less than 2.00%, while it tends to be polynomial with order 2 when original VAF is more than 2.00%. To get the regression model for each hotspot at different original VAF, we chose original VAF 2.00% as the cut-off value to fit the data less than 2.00% to the linear model, for data points with original VAF more than 2.00%, they were fitted to the polynomial with order 2 model. For example, KRAS A146T from FIG. 12, data on horizontal axis reflects original VAF (less than 2.00%), while those on vertical axis are enriched VAF. These data points fit in the regression equation y=36x with confidence $R^2$=0.9517. For the original VAF of KRAS A146T more than 2.00%, data points fit polynomial with order 2 equation y=−2.3889$x^2$+27.709x well with confidence $R^2$=0.9865. Regression equations of 17 hotspots were summarized in Table 22-A (Supplementary to Table 15) (Original VAF less than 2.00%) and Table 22-B (Original VAF more than 2.00%). 14 out of 17 hotspots (82.35%) achieved a high confidence level with $R^2$ more than 0.9 (Table 22-A), while 11 out of 17 hotspots (64.17%) with original VAF more than 2.00% achieved a high confidence level with $R^2$ more than 0.9 (Table 22-B), which gave us confidence to draw the conclusion that relationship between enriched VAF and original VAF less than 2.00% is linear, while those fit in polynomial with order 2 when original VAF is more than 2.00%.

On average, enriched VAF, original VAF, the number of mutants at each hotspot with original VAF at 6 variant allelic frequency at 0.50%, 1.00%, 2.50%, 5.00%, 10.00%, and 15.00% were summarized in Table 14-A (0.50%, 1.00%, and 2.50%) and Table 14-B (5.00%, 10.00%, and 15.00%). As expected, mutant detection powered by XNAs mix was dramatically boosted. Average enriched VAF for 17 hotspots were enriched by 48.8, 33.4, 12.5, 9.4, 6.8, and 5.0 folds compared to samples with estimated original VAF 0.50%, 1.00%, 2.50%, 5.00%, 10.00%, and 15.00%. Meanwhile, the average total coverage in presence or absence of XNAs mix were comparable. Enriched VAF in presence of XNAs mix ensures higher amount of detectable mutants in the sample. The results showed that average boost folds of mutant number in samples with original VAF 0.50%, 1.00%, 2.50%, 5.00%, 10.00%, and 15.00% are 9.8, 10.2, 5.5, 3.8, 3.8, and 4.8, respectively compared to samples without XNAs mix. This result further demonstrates that XNA can selectively block amplification of wild type DNA, which leads to increase of VAF of mutants in amplified library.

In samples containing 0.00% mutants or negative controls, the VAFs were either small or undetectable. The reason for detection of mutants in negative control in the presence of XNA is likely due to low level of DNA contamination from environment or some unknown mutations present in cell line DNA controls from commercial vendors.

Verification of XNA-Based Assay by FFPE Patient Samples 14 lung cancer FFPE samples and 10 colorectal cancer FFPE samples were applied to investigate the enriched effects of XNAs mix on real patient samples. Average detected VAF in presence and absence of XNAs mix were summarized in Table 15a (14 lung cancer FFPE samples and triplicate tests for each sample) and Table 15b (10 colorectal cancer FFPE samples, one replicate test for each sample). Detected mutations in patients' samples were compared against wild type healthy patient, the mutations detected in healthy people as well in presence of XNAs mix were filtered out in the patients' samples. For patient with ID 16A130, two mutations were detected by sequencing without XNAs mix, they are BRAF V600E (VAF=20.4%) and EGFR L858R (VAF=2.08%). After adding XNAs mix into the patient samples, 6 more mutations were detected (Table 15a). These 6 new mutations were not be able to be detected by normal sequencing method due to the super lower frequency of the samples. Meanwhile, the detected VAF of BRAF V600E increased to 77.17% from original VAF 20.4% and EGFR L858R of which increased from VAF 2.08% to 43.42% after adding XNAs mix. Due to the enriched VAF, mutant number of EGFR L858R increased to 116 from 79, while for the BRAF V600E, despite the enriched VAF, total coverage of loci BRAF V600 was only 242X with XNAs mix compared to that of patient without XNAs mix, that is 4807X, which resulted in decreased number of mutants after adding XNAs mix. Similar phenomena happened to the rest of 13 samples. Despite slight inconsistency with previous results of cell line genomic DNA samples, the overall boost folds of mutant number with XNAs mix is 1.33 times of those without XNAs mix, while the overall boost folds of VAF is 5.21 times of those without XNAs mix. For wild type control, we did not see any such mutants detectable. without XNA, the clinical assay sensitivity for lung cancer is about 86% (12/14 patients). With XNA, its clinical assay sensitivity for lung cancer is 100% (14/14 patients).

Similarly result was saw for colorectal cancer FFPE samples. From results in Table 15b, overall boost folds of mutant number with XNAs mix is 3.32 times of those without XNAs mix, while the overall boost folds of VAF is 4.40 times of those without XNAs mix. Clinical sensitivity for normal NGS is about 70% (7/10 patients). However, with XNA technology, clinical sensitivity is about 100% (10/10 patients). Wild type sample did not have any mutations detectable.

Verification of XNA-Based Assay with Cell Free DNA (cfDNA) Patient Samples 10 lung cancer cfDNA samples and 2 colorectal cancer cfDNA samples were applied to investigate the enriched effects of XNAs mix on real patient samples. Average detected VAF in presence and absence of XNAs mix were summarized in Table 16. The analysis criteria is the same with that of 6.1. One replicate was conducted for each experiment due to the limited amount of cfDNA. For most of the libraries, DNA inputs varied and were less than 10 ng, information of DNA input amount was included in the Table 10. The maximum DNA input for each library was 10 ng. The experiment results for both Lung cancer patient and colorectal cancer patient were included in single table (Table 10). Similar to results of FFPE samples, XNAs mix made mutation with low frequency detectable, at the same time, it enriched the VAF and increased mutant readable number in the sequencing pool. For example, patient ID D1729-B, the original VAF of EGFR L858R without XNA was 2.00%, while the enriched VAF was 40.37% after adding XNAs mix. Despite decreased total coverage from 3549 (without XNAs mix) to 379 (with XNAs mix), the mutant readable number increased to 153 from 71 after XNAs mix enrichment. Similar to Lung cancer cfDNA sample, colorectal cfDNA patients samples showed a similar results compared to those of lung cancer cfDNA. The overall boost folds of mutant number with XNAs mix is 1.10 times of those without XNAs mix, while the overall boost folds of VAF is 8.16 times of those without XNAs mix.

TABLE 13

Summary Table for the Effects of XNA mix on Detected Variant Allelic Frequency (VAF) and Coverage of sample using OptiSeq ™ Lung and Colorectal Cancer Mini Panel, 0.10% and 0.25%

| | Variant Allelic Frequency, 0.10% | | | | | | Variant Allelic Frequency, 0.25% | | | | | |
| --- | --- | --- | --- | --- | --- | --- | --- | --- | --- | --- | --- | --- |
| Hotspot Name | Frequency without XNA, % (Total Coverage) | # of Mutants without XNA | Frequency with XNA, % (Total Coverage) | # of Mutants with XNA | Mutant # Boost Folds | VAF Boost Folds | Frequency without XNA, % (Total Coverage) | # of Mutants without XNA | Frequency with XNA, % (Total Coverage) | # of Mutants with XNA | Mutant # Boost Folds | VAF Boost Folds |
| KRAS A146T | 0.25 (3324) | 8 | 12.68 (477) | 60 | 7 | 50.7 | 0.62 (3324) | 21 | 26.05 (377) | 98 | 5 | 42.0 |
| KRAS G13D | 0.16 (1098) | 2 | 2.59 (204) | 5 | 3 | 16.2 | 0.41 (1098) | 5 | 5.82 (136) | 8 | 2 | 14.2 |
| NRAS A59T | 0.08 (2288) | 2 | 3.89 (1176) | 46 | 25 | 48.6 | 0.21 (2288) | 5 | 11.94 (485) | 58 | 12 | 56.9 |
| EGFR T790M | 0.09 (3396) | 3 | 2.88 (1353) | 39 | 13 | 32.0 | 0.23 (3396) | 8 | 5.97 (849) | 51 | 6 | 26.0 |
| EGFR G719S | 1.01 (5624) | 57 | 94.43 (313) | 296 | 5 | 93.5 | 2.52 (5624) | 142 | 94.22 (386) | 364 | 3 | 37.4 |
| NRAS Q61H | 0.05 (1436) | 1 | 0.16 (87) | 0 | 0 | 3.2 | 0.14 (1436) | 2 | 0.68 (289) | 2 | 1 | 4.9 |
| NRAS G12V | 0.08 (1495) | 1 | 3.03 (119) | 4 | 3 | 37.9 | 0.21 (1495) | 3 | 5.6 (91) | 5 | 2 | 26.7 |
| PIK3CA H1047R | 0.71 (1879) | 13 | 10.98 (499) | 55 | 4 | 15.5 | 1.77 (1879) | 33 | 17.22 (312) | 54 | 2 | 9.7 |
| EGFR E746-A750 | 0.06 (3424) | 2 | 3.36 (845) | 28 | 14 | 56.0 | 0.14 (3424) | 5 | 7.03 (527) | 37 | 8 | 50.2 |
| EGFR L858R | 0.08 (2651) | 2 | 3.33 (1590) | 53 | 25 | 41.6 | 0.2 (2651) | 5 | 3.58 (966) | 35 | 7 | 17.9 |
| BRAF V600E | 0.68 (2356) | 16 | 12.04 (505) | 61 | 4 | 17.7 | 1.7 (2356) | 40 | 19.28 (278) | 54 | 1 | 11.3 |
| KRAS G12D | 0.17 (1099) | 2 | 6.98 (180) | 13 | 7 | 41.1 | 0.42 (1099) | 5 | 14.28 (136) | 19 | 4 | 34.0 |
| NRAS G13D | 0.08 (1012) | 1 | 3.35 (105) | 4 | 4 | 41.9 | 0.2 (1012) | 2 | 4.6 (54) | 2 | 1 | 23.0 |
| APC E1309fs* | 0.08 (1771) | 1 | 1.68 (845) | 14 | 10 | 21.0 | 0.21 (1771) | 4 | 2.09 (367) | 8 | 2 | 10.0 |
| KRAS A59T | 0.05 (1633) | 1 | 1.14 (1896) | 22 | 26 | 22.8 | 0.12 (1633) | 2 | 3.23 (1247) | 40 | 21 | 26.9 |

TABLE 13-continued

Summary Table for the Effects of XNA mix on Detected Variant Allelic Frequency (VAF) and Coverage of sample using OptiSeq ™ Lung and Colorectal Cancer Mini Panel, 0.10% and 0.25%

| | Variant Allelic Frequency, 0.10% | | | | | | Variant Allelic Frequency, 0.25% | | | | | |
|---|---|---|---|---|---|---|---|---|---|---|---|---|
| Hotspot Name | Frequency without XNA, % (Total Coverage) | # of Mutants without XNA | Frequency with XNA, % (Total Coverage) | # of Mutants with XNA | Mutant # Boost Folds | VAF Boost Folds | Frequency without XNA, % (Total Coverage) | # of Mutants without XNA | Frequency with XNA, % (Total Coverage) | # of Mutants with XNA | Mutant # Boost Folds | VAF Boost Folds |
| CTNNB1 S45del | 0.102 (65) | 0 | 0.45 (62) | 0 | 4 | 4.4 | 0.255 (65) | 0 | 1.85 (110) | 0 | 2 | 7.3 |
| KRAS Q61L | 0.05 (1564) | 1 | 0 (0) | 0 | 0 | 0.0 | 0.12 (1564) | 2 | 0.53 (772) | 4 | 2 | 4.4 |
| Average Total Coverage | 2121 | | 603 | | 9.1 | 32.0 | 2121 | | 434 | | 5.3 | 23.7 |

TABLE 14-A

Summary for the Effects of XNA mix on Detected Variant Allelic Frequency (VAF) and Coverage of sample using OptiSeq™ Lung and Colorectal Cancer Mini Panel, 0.50%, 1.00%, and 2.50%

| Hotspot Name | Variant Allelic Frequency, 0.50% | | | | | Variant Allelic Frequency, 1.00% | | | | | Variant Allelic Frequency, 2.50% | | | |
|---|---|---|---|---|---|---|---|---|---|---|---|---|---|---|
| | Frequency without XNA, % (Total Coverage) | # of Mutants without XNA | Frequency with XNA, % (Total Coverage) | # of Mutants with XNA | Mutant # Boost Folds | VAF Boost Folds | Frequency without XNA, % (Total Coverage) | # of Mutants without XNA | Frequency with XNA, % (Total Coverage) | # of Mutants with XNA | Mutant # Boost Folds | VAF Boost Folds | Frequency without XNA, % (Total Coverage) | # of Mutants without XNA | Frequency with XNA, % (Total Coverage) | # of Mutants with XNA | Mutant # Boost Folds | VAF Boost Folds |
| KRAS A146T | 1.04 (2267) | 29 | 41.52 (336) | 139 | 5 | 39.9 | 2.05 (2239) | 45 | 52.26 (377) | 198 | 4 | 25.5 | 5.99 (1845) | 111 | 81.22 (751) | 610 | 5 | 13.6 |
| KRAS G13D | 0.6 (616) | 7 | 9.59 (198) | 19 | 3 | 16.0 | 1.47 (1089) | 16 | 15.72 (301) | 46 | 3 | 10.7 | 4.49 (930) | 41 | 22.33 (478) | 106 | 3 | 5.0 |
| NRAS A59T | 0.17 (457) | 5 | 20.72 (625) | 131 | 26 | 121.9 | 0.77 (1520) | 14 | 25.89 (965) | 254 | 18 | 33.6 | 2.89 (1624) | 48 | 57.69 (1019) | 581 | 12 | 20.0 |
| EGFR T790M | 0.14 (603) | 5 | 15.04 (816) | 125 | 25 | 107.4 | 0.73 (1791) | 19 | 19.08 (1121) | 215 | 11 | 26.1 | 2.15 (2636) | 57 | 43.53 (1093) | 471 | 8 | 20.2 |
| EGFR G719S | 4.14 (3929) | 162 | 98.19 (574) | 563 | 3 | 23.7 | 9.54 (3373) | 328 | 98.93 (1274) | 1261 | 4 | 10.4 | 22.51 (3517) | 792 | 99.53 (2733) | 2720 | 3 | 4.4 |
| NRAS Q61H | 0 (0) | 0 | 1.16 (577) | 8 | N/A | N/A | 0.45 (1063) | 10 | 2.8 (966) | 27 | 3 | 6.2 | 2.31 (1624) | 38 | 5.69 (1022) | 61 | 2 | 2.5 |
| NRAS G12V | 0 (0) | 0 | 4.48 (153) | 6 | N/A | N/A | 0.3 (316) | 3 | 20.02 (187) | 39 | 13 | 66.7 | 2.58 (1099) | 29 | 24.93 (192) | 48 | 2 | 9.7 |
| PIK3CA H1047R | 2.82 (1849) | 53 | 5.29 (7052) | 376 | 7 | 1.9 | 6.11 (1404) | 86 | 13.9 (5804) | 723 | 8 | 2.3 | 17.49 (1214) | 212 | 30.01 (5776) | 1717 | 8 | 1.7 |
| EGFR E746-A750 | 0 (0) | 0 | 35.58 (178) | 65 | N/A | N/A | 0.29 (1327) | 12 | 47.85 (253) | 121 | 10 | 165.0 | 1.44 (3708) | 54 | 69.8 (352) | 246 | 5 | 48.5 |
| EGFR L858R | 0 (0) | 0 | 11.76 (891) | 101 | N/A | N/A | 0.55 (963) | 11 | 17.85 (1130) | 202 | 18 | 32.5 | 1.96 (1867) | 36 | 36.74 (1144) | 422 | 12 | 18.7 |
| BRAF V600E | 3.31 (2085) | 69 | 38.32 (345) | 132 | 2 | 11.6 | 6.44 (1815) | 118 | 52.92 (584) | 310 | 3 | 8.2 | 16.07 (2030) | 328 | 75.23 (814) | 613 | 2 | 4.7 |
| KRAS G12D | 0.31 (447) | 4 | 25.25 (197) | 51 | 13 | 81.5 | 1.28 (957) | 15 | 37.87 (299) | 114 | 8 | 29.6 | 4.02 (930) | 37 | 59.79 (477) | 288 | 8 | 14.9 |
| NRAS G13D | 0.15 (265) | 2 | 5.27 (129) | 9 | 5 | 35.1 | 0.52 (637) | 7 | 13.63 (187) | 25 | 4 | 26.2 | 2.61 (1098) | 28 | 25.09 (192) | 49 | 2 | 9.6 |
| APC E1309fs* | 0 (0) | 0 | 6.95 (397) | 31 | N/A | N/A | 0.23 (301) | 4 | 11.21 (609) | 67 | 17 | 48.7 | 1.71 (1452) | 25 | 26.03 (422) | 116 | 5 | 15.2 |
| KRAS A59T | 0 (0) | 0 | 6.09 (1695) | 101 | N/A | N/A | 0.27 (618) | 5 | 8.06 (1988) | 159 | 32 | 29.9 | 1.92 (1621) | 31 | 22.34 (1597) | 352 | 11 | 11.6 |
| CTNNB1 S45del | 0 (0) | 0 | 3.26 (89) | 4 | N/A | N/A | 0.51 (66) | 1 | 6.79 (114) | 8 | 8 | 13.3 | 1.86 (220) | 4 | 15.09 (90) | 14 | 4 | 8.1 |
| KRAS Q61L | 0 (0) | 0 | 1.28 (1696) | 22 | N/A | N/A | 0 (0) | 0 | 3.08 (1991) | 62 | N/A | N/A | 2.08 (1622) | 33 | 7.56 (1600) | 119 | 4 | 3.6 |
| Average Total Coverage | 736 | | 938 | | 9.8 | 48.8 | 1146 | | 1068 | | 10.2 | 33.4 | 1708 | | 1162 | | 5.5 | 12.5 |

TABLE 14-B

Summary for the Effects of XNA mix on Detected Variant Allelic Frequency (VAF) and Coverage of sample using OptiSeq™ Lung and Colorectal Cancer Mini Panel, 5.00%, 10.00%, and 15.00%

| Hotspot Name | Variant Allelic Frequency, 0.50% | | | | | Variant Allelic Frequency, 1.00% | | | | | Variant Allelic Frequency, 2.50% | | | | |
|---|---|---|---|---|---|---|---|---|---|---|---|---|---|---|---|
| | Frequency without XNA, % (Total Coverage) | # of Mutants without XNA | Frequency with XNA, % (Total Coverage) | # of Mutants with XNA | Mutant # Boost Folds | VAF Boost Folds | Frequency without XNA, % (Total Coverage) | # of Mutants without XNA | Frequency with XNA, % (Total Coverage) | # of Mutants with XNA | Mutant # Boost Folds | VAF Boost Folds | Frequency without XNA, % (Total Coverage) | # of Mutants without XNA | Frequency with XNA, % (Total Coverage) | # of Mutants with XNA | Mutant # Boost Folds | VAF Boost Folds |
| KRAS A146T | 3.19 (1226) | 39 | 64.13 (292) | 187 | 5 | 20.1 | 6.53 (1253) | 83 | 80.6 (445) | 358 | 4 | 12.3 | 6.53 (1539) | 100 | 76.8 (871) | 669 | 7 | 11.8 |
| KRAS G13D | 5.73 (777) | 44 | 10.17 (799) | 70 | 2 | 1.8 | 6.71 (1015) | 69 | 17.76 (380) | 67 | 1 | 2.6 | 12.72 (907) | 117 | 26.15 (685) | 179 | 2 | 2.1 |
| NRAS A59T | 7.87 (2333) | 182 | 84.13 (1549) | 1306 | 7 | 10.7 | 12.06 (1568) | 190 | 89.93 (1694) | 1523 | 8 | 7.5 | 20.29 (980) | 197 | 94.07 (2442) | 2296 | 12 | 4.6 |
| EGFR T790M | 3.06 (3836) | 122 | 59.22 (914) | 542 | 4 | 19.4 | 7.43 (2680) | 198 | 76.21 (1355) | 1026 | 5 | 10.3 | 15.31 (2535) | 388 | 83.45 (3538) | 2952 | 8 | 5.5 |
| EGFR G719S | 22.68 (4879) | 1108 | 99.51 (2181) | 2170 | 2 | 4.4 | 19.38 (2983) | 578 | 98.85 (1310) | 1304 | 2 | 5.1 | 11.28 (4571) | 517 | 90.81 (905) | 2952 | 2 | 8.1 |
| NRAS Q61H | 2.89 (2333) | 65 | 2.69 (1551) | 40 | 1 | 0.9 | 7.06 (1568) | 110 | 3.39 (1698) | 59 | 1 | 0.5 | 10.85 (980) | 106 | 2.83 (2446) | 69 | 1 | 0.3 |
| NRAS G12V | 3.93 (1756) | 68 | 40.57 (191) | 76 | 1 | 10.3 | 5.03 (1568) | 46 | 30.19 (166) | 50 | 1 | 6.0 | 9.47 (743) | 71 | 66.06 (130) | 86 | 1 | 7.0 |
| PIK3CA H1047R | 23.77 (1746) | 418 | 48.54 (4095) | 1702 | 4 | 2.0 | 39.28 (1588) | 621 | 53.11 (5120) | 2756 | 4 | 1.4 | 27.83 (1334) | 373 | 79.36 (1309) | 1023 | 3 | 2.9 |
| EGFR E746-A750 | 5.41 (4783) | 256 | 92.11 (850) | 786 | 3 | 17.0 | 6.76 (3185) | 214 | 91.07 (671) | 613 | 3 | 13.5 | 15.07 (4083) | 608 | 93.28 (1677) | 1583 | 3 | 6.2 |
| EGFR L858R | 1.53 (1480) | 22 | 28.31 (698) | 195 | 9 | 18.5 | 4.8 (1708) | 82 | 57.35 (1054) | 604 | 7 | 11.9 | 12.37 (1773) | 219 | 77.01 (2442) | 1884 | 9 | 6.2 |
| BRAF V600E | 6.06 (1584) | 96 | 45.17 (290) | 127 | 1 | 7.5 | 14.01 (1851) | 263 | 71.38 (442) | 316 | 1 | 5.1 | 55.13 (1683) | 928 | 95 (1596) | 1516 | 2 | 1.7 |
| KRAS G12D | 14.32 (776) | 112 | 83.72 (794) | 679 | 6 | 5.8 | 6.78 (1013) | 70 | 68.99 (378) | 263 | 4 | 10.2 | 10.21 (907) | 93 | 66.39 (683) | 454 | 5 | 6.5 |
| NRAS G13D | 4.02 (1757) | 70 | 23.46 (191) | 46 | 1 | 5.8 | 8.76 (920) | 81 | 40.83 (166) | 68 | 1 | 4.7 | 14.56 (825) | 122 | 79.98 (280) | 225 | 2 | 5.5 |
| APC E1309fis* | 5.07 (2120) | 107 | 55.23 (418) | 234 | 2 | 10.9 | 9.89 (1752) | 174 | 68.65 (492) | 329 | 2 | 6.9 | 11.77 (1363) | 160 | 55.75 (956) | 633 | 4 | 4.7 |
| KRAS A59T | 2.54 (1376) | 35 | 27.14 (1360) | 353 | 10 | 10.7 | 7.1 (1454) | 102 | 47.98 (1983) | 941 | 9 | 6.8 | 6.7 (1500) | 101 | 39.64 (3756) | 1484 | 15 | 5.9 |
| CTNNB1 S45del | 4.09 (339) | 13 | 41.72 (95) | 41 | 3 | 10.2 | 5.85 (92) | 5 | 54.71 (74) | 41 | 8 | 9.4 | 12.49 (90) | 11 | 55.2 (139) | 77 | 7 | 4.4 |
| KRAS Q61L | 2.56 (1376) | 36 | 7.97 (1360) | 108 | 3 | 3.1 | 18.63 (1453) | 271 | 25.96 (1987) | 521 | 2 | 1.4 | 29.76 (1500) | 450 | 38.61 (3760) | 1456 | 3 | 1.3 |
| Average Total Coverage | 2028 | | 1037 | | 3.8 | 9.4 | 1588 | | 1142 | | 3.8 | 6.8 | 1607 | | 1624 | | 4.8 | 5.0 |

TABLE 15a

Summary of 14 lung cancer FFPE patient detected VAF % and mutant number changes before and after adding XNA mix

| Patient ID | Hotspots | Frequency without XNA, % (Total Coverage) | # of Mutants without XNA | Frequency with XNA, % (Total Coverage) | # of Mutants with XNA | VAF Boost Folds | Mutant # Boost Folds |
|---|---|---|---|---|---|---|---|
| 16A129 | EGFR A750T | 0 (0) | 0 | 2.37 (440) | 10 | N/A | N/A |
| | EGFR P753L | 0 (0) | 0 | 3.53 (441) | 16 | N/A | N/A |
| | EGFR T790M | 0 (0) | 0 | 5.82 (1695) | 97 | N/A | N/A |
| | EGFR L858R | 86.9 (9432) | 8196 | 98.93 (28526) | 28219 | 1.14 | 3.44 |
| 16A130 | EGFR T790M | 0 (0) | 0 | 6.76 (297) | 21 | N/A | N/A |
| | EGFR L858R | 2.08 (3817) | 79 | 43.42 (267) | 116 | 20.88 | 1.47 |
| | KRAS S145* | 0 (0) | 0 | 4.5 (150) | 7 | N/A | N/A |
| | EGFR I744-L747del | 0 (0) | 0 | 1.73 (130) | 5 | N/A | N/A |
| | EGFR A859S | 0 (0) | 0 | 1.53 (131) | 4 | N/A | N/A |
| | BRAF R603Q | 0 (0) | 0 | 1.55 (113) | 4 | N/A | N/A |
| | BRAF V600E | 20.4 (4807) | 980 | 77.17 (242) | 187 | 3.78 | 0.19 |
| | BRAF R603* | 0 (0) | 0 | 3.86 (130) | 10 | N/A | N/A |
| 16A131 | EGFR T790M | 0 (0) | 0 | 5.36 (372) | 20 | N/A | N/A |
| | EGFR L858R | 0 (0) | 0 | 1.41 (125) | 4 | N/A | N/A |
| | EGFR G719S | 0 (0) | 0 | 49.18 (27) | 13 | N/A | N/A |
| | KRAS A146T | 0 (0) | 0 | 1.03 (98) | 2 | N/A | N/A |
| | BRAF V600E | 13.29 (3011) | 408 | 68.05 (279) | 189 | 5.12 | 0.46 |
| | NRAS G12D | 0 (0) | 0 | 8.62 (15) | 3 | N/A | N/A |
| | EGFR G857R | 0 (0) | 0 | 4.77 (225) | 11 | N/A | N/A |
| | EGFR L858M | 0 (0) | 0 | 1.02 (98) | 2 | N/A | N/A |
| | NRAS G13S | 0 (0) | 0 | 7.89 (19) | 3 | N/A | N/A |
| | APC E1309K | 0 (0) | 0 | 2.48 (71) | 4 | N/A | N/A |
| | APC I1311N | 0 (0) | 0 | 1.77 (71) | 3 | N/A | N/A |
| | BRAF T599K | 0 (0) | 0 | 1.25 (180) | 5 | N/A | N/A |
| 16A132 | EGFR T790M | 0 (0) | 0 | 9 (219) | 20 | N/A | N/A |
| | EGFR L858R | 0 (0) | 0 | 3.62 (69) | 5 | N/A | N/A |
| | NRAS L56Q | 0 (0) | 0 | 11.03 (34) | 4 | N/A | N/A |
| | EGFR G719S | 0 (0) | 0 | 35.71 (4) | 3 | N/A | N/A |
| | KRAS A146T | 0 (0) | 0 | 2.11 (71) | 3 | N/A | N/A |
| | KRAS T58L | 0 (0) | 0 | 2.05 (86) | 4 | N/A | N/A |
| | NRAS D57Y | 0 (0) | 0 | 13.1 (21) | 6 | N/A | N/A |
| | EGFR G746-A750del | 26.97 (2598) | 701 | 97.92 (2384) | 2333 | 3.63 | 3.33 |
| | KRAS V14I | 0 (0) | 0 | 15.79 (10) | 3 | N/A | N/A |
| | KRAS G12S | 0 (0) | 0 | 15.79 (10) | 3 | N/A | N/A |
| | EGFR G746* | 0 (0) | 0 | 1.61 (125) | 4 | N/A | N/A |
| | EGFR F856L | 0 (0) | 0 | 1.44 (70) | 2 | N/A | N/A |
| 16A133 | EGFR T790M | 0 (0) | 0 | 1.26 (198) | 5 | N/A | N/A |
| | BRAF c.1800G > T | 0 (0) | 0 | 9.92 (91) | 9 | N/A | N/A |
| | KRAS A146T | 0 (0) | 0 | 5.92 (167) | 9 | N/A | N/A |
| | APC G1312fs | 0 (0) | 0 | 1.74 (86) | 3 | N/A | N/A |
| | EGFR A859S | 0 (0) | 0 | 5.93 (68) | 8 | N/A | N/A |
| | KRAS G60D | 0 (0) | 0 | 2.28 (220) | 10 | N/A | N/A |
| | PIK3CA H1047Y | 0 (0) | 0 | 1.54 (818) | 12 | N/A | N/A |
| | BRAF L601fs | 0 (0) | 0 | 1.67 (60) | 2 | N/A | N/A |
| | KRAS S145fs | 0 (0) | 0 | 1.55 (113) | 4 | N/A | N/A |
| 16A134 | EGFR L858R | 51.02 (19) | 10 | 75 (3) | 2 | 1.47 | 0.20 |
| 16A135 | EGFR L858R | 20.53 (135) | 34 | 68.76 (27) | 19 | 3.35 | 0.56 |
| | EGFR K852R | 0 (0) | 0 | 20.24 (21) | 9 | N/A | N/A |
| 16A136 | EGFR G719A | 55.27 (160) | 89 | 100 (5) | 5 | 1.81 | 0.06 |
| | EGFR L858R | 0 (0) | 0 | 85 (11) | 9 | N/A | N/A |
| 16A137 | EGFR A750T | 0 (0) | 0 | 8.7 (23) | 4 | N/A | N/A |
| | EGFR A750E | 0 (0) | 0 | 5.43 (23) | 3 | N/A | N/A |
| | EGFR T790M | 0.49 (1186) | 12 | 6.17 (77) | 10 | 12.59 | 0.83 |
| | EGFR L858R | 1.03 (1557) | 16 | 6.16 (65) | 4 | 5.98 | 0.25 |
| | PIK3CA G1049D | 0 (0) | 0 | 2.5 (40) | 2 | N/A | N/A |
| | PIK3CA D1045G | 0 (0) | 0 | 4.38 (40) | 4 | N/A | N/A |
| | EGFR G746-T751del | 0 (0) | 0 | 4.35 (23) | 2 | N/A | N/A |
| 16A139 | EGFR A750T | 0 (0) | 0 | 1.75 (72) | 3 | N/A | N/A |
| | EGFR S752F | 0 (0) | 0 | 1.75 (72) | 3 | N/A | N/A |
| | EGFR P753L | 0 (0) | 0 | 3.42 (147) | 5 | N/A | N/A |
| | EGFR T790M | 0 (0) | 0 | 3.79 (192) | 15 | N/A | N/A |
| | EGFR L858R | 0 (0) | 0 | 1.11 (113) | 3 | N/A | N/A |
| | KRAS G60D | 0 (0) | 0 | 1.35 (259) | 7 | N/A | N/A |
| | NRAS D57Y | 0 (0) | 0 | 5.26 (38) | 4 | N/A | N/A |

TABLE 15a-continued

Summary of 14 lung cancer FFPE patient detected VAF % and mutant number changes before and after adding XNA mix

| Patient ID | Hotspots | Frequency without XNA, % (Total Coverage) | # of Mutants without XNA | Frequency with XNA, % (Total Coverage) | # of Mutants with XNA | VAF Boost Folds | Mutant # Boost Folds |
|---|---|---|---|---|---|---|---|
| 16A140 | EGFR L858R | 34.31 (560) | 191 | 83.76 (198) | 169 | 2.44 | 0.88 |
| | KRAS S145* | 0 (0) | 0 | 15.38 (7) | 2 | N/A | N/A |
| | EGFR c.2592G > A | 0 (0) | 0 | 6.86 (203) | 13 | N/A | N/A |
| | EGFR G857R | 0 (0) | 0 | 4.83 (88) | 9 | N/A | N/A |
| | EGFR L858W | 0 (0) | 0 | 5.4 (88) | 10 | N/A | N/A |
| | EGFR A864V | 0 (0) | 0 | 2.29 (88) | 4 | N/A | N/A |
| 16A141 | EGFR T790M | 0 (0) | 0 | 7.03 (139) | 11 | N/A | N/A |
| | EGFR G719S | 0 (0) | 0 | 18.18 (6) | 2 | N/A | N/A |
| | BRAF c.1800G > T | 0 (0) | 0 | 4.17 (48) | 4 | N/A | N/A |
| | KRAS S145* | 0 (0) | 0 | 6.05 (123) | 6 | N/A | N/A |
| | KRAS A146G | 0 (0) | 0 | 2.12 (95) | 4 | N/A | N/A |
| | PIK3CA H1047Y | 0 (0) | 0 | 1.09 (92) | 2 | N/A | N/A |
| | KRAS G13C | 14.41 (2267) | 327 | 43.08 (81) | 48 | 2.99 | 0.15 |
| 16A010 | EGFR G719D | 0 (0) | 0 | 7.41 (14) | 2 | N/A | N/A |
| | EGFR T790M | 0 (0) | 0 | 3.69 (741) | 27 | N/A | N/A |
| | EGFR c.2157C > T | 0 (0) | 0 | 15.1 (20) | 3 | N/A | N/A |
| | BRAF c.1800G > T | 0 (0) | 0 | 3.53 (281) | 10 | N/A | N/A |
| | KRAS A146T | 0 (0) | 0 | 2.53 (301) | 8 | N/A | N/A |
| | KRAS S145* | 0 (0) | 0 | 2.79 (301) | 9 | N/A | N/A |
| | EGFR G857R | 0 (0) | 0 | 1.12 (444) | 5 | N/A | N/A |
| | KRAS S145fs | 0 (0) | 0 | 1.05 (143) | 3 | N/A | N/A |
| | NRAS G60V | 0 (0) | 0 | 3.2 (155) | 5 | N/A | N/A |
| | APC S1315A | 0 (0) | 0 | 1.56 (129) | 4 | N/A | N/A |
| | BRAF V600L | 0 (0) | 0 | 1.11 (157) | 4 | N/A | N/A |
| | KRAS G13C | 0 (0) | 0 | 4.31 (29) | 3 | N/A | N/A |
| | NRAS G60Q | 0 (0) | 0 | 1.49 (67) | 2 | N/A | N/A |
| | APC T1313I | 0 (0) | 0 | 1.3 (115) | 3 | N/A | N/A |
| | EGFR G746_A750del | 30.5 (3995) | 1226 | 96.97 (6739) | 6543 | 3.18 | 5.34 |
| | BRAF S602C | 0 (0) | 0 | 2.15 (281) | 7 | N/A | N/A |
| | BRAF A598D | 0 (0) | 0 | 1.27 (157) | 4 | N/A | N/A |
| 16A011 | EGFR L858R | 20.37 (1753) | 374 | 91.91 (592) | 542 | 4.51 | 1.45 |
| | EGFR P753T | 0 (0) | 0 | 3.17 (32) | 2 | N/A | N/A |
| | NRAS A59G | 0 (0) | 0 | 10.75 (47) | 10 | N/A | N/A |
| | NRAS A59S | 0 (0) | 0 | 9.78 (46) | 9 | N/A | N/A |
| | KRAS G12D | 0 (0) | 0 | 22.73 (6) | 3 | N/A | N/A |
| Wild Type | All mutations | 0 (0) | 0 | 0 (0) | 0 | N/A | N/A |
| | Average VAF Boost Folds | | | | | 5.21 | 1.33 |

TABLE 15b

Summary of 10 Colon cancer FFPE patient detected VAF % and mutant number changes before and after adding XNA mix

| Patient ID | Hotspots | Frequency without XNA, % (Total Coverage) | # of Mutants without XNA | Frequency with XNA, % (Total Coverage) | # of Mutants with XNA | VAF Boost Folds | Mutant # Boost Folds |
|---|---|---|---|---|---|---|---|
| #7 | NRAS V14I | 0 (0) | 0 | 2.03 (493) | 10 | N/A | N/A |
| | PIK3CA A1046V | 0 (0) | 0 | 3.88 (103) | 4 | N/A | N/A |
| | PIK3CA H1047Y | 0 (0) | 0 | 11.76 (102) | 12 | N/A | N/A |
| | PIK3CA H1048Y | 0 (0) | 0 | 9.18 (98) | 9 | N/A | N/A |
| | APC G1312R | 0 (0) | 0 | 3.02 (398) | 12 | N/A | N/A |
| | EGFR T790M | 0 (0) | 0 | 2.79 (1004) | 28 | N/A | N/A |
| | EGFR G812R | 0 (0) | 0 | 4.58 (262) | 12 | N/A | N/A |
| | EGFR A859T | 0 (0) | 0 | 5.28 (265) | 14 | N/A | N/A |
| | BRAF K599E | 0 (0) | 0 | 2.56 (156) | 4 | N/A | N/A |

TABLE 15b-continued

Summary of 10 Colon cancer FFPE patient detected VAF % and mutant number changes before and after adding XNA mix

| Patient ID | Hotspots | Frequency without XNA, % (Total Coverage) | # of Mutants without XNA | Frequency with XNA, % (Total Coverage) | # of Mutants with XNA | VAF Boost Folds | Mutant # Boost Folds |
|---|---|---|---|---|---|---|---|
| | KRAS A59V | 0 (0) | 0 | 1.29 (1005) | 13 | N/A | N/A |
| | KRAS T58I | 0 (0) | 0 | 1.17 (1029) | 12 | N/A | N/A |
| | KRAS G13S | 0 (0) | 0 | 2.04 (442) | 9 | N/A | N/A |
| | KRAS G12S | 0 (0) | 0 | 1.36 (442) | 6 | N/A | N/A |
| | KRAS A11V | 0 (0) | 0 | 2.08 (432) | 9 | N/A | N/A |
| #41 | NRAS V14I | 0 (0) | 0 | 2.04 (392) | 8 | N/A | N/A |
| | PIK3CA A1046V | 0 (0) | 0 | 2.58 (892) | 23 | N/A | N/A |
| | APC G1312R | 0 (0) | 0 | 2.55 (314) | 8 | N/A | N/A |
| | EGFR T790M | 0 (0) | 0 | 4.23 (449) | 19 | N/A | N/A |
| | EGFR Q791* | 0 (0) | 0 | 3.52 (454) | 16 | N/A | N/A |
| | KRAS D57N | 0 (0) | 0 | 2.55 (706) | 18 | N/A | N/A |
| | KRAS G12S | 0 (0) | 0 | 6.35 (252) | 16 | N/A | N/A |
| | KRAS A11V | 0 (0) | 0 | 3.59 (251) | 9 | N/A | N/A |
| | NRAS G13D | 0 (0) | 0 | 2.95 (407) | 12 | N/A | N/A |
| | NRAS G13S | 0 (0) | 0 | 2.12 (378) | 8 | N/A | N/A |
| | APC R1314K | 0 (0) | 0 | 7.39 (284) | 21 | N/A | N/A |
| | EGFR A859D | 0 (0) | 0 | 1.96 (153) | 3 | N/A | N/A |
| | BRAF c.1800G > A | 0 (0) | 0 | 7.14 (140) | 10 | N/A | N/A |
| | KRAS A146S | 0 (0) | 0 | 1.72 (232) | 4 | N/A | N/A |
| | KRAS G60S | 0 (0) | 0 | 3.16 (697) | 22 | N/A | N/A |
| | KRAS A59T | 0 (0) | 0 | 2.49 (723) | 18 | N/A | N/A |
| | KRAS G13D | 0 (0) | 0 | 2.87 (244) | 7 | N/A | N/A |
| #73 | EGFR T790M | 0 (0) | 0 | 3.71 (1160) | 43 | N/A | N/A |
| | PIK3CA G1050D | 0 (0) | 0 | 1.4 (429) | 6 | N/A | N/A |
| | EGFR T751K | 0 (0) | 0 | 3.07 (163) | 5 | N/A | N/A |
| | KRAS G12V | 27 (963) | 260 | 72.43 (1614) | 1169 | 3 | 4 |
| #81 | EGFR T790M | 0 (0) | 0 | 2.02 (940) | 19 | N/A | N/A |
| | KRAS D57N | 0 (0) | 0 | 3.36 (982) | 33 | N/A | N/A |
| | APC R1314K | 0 (0) | 0 | 3.07 (261) | 8 | N/A | N/A |
| | KRAS G12V | 26.79 (922) | 247 | 91.44 (1880) | 1719 | 3 | 7 |
| #99 | EGFR P753T | 0 (0) | 0 | 1.73 (173) | 3 | N/A | N/A |
| | EGFR T790M | 0 (0) | 0 | 1.76 (1023) | 18 | N/A | N/A |
| | BRAF c.1800G > A | 0 (0) | 0 | 1.45 (275) | 4 | N/A | N/A |
| | KRAS A146S | 0 (0) | 0 | 1.26 (397) | 5 | N/A | N/A |
| | EGFR T751K | 0 (0) | 0 | 1.66 (181) | 3 | N/A | N/A |
| | APC Q1311fs | 29.66 (2788) | 827 | 73.66 (911) | 671 | 2 | 1 |
| | BRAF S602C | 0 (0) | 0 | 1.44 (277) | 4 | N/A | N/A |
| | KRAS A146G | 0 (0) | 0 | 1.28 (390) | 5 | N/A | N/A |
| #104 | EGFR Q791* | 0 (0) | 0 | 3.89 (180) | 7 | N/A | N/A |
| | KRAS T58I | 0 (0) | 0 | 2.55 (275) | 7 | N/A | N/A |
| | KRAS D57N | 0 (0) | 0 | 2.24 (268) | 6 | N/A | N/A |
| | PIK3CA H1047R | 15.99 (2357) | 377 | 39.38 (480) | 189 | 2 | 1 |
| | BRAF V600E | 11.05 (1900) | 210 | 61.45 (83) | 51 | 6 | 0 |
| #116 | EGFR G857E | 0 (0) | 0 | 6.74 (89) | 6 | N/A | N/A |
| | KRAS D57N | 0 (0) | 0 | 2.48 (323) | 8 | N/A | N/A |
| | KRAS G13D | 12.85 (996) | 128 | 80.51 (508) | 409 | 6 | 3 |
| #138 | PIK3CA H1047Y | 1.28 (2424) | 31 | 11.58 (1304) | 151 | 9 | 5 |
| | KRAS D57N | 0 (0) | 0 | 3.53 (935) | 33 | N/A | N/A |
| | KRAS G12S | 27.28 (1338) | 365 | 89.68 (2239) | 2008 | 3 | 6 |
| | EGFR A750T | 0 (0) | 0 | 5.97 (134) | 8 | N/A | N/A |
| #150 | EGFR T790M | 0 (0) | 0 | 2.05 (1124) | 23 | N/A | N/A |
| | BRAF R603Q | 0 (0) | 0 | 1.4 (214) | 3 | N/A | N/A |
| #152 | EGFR T790M | 0 (0) | 0 | 2.42 (496) | 12 | N/A | N/A |
| | EGFR Q791* | 0 (0) | 0 | 1.79 (502) | 9 | N/A | N/A |
| | EGFR G857R | 0 (0) | 0 | 3.2 (125) | 4 | N/A | N/A |
| | KRAS D57N | 0 (0) | 0 | 1.12 (538) | 6 | N/A | N/A |
| | KRAS G13D | 0 (0) | 0 | 10 (140) | 14 | N/A | N/A |
| Wild Type | All Mutations | 0 (0) | 0 | 0 (0) | 0 | N/A | N/A |
| Average VAF Boost Folds | | 4.4 | | 3.32 | | | |

TABLE 16

Summary of Lung and Colon cancer cfDNA patient detected VAF % and mutant number changes before and after adding XNA mix

| Cancer Type | Patient ID | DNA Input, ng | Hotspots | Frequency without XNA, %(Total Coverage) | # of Mutants without XNA | Frequency with XNA, % (Total Coverage) | # of Mutants with XNA | VAF Boost Folds | Mutant # Boost Folds |
|---|---|---|---|---|---|---|---|---|---|
| Lung Cancer | D1811-B | 3.9 | NRAS T58S | 0 (0) | 0 | 2.15 (419) | 9 | N/A | N/A |
| | | | NRAS c.36T > C | 0 (0) | 0 | 3.2 (281) | 9 | N/A | N/A |
| | | | CTNNB1 c.132T > A | 0 (0) | 0 | 1.32 (227) | 3 | N/A | N/A |
| | | | EGFR L718Q | 0 (0) | 0 | 3.87 (155) | 6 | N/A | N/A |
| | | | EGFR G719D | 0 (0) | 0 | 1.3 (154) | 2 | N/A | N/A |
| | | | EGFR P753Q | 0 (0) | 0 | 1.71 (175) | 3 | N/A | N/A |
| | | | EGFR F856L | 0 (0) | 0 | 1.13 (796) | 9 | N/A | N/A |
| | | | KRAS Q61fs | 0 (0) | 0 | 1.12 (534) | 6 | N/A | N/A |
| | | | KRAS G12V | 5.16 (310) | 16 | 60.38 (106) | 64 | 11.70 | 4.00 |
| Lung Cancer | D1779-B | 10.0 | EGFR G719D | 0 (0) | 0 | 4.2 (119) | 5 | N/A | N/A |
| | | | KRAS G12V | 0 (0) | 0 | 3.52 (199) | 7 | N/A | N/A |
| | | | EGFR G719D | 0 (0) | 0 | 2.52 (119) | 3 | N/A | N/A |
| | | | EGFR c.2157C > T | 0 (0) | 0 | 5.93 (118) | 7 | N/A | N/A |
| | | | EGFR A750T | 0 (0) | 0 | 1.62 (431) | 7 | N/A | N/A |
| | | | EGFR S752P | 0 (0) | 0 | 1.86 (430) | 8 | N/A | N/A |
| Lung Cancer | D1738-B | 3.9 | EGFR G719D | 10.4 (11946) | 1242 | 98.19 (2381) | 2338 | 9.44 | 1.88 |
| | | | NRAS G13S | 0 (0) | 0 | 2.37 (253) | 6 | N/A | N/A |
| | | | PIK3CA c.3135T > C | 0 (0) | 0 | 2.55 (274) | 7 | N/A | N/A |
| | | | PIK3CA c.3138A > T | 0 (0) | 0 | 2.93 (273) | 8 | N/A | N/A |
| | | | EGFR T790A | 0 (0) | 0 | 1.01 (1778) | 18 | N/A | N/A |
| | | | BRAF K601E | 0 (0) | 0 | 1.27 (473) | 6 | N/A | N/A |
| | | | KRAS A146T | 0 (0) | 0 | 4.33 (231) | 10 | N/A | N/A |
| | | | KRAS D57N | 0 (0) | 0 | 1.32 (2343) | 31 | N/A | N/A |
| Lung Cancer | D1729-B | 6.0 | NRAS G60E | 0 (0) | 0 | 9.09 (55) | 5 | N/A | N/A |
| | | | NRAS G60R | 0 (0) | 0 | 12.73 (55) | 7 | N/A | N/A |
| | | | APC I1311T | 0 (0) | 0 | 3.32 (211) | 7 | N/A | N/A |
| | | | APC T1313A | 0 (0) | 0 | 5.19 (212) | 11 | N/A | N/A |
| | | | APC S1315P | 0 (0) | 0 | 2.84 (211) | 6 | N/A | N/A |
| | | | EGFR L858R | 2 (3549) | 71 | 40.37 (379) | 153 | 20.19 | 2.15 |
| Lung Cancer | D1689-B | 4.1 | NRAS G60E | 0 (0) | 0 | 4.7 (447) | 21 | N/A | N/A |
| | | | NRAS G60R | 0 (0) | 0 | 2.46 (447) | 11 | N/A | N/A |
| | | | APC K1310R | 0 (0) | 0 | 2.01 (1197) | 24 | N/A | N/A |
| | | | EGFR | 0 (0) | 0 | 2.75 (218) | 6 | N/A | N/A |
| | | | EGFR c.2231T > C | 0 (0) | 0 | 2.44 (614) | 15 | N/A | N/A |
| Lung Cancer | D1685-B | 8.2 | NRAS T58S | 0 (0) | 0 | 1.43 (838) | 12 | N/A | N/A |
| | | | KRAS G12V | 0 (0) | 0 | 4.07 (270) | 11 | N/A | N/A |

TABLE 16-continued

Summary of Lung and Colon cancer cfDNA patient detected VAF % and mutant number changes before and after adding XNA mix

| Cancer Type | Patient ID | DNA Input, ng | Hotspots | Frequency without XNA, %(Total Coverage) | # of Mutants without XNA | Frequency with XNA, % (Total Coverage) | # of Mutants with XNA | VAF Boost Folds | Mutant # Boost Folds |
|---|---|---|---|---|---|---|---|---|---|
| | | | EGFR A750T | 0 (0) | 0 | 1.94 (515) | 10 | N/A | N/A |
| | | | EGFR P753T | 0 (0) | 0 | 2.53 (514) | 13 | N/A | N/A |
| | | | EGFR L858R | 14.29 (4067) | 581 | 86.83 (4511) | 3917 | 6.08 | 6.74 |
| | | | EGFR c.2256T > A | 0 (0) | 0 | 1.17 (515) | 6 | N/A | N/A |
| | | | NRAS I55M | 0 (0) | 0 | 1.31 (838) | 11 | N/A | N/A |
| | | | EGFR E749K | 0 (0) | 0 | 1.17 (515) | 6 | N/A | N/A |
| | | | BRAF S602F | 0 (0) | 0 | 1.42 (564) | 8 | N/A | N/A |
| Lung Cancer | D1768-D | 3.5 | EGFR L858R | 28.07 (3666) | 1029 | 89.78 (2134) | 1916 | 3.20 | 1.86 |
| | | | BRAF c.1800G > A | 0 (0) | 0 | 16.08 (199) | 32 | N/A | N/A |
| | | | PIK3CA H1047R | 0 (0) | 0 | 2.66 (864) | 23 | N/A | N/A |
| | | | PIK3CA D1047G | 0 (0) | 0 | 1.62 (863) | 14 | N/A | N/A |
| | | | APC K1308E | 0 (0) | 0 | 1.19 (336) | 4 | N/A | N/A |
| | | | APC R1314T | 0 (0) | 0 | 1.17 (341) | 4 | N/A | N/A |
| Lung Cancer | D1743-B | 3.4 | EGFR L718Q | 0 (0) | 0 | 1.5 (133) | 2 | N/A | N/A |
| | | | APC K1310E | 0 (0) | 0 | 1.63 (551) | 9 | N/A | N/A |
| | | | EGFR T751A | 0 (0) | 0 | 2.14 (887) | 19 | N/A | N/A |
| | | | BRAF V600E | 0 (0) | 0 | 7.98 (163) | 13 | N/A | N/A |
| | | | EGFR c.2148A > G | 0 (0) | 0 | 11.94 (134) | 16 | N/A | N/A |
| | | | EGFR L747P | 72.98 (9948) | 7260 | 86.4 (890) | 769 | 1.18 | 0.11 |
| | | | KRAS c.177A > G | 0 (0) | 0 | 1.92 (834) | 16 | N/A | N/A |
| | | | KRAS G13D | 0 (0) | 0 | 10.81 (74) | 8 | N/A | N/A |
| Lung Cancer | D1734-B | 3.3 | NRAS T58S | 0 (0) | 0 | 1.92 (156) | 3 | N/A | N/A |
| | | | EGFR P753T | 0 (0) | 0 | 5.18 (193) | 10 | N/A | N/A |
| | | | EGFR L858R | 16.81 (5837) | 981 | 89.34 (2290) | 2046 | 5.31 | 2.09 |
| | | | NRAS Q61R | 0 (0) | 0 | 4.49 (156) | 7 | N/A | N/A |
| | | | NRAS A59V | 0 (0) | 0 | 7.69 (156) | 12 | N/A | N/A |
| Lung Cancer | D1732-B | 3.592 | APC C.3936A > G | 0 (0) | 0 | 2.05 (830) | 17 | N/A | N/A |
| | | | BRAF S602F | 0 (0) | 0 | 1.57 (191) | 3 | N/A | N/A |
| | | | EGFR T751A | 0 (0) | 0 | 2.5 (160) | 4 | N/A | N/A |
| | | | KRAS c.438A > G | 0 (0) | 0 | 5.08 (118) | 6 | N/A | N/A |
| | | | NRAS c.168G > A | 0 (0) | 0 | 8.65 (185) | 16 | N/A | N/A |
| | | | PIK3CA c.3144 T > C | 0 (0) | 0 | 1.41 (1559) | 22 | N/A | N/A |
| | | | APC S1315L | 0 (0) | 0 | 1.57 (828) | 13 | N/A | N/A |
| | | | EGFR c.2235G > A | 0 (0) | 0 | 1.09 (3022) | 33 | N/A | N/A |
| | | | EGFR c.2571G > A | 0 (0) | 0 | 1.16 (344) | 4 | N/A | N/A |
| | | | BRAF S602P | 0 (0) | 0 | 9.95 (191) | 19 | N/A | N/A |

TABLE 16-continued

Summary of Lung and Colon cancer cfDNA patient detected VAF % and mutant number changes before and after adding XNA mix

| Cancer Type | Patient ID | DNA Input, ng | Hotspots | Frequency without XNA, %(Total Coverage) | # of Mutants without XNA | Frequency with XNA, % (Total Coverage) | # of Mutants with XNA | VAF Boost Folds | Mutant # Boost Folds |
|---|---|---|---|---|---|---|---|---|---|
| Colon Cancer | D1175-B | 7.8 | NRAS T58S | 0 (0) | 0 | 2.45 (408) | 10 | N/A | N/A |
| | | | BRAF K601E | 0 (0) | 0 | 1.91 (314) | 6 | N/A | N/A |
| | | | KRAS D57N | 0 (0) | 0 | 1.11 (1986) | 22 | N/A | N/A |
| | | | NRAS T58I | 0 (0) | 0 | 1.71 (409) | 7 | N/A | N/A |
| | | | EGFR S720P | 0 (0) | 0 | 6.38 (47) | 3 | N/A | N/A |
| | | | EGFR L858fs | 0 (0) | 0 | 1.61 (372) | 6 | N/A | N/A |
| | | | KRAS G12S | 0 (0) | 0 | 6.12 (147) | 9 | N/A | N/A |
| Colon Cancer | D1022-B | 3.6 | EGFR G857R | 0 (0) | 0 | 5.1 (471) | 24 | N/A | N/A |
| | | | EGFR c.2152C > T | 0 (0) | 0 | 2.94 (102) | 3 | N/A | N/A |
| | | | EGFR A750V | 0 (0) | 0 | 4.22 (166) | 7 | N/A | N/A |
| | | | BRAF c.1791A > T | 0 (0) | 0 | 1.01 (298) | 3 | N/A | N/A |
| | | | KRAS Q61* | 0 (0) | 0 | 1.56 (1922) | 30 | N/A | N/A |
| Wild Type | Healthy People | 5 | All mutations | 0 (0) | 0 | 0 (0) | 0 | N/A | N/A |
| | | | Average VAF Boost Folds | | | | | 8.16 | 1.10 |

TABLE 17

Comparison between calculated enriched VAF and detected enriched VAF by using regression equations

| Sample Type | Cancer Type | Patient ID | Hotpots | Original VAF % (No XNA) | Calculated enriched VAF % (With XNA) | Enriched VAF % (With XNA) | Error, % | Equation | $R^2$ |
|---|---|---|---|---|---|---|---|---|---|
| FFPE | Lung Cancer | 16A130 | EGFR L858R | 2.1 | 50.3 | 43.3 | 16.0 | $y = 2.5996x + 44.863$ | 1 |
| | | | BRAF V600E | 20.4 | 85.0 | 77.2 | 10.1 | $y = -0.0464x^2 + 3.7915x + 26.927$ | 0.9901 |
| FFPE | Lung Cancer | 16A131 | BRAF V600E | 13.3 | 69.1 | 68.1 | 1.6 | $y = -0.0464x^2 + 3.7915x + 26.927$ | 0.9901 |
| FFPE | Lung Cancer | 16A137 | EGFR T790M | 0.5 | 12.2 | 6.2 | 98.2 | $y = 24.962x$ | 0.9052 |
| | | | EGFR L858R | 1.0 | 19.8 | 6.2 | 221.9 | $y = 19.254x$ | 0.9733 |
| FFPE | Colorectal Cancer | #104 | PIK3CA H1047R | 16.0 | 40.1 | 39.4 | 1.7 | $y = -0.0641x^2 + 4.3557x - 13.199$ | 0.8138 |
| | | | BRAF V600E | 11.1 | 63.2 | 61.5 | 2.8 | $y = -0.0464x^2 + 3.7915x + 26.927$ | 0.9901 |
| FFPE | Colorectal Cancer | #138 | PIK3CA H1047Y | 1.28 | 13.7 | 11.58 | 17.9 | $y = 10.655x$ | 0.905 |
| cfDNA | Lung Cancer | D1811-B | KRAS G12V | 5.16 | 62.5 | 60.38 | 3.4 | $y = 0.1551x^2 - 0.817x + 62.541$ | 0.8543 |
| cfDNA | Lung Cancer | D1738-B | EGFR G719D | 10.4 | 95.4 | 98.19 | 2.8 | $y = 0.0222x^2 - 0.3879x + 97.06$ | 0.3157 |
| cfDNA | Lung Cancer | D1729-B | EGFR L858R | 2 | 38.5 | 40.37 | 4.6 | $y = 19.254x$ | 0.9733 |
| | | | Average standard error rate, % | | | | 34.7 | | |
| | | | Average standard error rate, % exclude sample 16A137 | | | | 6.8 | | |

For the mutations detected and listed in Table 15a, Table 15b and Table 16, they are more than 17 hotspots as we discussed before. Since XNA only show a higher blocking effects towards wild type sequence. Any mutant happened in this range will lead to loose affinity of the template, thus facilitating the amplification of the mutants. Hence, all loci covered by 13 XNAs were included in these two Tables. The information of covered range of 13 XNAs were summarized in Table 20 (Supplementary to Table 13).

Although we use some FFPE and cfDNA patients' samples to verify the enrichment effects of XNAs mix on samples with low variant frequency, it is critical to get the real/original VAF in patient, that can be utilized by clinical professional as the criterion to make insight judgement of the patient disease. Particularly for patients with super low VAF that can't be detected by normal NGS method. Meanwhile, this variant is critically related to specific cancer disease. To verify these regression equations, VAF from patient sample with/without XNAs mix were evaluated by NGS method. We applied regression equations to get calculated enriched VAF and compared them with enriched VAF from NGS method. The resulted were summarized in Table 17. Original VAF of all mutations listed in Table 16 fell into confidence interval range (x). For those falling out of this range, they were excluded from this table. For example, patient ID 16A130 on the first raw of Table 17, there are two mutations detected by NGS for both with XNAs mix and without XNAs mix conditions. VAF of EGFR L858R was 2.1% without XNA enrichment, 43.3% after XNA enrichment. Since the original VAF was more than 2.0% cut-off value, regression equation $y=2.5996x+44.863$ was applied to get the calculated enriched VAF, the result was 50.3%. Standard error was 16.0% compared to detected enriched VAF. The average standard error of 11 mutations were 34.7%. There was one sample with two mutations that had a comparable higher standard error rate, they are EGFR T790M and EGFR L858R from sample 16A137. If excluding this sample, average standard error for 9 mutations will be decreased to 6.8%. This result demonstrated that regression equations got from cell-line genomic DNA are reliable and can be utilized to deduced original VAF of patient samples.

TABLE 18

Mutations summary and corresponding drug therapy and related diseases

| Gene | Mutation Type | Nucleotide Change | Amino Acid Change | FDA Approved Therapies for Indication | Related Diseases |
|---|---|---|---|---|---|
| APC | Deletion | c.3921_3925 delAAAAG | p.Glu1309fs | N/A | Rectal cancers, Colon cancers, Melanomas, Colorectal adenomas |
| BRAF | SNV | c.1799T > A | p.Val600Glu | 5-fluorouracil, Bevacizumab, Aflibercept, 5-fluoropyrimidine, Regorafenib, Tipiracil, Trifluridine, 5-fluorouracil, Bevacizumab, Trametinib, Cobimetinib, BRAF inhibitor, MEK, Ipilimumab, BRAF inhibitor, Sorafenib, Cobimetinib, Dabrafenib, Nivolumab, Dabrafenib, Vemurafenib | Metastatic colorectal cancer, Non-squamous non-small cell lung cancer, Metastatic renal cell carcinoma, Cervical cancer, Peritoneal Cancer, Metastatic melanoma |
| CTNNB1 | Deletion | c.131_133del CTT | p.Ser45del | Crizotinib | Metastatic nonsmall cell lung cancer, Liver Cancers, Endometrial Cancers, Renal Cancers |
| EGFR | Deletion | c.2235_2249 del GGAATTA AGAGAAGC | p.Glu746_Ala 750del | Tyrosine kinase, Bevacizumab, Carboplatin, Erlotinib, Carboplatin, Cetuximab, Panitumumab, Vandetanib, Bosutinib, Lapatinib, Brigatinib, Necitumumab, Pembrolizumab, Afatinib, Cetuximab, EGFR TKIs, Cetuximab, Cisplatin, Erlotinib, Osimertinib, Gefitinib, Afatinib | Metastatic colorectal cancer, Non-squamous non-small cell lung cancer, Metastatic renal cell carcinoma, Cervical cancer, Peritoneal cancer, Endometrial, Ovarian, Head, neck cancers, Symptomatic or progressive medullary thyroid cancer, Advanced or metastatic breast cancer |
| EGFR | SNV | c.2155G > A | p.Gly719Ser | Bevacizumab, Carboplatin, Erlotinib, Carboplatin, Panitumumab, Vandetanib, Bosutinib, Lapatinib, Brigatinib, Necitumumab, Tyrosine kinase, Pembrolizumab, Afatinib, Cetuximab, EGFR TKIs, Cetuximab, Cisplatin, Erlotinib, | Metastatic colorectal cancer, Non-squamous non-small cell lung cancer, Metastatic renal cell carcinoma, Cervical cancer, Peritoneal cancer, Endometrial, Ovarian, Head, neck cancers, Symptomatic or progressive medullary thyroid cancer, Advanced |

TABLE 18-continued

Mutations summary and corresponding drug therapy and related diseases

| Gene | Mutation Type | Nucleotide Change | Amino Acid Change | FDA Approved Therapies for Indication | Related Diseases |
|---|---|---|---|---|---|
| EGFR | SNV | c.2573T > G | p.Leu858Arg | Osimertinib, Gefitinib, Afatinib Bevacizumab, Carboplatin, Erlotinib, Carboplatin, Cetuximab, Panitumumab, Vandetanib, Bosutinib, Lapatinib, Brigatinib, Necitumumab, Tyrosine kinase, Pembrolizumab, Afatinib, Cetuximab, EGFR TKIs, Cetuximab, Cisplatin, Erlotinib, Osimertinib, Gefitinib, Afatinib | or metastatic breast cancer Metastatic colorectal cancer, Non-squamous non-small cell lung cancer, Metastatic renal cell carcinoma, Cervical cancer, Peritoneal cancer, Endometrial, Ovarian, and Head and neck cancers, Symptomatic or progressive medullary thyroid cancer, Advanced or metastatic breast cancer |
| EGFR | SNV | c.2369C > T | p.Thr790Met | Bevacizumab, Carboplatin, Erlotinib, Carboplatin, Cetuximab, Brigatinib, Tyrosine kinase, Pembrolizumab, Afatinib, Cetuximab, EGFR TKIs, Cetuximab, Cisplatin, Erlotinib, Osimertinib, Gefitinib, Afatinib | Metastatic colorectal cancer, Non-squamous non-small cell lung cancer, Metastatic renal cell carcinoma, Cervical cancer, Peritoneal cancer, Endometrial, Ovarian, and head and neck cancers |
| KRAS | SNV | c.436G > A | p.Ala146Thr | Carboplatin, Erlotinib, Paclitaxel, Bevacizumab, Fluoropyrimidine, 5-fluorouracil, Irinotecan, Leucovorin, Ramucirumab, Bevacizumab, 5-fluorouracil, Irinotecan, Leucovorin, Oxaliplatin | Metastatic colorectal cancer, Endometrial, Ovarian, and head and neck cancers, Metastatic renal cell carcinoma, Cervical cancer |
| KRAS | SNV | c.175G > A | p.Ala59Thr | Panitumumab, Cetuximab | Metastatic colorectal cancer |
| KRAS | SNV | c.35G > A | p.Gly12Asp | 5-fluorouracil, Bevacizumab, Aflibercept, 5-fluoropyrimidine, Regorafenib, Tipiracil, Trifluridine, 5-fluorouracil, Bevacizumab, Carboplatin, Erlotinib, Carboplatin, Cetuximab, Panitumumab | Metastatic colorectal cancer, Non-squamous non-small cell lung cancer, Metastatic renal cell carcinoma, Cervical cancer, Peritoneal cancer, Endometrial, ovarian, and head and neck cancers |
| KRAS | SNV | c.38G > A | p.Gly13Asp | Regorafenib, 5-fluorouracil, Carboplatin, Erlotinib, Bevacizumab, Fluoropyrimidine, Tipiracil, Trifluridine, Aflibercept, 5-fluorouracil, Carboplatin, Bevacizumab, Panitumumab, Cetuximab, Irinotecan, Cetuximab, Erlotinib, Vinorelbine, Cisplatin, Platinum, Cetuximab, Chemother, EGFR tyrosine kinase, Carboplatin, Erlotinib, Irinotecan, Panitumu, Carboplatin, Paclitaxel, Panitumumab, Cetuximab | Metastatic colorectal cancer, Endometrial, Ovarian, and head and neck cancers, Non-small cell lung cancer, Metastatic testicular tumor, Metastatic ovarian tumor |
| KRAS | SNV | c.182A > T | p.Gln61Leu | Gefitinib, Erlotinib, Ektorinib, Cetuximad, Panitumumad, Nimotuzumab | Intestine cancer, Lung cancer, Pancreas cancer, Haematopoietic, lymphoid cancer and skin cancer |
| NRAS | SNV | c.175G > A | p.Ala59Thr | 5-fluorouracil, Bevacizumab, Aflibercept, 5-fluoropyrimidine, | Metastatic colorectal cancer, Non-squamous non-small cell lung cancer, Metastatic renal |

TABLE 18-continued

Mutations summary and corresponding drug therapy and related diseases

| Gene | Mutation Type | Nucleotide Change | Amino Acid Change | FDA Approved Therapies for Indication | Related Diseases |
|---|---|---|---|---|---|
| | | | | Regorafenib, Tipiracil, Trifluridine, 5-fluorouracil, Bevacizumab | cell carcinoma, Cervical cancer, Peritoneal cancer |
| NRAS | SNV | c.35G > T | p.Gly12Val | Cetuximad, Panitumumad | Colorectal Cancer |
| NRAS | SNV | c.38G > A | p.Gly13Asp | Cetuximad, Panitumumad | Colorectal Cancer |
| NRAS | SNV | c.183A > T | p.Gln61His | 5-fluorouracil, Bevacizumab, Aflibercept, 5-fluoropyrimidine, Regorafenib, Tipiracil, Trifluridine, 5-fluorouracil, Bevacizumab | Metastatic colorectal cancer, Non-squamous non-small cell lung cancer, Metastatic renal cell carcinoma, Cervical cancer, Peritoneal cancer |
| PIK3CA | SNV | c.3140A > G | p.His1047Arg | N/A | Unresectable or metastatic melanoma, Nonsmall cell lung cancer, Unresectable or metastatic pancreatic cancer |

TABLE 19

Primer sequences and corresponding hotspots covered information

| Primer Pair Name | Fwd primer | Rev primer | Covered Hotspots |
|---|---|---|---|
| DCNP001 | SEQ ID NO: 220 CCTACACGACGCTCTTCCGATCTAGCAAC AGTCTTACCTGGACT | SEQ ID NO: 221 TTCAGACGTGTGCTCTTCCGATCTGGGA GGTATCCACATCCTCTTC | CTNNB1 S45 |
| DCNP002 | SEQ ID NO: 222 CCTACACGACGCTCTTCCGATCTGTATTT ATTTCAGTGTTACTTACCTGTCTTGT | SEQ ID NO: 223 TTCAGACGTGTGCTCTTCCGATCTAAGA TGTACCTATGGTCCTAGTAGGA | KRAS A146 |
| DCNP003 | SEQ ID NO: 224 CCTACACGACGCTCTTCCGATCTCCTGTA GAGGTTAATATCCGCAAATG | SEQ ID NO: 225 TTCAGACGTGTGCTCTTCCGATCTGTTA TAGATGGTGAAACCTGTTTGTTG | NRAS A59, NRAS Q61 |
| DCNP004 | SEQ ID NO: 226 CCTACACGACGCTCTTCCGATCTTGGGAT CATATTCATCTACAAAGTGGTT | SEQ ID NO: 227 TTCAGACGTGTGCTCTTCCGATCTTAC TGGTTTCCAACAGGTTCTTG | NRAS G12, NRAS G13 |
| DCNP005 | SEQ ID NO: 228 CCTACACGACGCTCTTCCGATCTCTCTGG AATGCCAGAACTACAAT | SEQ ID NO: 229 TTCAGACGTGTGCTCTTCCGATCTGTGG AAGATCCAATCCATTTTGTTG | PIK3CA H1047 |
| DCNP006 | SEQ ID NO: 230 CCTACACGACGCTCTTCCGATCTCAGGAA GCAGATTCTGCTAATACC | SEQ ID NO: 231 TTCAGACGTGTGCTCTTCCGATCTAAGA TAAACTAGAACCCTGCAGTCT | APC E1309 |
| DCNP007 | SEQ ID NO: 232 CCTACACGACGCTCTTCCGATCTCCTTGT CTCTGTGTTCTTGTCC | SEQ ID NO: 233 TTCAGACGTGTGCTCTTCCGATCTTATA CACCGTGCCGAACGC | EGFR G719 |
| DCNP008 | SEQ ID NO: 234 CCTACACGACGCTCTTCCGATCTCAGTTA ACGTCTTCCTTCTCTCT | SEQ ID NO: 235 TTCAGACGTGTGCTCTTCCGATCTGCAA AGCAGAAACTCACATCGA | EGFR del19 |
| DCNP009 | SEQ ID NO: 236 CCTACACGACGCTCTTCCGATCTCACACT GACGTGCCTCTC | SEQ ID NO: 237 TTCAGACGTGTGCTCTTCCGATCTTCTT TGTGTTCCCGGACATAGT | EGFR T790M |
| DCNP010 | SEQ ID NO: 238 CCTACACGACGCTCTTCCGATCTTCTGTT TCAGGGCATGAACTACT | SEQ ID NO: 239 TTCAGACGTGTGCTCTTCCGATCTTCCT TCTGCATGGTATTCTTTCTCT | EGFR L858 |
| DCNP011 | SEQ ID NO: 240 CCTACACGACGCTCTTCCGATCTGTGGAA AAATAGCCTCAATTCTTACCAT | SEQ ID NO: 241 TTCAGACGTGTGCTCTTCCGATCTACCT CAGATATATTTCTTCATGAAGACCTC | BRAF V600 |

TABLE 19-continued

Primer sequences and corresponding hotspots covered information

| Primer Pair Name | Fwd primer | Rev primer | Covered Hotspots |
|---|---|---|---|
| DCNP012 | SEQ ID NO: 242<br>CCTACACGACGCTCTTCCGATCTACCCAC<br>CTATAATGGTGAATATCTTCAA | SEQ ID NO: 243<br>TTCAGACGTGTGCTCTTCCGATCTGAGA<br>AACCTGTCTCTTGGATATTCTC | KRAS A59,<br>KRAS Q61 |
| DCNP013 | SEQ ID NO: 244<br>CCTACACGACGCTCTTCCGATCTGTCCTG<br>CACCAGTAATATGCATATTAAA | SEQ ID NO: 245<br>TTCAGACGTGTGCTCTTCCGATCTCTGC<br>TGAAAATGACTGAATATAAACTTGTG | KRAS G12,<br>KRAS G13 |

TABLE 20

Summary Table for the Effects of XNA mix on (VAF) and Coverage of sample using OptiSeq ™ Lung and Colorectal Cancer Mini Panel, 0.50% and 1.25%

| | Variant Allelic Frequency, 0.50% | | | | | | Variant Allelic Frequency, 1.25% | | | | | |
|---|---|---|---|---|---|---|---|---|---|---|---|---|
| Hotspot Name | Frequency without XNA, % (Total Coverage) | # of Mutants without XNA | Frequency with XNA, % (Total Coverage) | # of Mutants with XNA | Mutant # Boost Folds | VAF Boost Folds | Frequency without XNA, % (Total Coverage) | # of Mutants without XNA | Frequency with XNA, % (Total Coverage) | # of Mutants with XNA | Mutant # Boost Folds | VAF Boost Folds |
| KRAS A146T | 1.23 (3324) | 41 | 39.23 (581) | 228 | 6 | 31.9 | 3.08 (3324) | 102 | 64.95 (970) | 630 | 6 | 21.1 |
| KRAS G13D | 0.82 (1098) | 9 | 9.89 (130) | 13 | 1 | 12.1 | 2.04 (1098) | 22 | 16.81 (442) | 74 | 3 | 8.2 |
| NRAS A59T | 0.42 (2288) | 10 | 31.52 (499) | 157 | 16 | 75.0 | 1.05 (2288) | 24 | 41.29 (1277) | 527 | 22 | 39.3 |
| EGFR T790M | 0.46 (3396) | 16 | 12.36 (979) | 121 | 8 | 26.9 | 1.15 (3396) | 39 | 25.59 (1680) | 430 | 11 | 22.3 |
| EGFR G719S | 5.04 (5624) | 283 | 98.52 (873) | 860 | 3 | 19.5 | 12.6 (5624) | 709 | 994 (3062) | 3044 | 4 | 7.9 |
| NRAS Q61H | 0.27 (1436) | 4 | 1.36 (319) | 4 | 1 | 5.0 | 0.68 (1436) | 10 | 3.66 (1275) | 47 | 5 | 5.4 |
| NRAS G12V | 0.42 (1495) | 6 | 8.4 (115) | 10 | 2 | 20.0 | 1.05 (1495) | 16 | 22.13 (244) | 54 | 3 | 21.1 |
| PIK3CA H1047R | 3.55 (1879) | 67 | 31.99 (413) | 132 | 2 | 9.0 | 8.87 (1879) | 167 | 64.97 (776) | 504 | 3 | 7.3 |
| EGFR E746-A750 | 0.28 (3424) | 10 | 18.21 (659) | 120 | 13 | 65.0 | 0.69 (3424) | 24 | 34.88 (1004) | 350 | 15 | 50.6 |
| EGFR L858R | 0.4 (2651) | 11 | 10.81 (1290) | 139 | 13 | 27.0 | 1 (2651) | 27 | 24.81 (1724) | 428 | 16 | 24.8 |
| BRAF V600E | 3.41 (2356) | 80 | 37.51 (341) | 128 | 2 | 11.0 | 8.52 (2356) | 201 | 61.43 (921) | 566 | 3 | 7.2 |
| KRAS G12D | 0.83 (1099) | 9 | 29.6 (129) | 38 | 4 | 35.7 | 2.09 (1099) | 23 | 51.09 (443) | 226 | 10 | 24.4 |
| NRAS G13D | 0.4 (1012) | 4 | 6.92 (93) | 6 | 2 | 17.3 | 1.01 (1012) | 10 | 17.65 (243) | 43 | 4 | 17.5 |
| APC E1309fs* | 0.42 (1771) | 7 | 8.51 (384) | 33 | 4 | 20.3 | 1.05 (1771) | 19 | 14.73 (799) | 118 | 6 | 14.0 |
| KRAS A59T | 0.25 (1633) | 4 | 8.13 (1328) | 108 | 26 | 32.5 | 0.61 (1633) | 10 | 16.94 (2276) | 386 | 39 | 27.8 |
| CTNNB1 S45del | 0.51 (65) | 0 | 5.46 (215) | 12 | 35 | 10.7 | 1.275 (65) | 1 | 8.92 (238) | 21 | 26 | 7.0 |
| KRAS Q61L | 0.23 (1564) | 4 | 1.38 (1106) | 15 | 4 | 6.0 | 0.58 (1564) | 9 | 3.77 (2276) | 86 | 9 | 6.5 |
| Average Total Coverage | 2121 | | 556 | | 8.4 | 25.0 | 2121 | | 1156 | | 10.9 | 18.4 |

TABLE 21-A

Average enriched variant allelic frequency (VAF) with XNAs mix

| Hotspots | Original VAF 0.00% With XNA | Original VAF 0.10% With XNA | Original VAF 0.25% With XNA | Original VAF 0.50% With XNA | Original VAF 1.00% With XNA | Original VAF 2.50% With XNA | Original VAF 5.00% With XNA | Original VAF 10.00% With XNA | Original VAF 15.00% With XNA |
|---|---|---|---|---|---|---|---|---|---|
| KRAS A146T | 2.13 | 12.68 | 26.05 | 41.52 | 52.26 | 81.22 | 64.13 | 80.60 | 76.80 |
| KRAS G13D | 0.00 | 2.59 | 5.82 | 9.59 | 15.72 | 22.33 | 10.17 | 17.76 | 26.15 |
| NRAS A59T | 0.34 | 3.89 | 11.94 | 20.72 | 25.89 | 57.69 | 84.13 | 89.93 | 94.07 |
| EGFR T790M | 0.00 | 2.88 | 5.97 | 15.04 | 19.08 | 43.53 | 59.22 | 76.21 | 83.45 |
| EGFR G719S | 16.92 | 94.43 | 94.22 | 98.19 | 98.93 | 99.53 | 99.51 | 98.85 | 90.81 |
| NRAS Q61H | 0.00 | 0.16 | 0.68 | 1.16 | 2.80 | 5.69 | 2.69 | 3.39 | 2.83 |
| NRAS G12V | 0.00 | 3.03 | 5.60 | 4.48 | 20.02 | 24.93 | 40.57 | 30.19 | 66.06 |
| PIK3CA H1047R | 0.00 | 10.98 | 17.22 | 5.29 | 13.90 | 30.01 | 48.54 | 53.11 | 79.36 |
| EGFR E746-A750 | 0.00 | 3.36 | 7.03 | 35.58 | 47.85 | 69.80 | 92.11 | 91.07 | 93.28 |
| EGFR L858R | 0.00 | 3.33 | 3.58 | 11.76 | 17.85 | 36.74 | 28.31 | 57.35 | 77.01 |
| BRAF V600E | 0.00 | 12.04 | 19.28 | 38.32 | 52.92 | 75.23 | 45.17 | 71.38 | 95.00 |
| KRAS G12D | 0.59 | 6.98 | 14.28 | 25.25 | 37.87 | 59.79 | 83.72 | 68.99 | 66.39 |
| NRAS G13D | 0.00 | 3.35 | 4.60 | 5.27 | 13.63 | 25.09 | 23.46 | 40.83 | 79.98 |
| APC E1309fs* | 0.00 | 1.68 | 2.09 | 6.95 | 11.21 | 26.03 | 55.23 | 68.65 | 55.75 |
| KRAS A59T | 0.00 | 1.14 | 3.23 | 6.09 | 8.06 | 22.34 | 27.14 | 47.98 | 39.64 |
| CTNNB1 S45del | 0.00 | 0.45 | 1.85 | 3.26 | 6.79 | 15.09 | 41.72 | 54.71 | 55.20 |
| KRAS Q61L | 0.00 | 0.00 | 0.53 | 1.28 | 3.08 | 7.56 | 7.97 | 25.96 | 38.61 |

TABLE 21-B

Average original variant allelic frequency (VAF) without XNAs mix

| Hotspots | Original VAF 0.00% No XNA | Original VAF 0.10% No XNA | Original VAF 0.25% No XNA | Original VAF 0.50% No XNA | Original VAF 1.00% No XNA | Original VAF 2.50% No XNA | Original VAF 5.00% No XNA | Original VAF 10.00% No XNA | Original VAF 15.00% No XNA |
|---|---|---|---|---|---|---|---|---|---|
| KRAS A146T | 0.00 | 0.24 | 0.60 | 1.20 | 2.39 | 5.99 | 3.19 | 6.53 | 6.53 |
| KRAS G13D | 0.00 | 0.18 | 0.45 | 0.90 | 1.80 | 4.49 | 5.73 | 6.71 | 12.72 |
| NRAS A59T | 0.00 | 0.12 | 0.29 | 0.58 | 1.15 | 2.89 | 7.87 | 12.06 | 20.29 |
| EGFR T790M | 0.00 | 0.09 | 0.21 | 0.43 | 0.86 | 2.15 | 3.06 | 7.43 | 15.31 |
| EGFR G719S | 0.00 | 0.90 | 2.25 | 4.50 | 9.00 | 22.51 | 22.68 | 19.38 | 11.28 |
| NRAS Q61H | 0.00 | 0.09 | 0.23 | 0.46 | 0.92 | 2.31 | 2.89 | 7.06 | 10.85 |
| NRAS G12V | 0.00 | 0.10 | 0.26 | 0.52 | 1.03 | 2.58 | 3.93 | 5.03 | 9.47 |
| PIK3CA H1047R | 0.00 | 0.70 | 1.75 | 3.50 | 6.99 | 17.49 | 23.77 | 39.28 | 27.83 |
| EGFR E746-A750 | 0.00 | 0.06 | 0.14 | 0.29 | 0.58 | 1.44 | 5.41 | 6.76 | 15.07 |
| EGFR L858R | 0.00 | 0.08 | 0.20 | 0.39 | 0.79 | 1.96 | 1.53 | 4.80 | 12.37 |
| BRAF | 0.00 | 0.64 | 1.61 | 3.21 | 6.43 | 16.07 | 6.06 | 14.01 | 55.13 |

TABLE 21-B-continued

Average original variant allelic frequency (VAF) without XNAs mix

| Hotspots | Original VAF 0.00% No XNA | Original VAF 0.10% No XNA | Original VAF 0.25% No XNA | Original VAF 0.50% No XNA | Original VAF 1.00% No XNA | Original VAF 2.50% No XNA | Original VAF 5.00% No XNA | Original VAF 10.00% No XNA | Original VAF 15.00% No XNA |
|---|---|---|---|---|---|---|---|---|---|
| V600E KRAS G12D | 0.00 | 0.16 | 0.40 | 0.80 | 1.61 | 4.02 | 14.32 | 6.78 | 10.21 |
| NRAS G13D | 0.00 | 0.10 | 0.26 | 0.52 | 1.05 | 2.61 | 4.02 | 8.76 | 14.56 |
| APC E1309fs* | 0.00 | 0.07 | 0.17 | 0.34 | 0.68 | 1.71 | 5.07 | 9.89 | 11.77 |
| KRAS A59T | 0.00 | 0.08 | 0.19 | 0.38 | 0.77 | 1.92 | 2.54 | 7.10 | 6.70 |
| CTNNB1 S45del | 0.00 | 0.07 | 0.19 | 0.37 | 0.75 | 1.86 | 4.09 | 5.85 | 12.49 |
| KRAS Q61L | 0.00 | 0.08 | 0.21 | 0.42 | 0.83 | 2.08 | 2.56 | 18.63 | 29.76 |

Cut-Off—2% for Original Variant Allelic Frequency

TABLE 22-A

Regression equations for hotspots with original allelic frequency (Original VAF) less than 2.00%

| Hotspots | Equation | $R^2$ | Confidence interval (x) | Confidence interval (y) |
|---|---|---|---|---|
| KRAS A146T | y = 36.96x | 0.9517 | [0, 2] | [0, 73.9] |
| KRAS G13D | y = 9.3533x | 0.9602 | [0, 2] | [0, 18.7] |
| NRAS A59T | y = 25.954x | 0.8504 | [0, 2] | [0, 51.9] |
| EGFR T790M | y = 24.962x | 0.9052 | [0, 2] | [0, 49.9] |
| EGFR G719S | y = 104.89x | 0.9047 | [0, 2] | [0, 100] |
| NRAS Q61H | y = 2.9212x | 0.9887 | [0, 2] | [0, 5.8] |
| NRAS G12V | y = 17.558x | 0.8874 | [0, 2] | [0, 35.1] |
| PIK3CA H1047R | y = 10.655x | 0.905 | [0, 2] | [0, 21.3] |
| EGFR E746-A750 | y = 55.532x | 0.8163 | [0, 2] | [0, 100] |
| EGFR L858R | y = 19.254x | 0.9733 | [0, 2] | [0, 38.5] |
| BRAF V600E | y = 12.929x | 0.9149 | [0, 2] | [0, 25.9] |
| KRAS G12D | y = 25.768x | 0.9353 | [0, 2] | [0, 51.5] |
| NRAS G13D | y = 12.837x | 0.9244 | [0, 2] | [0, 25.7] |
| APC E1309fs* | y = 15.525x | 0.9915 | [0, 2] | [0, 31.1] |
| KRAS A59T | y = 11.693x | 0.9868 | [0, 2] | [0, 23.4] |
| CTNNB1 S45del | y = 8.2626x | 0.996 | [0, 2] | [0, 16.5] |
| KRAS Q61L | y = 3.5017x | 0.9722 | [0, 2] | [0, 7] |
| Number with $R^2$ > 0.9 | 14 | | | |
| Percentage with $R^2$ > 0.9 | 82.35% | | | |

TABLE 22-B

Regression equations for hotspots with original allelic frequency (Original VAF) more than 2.00%

| Hotspots | Equation | $R^2$ | Confidence interval (x) | Confidence interval (y) |
|---|---|---|---|---|
| KRAS A146T | $y = -2.3889x^2 + 27.709x$ | 0.9865 | [2, 6.5] | [45.9, 79.2] |
| KRAS G13D | $y = 0.5868x^2 - 9.3552x + 50.331$ | 0.6263 | [2, 12.7] | [34, 26.2] |
| NRAS A59T | $y = -0.202x^2 + 6.6933x + 41.012$ | 0.9806 | [2, 20.3] | [53.6, 93.6] |
| EGFR T790M | $y = -0.37892x^2 + 9.3359x + 29.137$ | 0.955 | [2, 15.3] | [46.3, 83.3] |
| EGFR G719S | $y = 0.0222x^2 - 0.3879x + 97.06$ | 0.3157 | [2, 22.7] | [96.4, 99.7] |
| NRAS Q61H | $y = 0.0337x^2 - 0.6216x + 5.7134$ | 0.3222 | [2, 10.9] | [4.6, 2.9] |
| NRAS G12V | $y = 0.4788x^2 - 0.3143x + 25.679$ | 0.8782 | [2, 9.6] | [27, 65.9] |
| PIK3CA H1047R | $y = -0.0641x^2 + 4.3557x - 13.199$ | 0.8138 | [2, 39.3] | [0, 59] |
| EGFR E746-A750 | $y = 0.107x^2 - 2.0697x + 100.18$ | 1 | [2, 15.1] | [96.5, 93.3] |
| EGFR L858R | $y = 2.5996x + 44.863$ | 1 | [2, 12.4] | [50.1, 77.1] |
| BRAF V600E | $y = -0.0464x^2 + 3.7915x + 26.927$ | 0.9901 | [2, 55.1] | [34.3, 95] |
| KRAS G12D | $y = 0.1551x^2 - 0.817x + 62.541$ | 0.8543 | [2, 14.3] | [61.5, 82.6] |
| NRAS G13D | $y = 0.3565x^2 - 1.4161x + 25.151$ | 0.9975 | [2, 14.6] | [23.7, 80.5] |
| APC E1309fs* | $y = -1.44x^2 + 24.328x - 31.099$ | 1 | [2, 11.8] | [11.8, 55.5] |
| KRAS A59T | $y = 3.8664x^2 - 32.697x + 85.225$ | 1 | [2, 7.1] | [35.3, 48] |
| CTNNB1 S45del | $y = -0.8701x^2 + 16.029x - 9.2552$ | 1 | [2, 12.5] | [19.3, 55.2] |
| KRAS Q61L | $y = 0.0008x^2 + 1.0992x + 5.212$ | 1 | [2, 29.8] | [7.4, 38.7] |
| Number with $R^2$ > 0.9 | | 11 | | |
| Percentage with $R^2$ > 0.9 | | | | |

All literature and similar materials cited in this application including, but not limited to, patents, patent applications, articles, books, treatises, and internet web pages, regardless of the format of such literature and similar materials, are expressly incorporated by reference in their entirety for any purpose as if they were entirely denoted. In the event that one or more of the incorporated literature and similar materials defines or uses a term in such a way that it contradicts that term's definition in this application, this application controls.

Although the foregoing description contains many specifics, these should not be construed as limiting the scope of the present invention, but merely as providing illustrations of some of the presently preferred embodiments. Similarly, other embodiments may be devised without departing from the spirit or scope of the present invention. Features from different embodiments may be employed in combination. The scope of the invention is, therefore, indicated and limited only by the appended claims and their legal equivalents rather than by the foregoing description. All additions, deletions and modifications to the invention as disclosed herein which fall within the meaning and scope of the claims are to be embraced thereby.

REFERENCES

1. Muzzey, D., Evans, E. A. & Lieber, C. Understanding the Basics of NGS: From Mechanism to Variant. Calling. Curr. Genet. Med. Rep. 3, 158-165 (2015).
2. Meldrum, C., Doyle, M. A. & Tothill, R. W. Next-Generation Sequencing for Cancer Diagnostics: a Practical Perspective. Clin. Biochem. Rev. 32, 177-195 (2011).
3. Kou, R. et al. Benefits and challenges with applying unique molecular identifiersin next generation sequencing to detect low frequency mutations. PLoS ONE. 11, e0146638 (2016).
4. Kinde, I., Wu, J., Papadopoulos, N., Kinzler, K. W. & Vogelstein, B. Detection and quantification of rare mutations with massively parallel sequencing. Proc. Natl. Acad. Sci. U.S.A. 108, 9530-9535 (2011).

5. Clement, K., Farouni, R., Bauer, D. E. & Pinello, L. AmpUMI: design and analysis of unique molecular identifiers for deep amplicon sequencing. Bioinformatics. 34, i202-i210 (2018).
6. Powell, J. P. & Zhang, A. DNA Mutation Detection Employing Enrichment of Mutant Polynucleotide Sequences and Minimally Invasive Sampling. U.S. Pat. No. 20160194691. United States Patent and Trademark Office (2016).
7. Powell, J. P. & Zhang, A. Detection of PNA clamping. U.S. Pat. No. 9,745,633. United States Patent and Trademark Office (2017).
8. Powell, J. P. Specific Synthetic Chimeric Xenonucleic Acid Guide RNA; s(XNA-gRNA) for Enhancing CRISPER Mediated Genome Editing Efficiency. U.S. Pat. No. 20180066258. United States Patent and Trademark Office (2018).

What is claimed is:

1. A method for enriching a target polynucleotide sequence containing a genetic variation, said method comprising:
   (a) providing a biological sample;
   (b) isolating DNA from said biological sample; said DNA including said target polynucleotide sequence containing a genetic variation;
   (c) providing two primer probes targeted to said target polynucleotide sequence said primer probes allowing formation of a PCR process product;
   (d) providing a target specific xenonucleic acid clamp oligomer specific for a wildtype polynucleotide sequence, wherein said xenonucleic acid includes chemical moieties selected from the group consisting of oxy-aza, aza-aza, thio-aza and mixtures thereof;
   (e) admixing the primer probes and the xenonucleic clamping probe with the target nucleic acid sample;
   (f) performing a PCR amplification process in a reaction solution under hybridization conditions thereby generating multiple amplicons; and
   (g) detecting said amplicons.

2. The method of claim 1, wherein said detection employs oligonucleotide probes specific for hybridization of variant polynucleotide amplicon sequences.

3. The method of claim 1, wherein the target sequence is in a gene selected from the group consisting of: KRAS, BRAF, EGFR, TP53, JAK2, NPM1, and PCA3.

4. A method for enriching multiple target polynucleotide sequences containing a genetic variation, said method comprising:
   (a) providing a biological sample;
   (b) isolating DNA from said biological sample; said DNA including said multiple target polynucleotide sequences containing a genetic variation;
   (c) providing a library of amplifying primer probes targeted to said multiple target polynucleotide sequences containing a genetic variation; said primer probes allowing formation of PCR process products;
   (d) providing a library of target specific xenonucleic acid clamp oligomer specific for multiple wildtype polynucleotide sequences, wherein said xenonucleic acid includes moieties selected from the group consisting of oxy-aza, aza-aza, thio-aza and mixtures thereof;
   (e) admixing the primer probes and the xenonucleic clamping probes with the multiple target nucleic add samples;
   (f) performing a PCR amplification process in a reaction solution under hybridization conditions thereby generating multiple amplicons; and
   (g) detecting said amplicons.

5. The method of claim 3, wherein said detection employs oligonucleotide probes specific for hybridization of variant polynucleotide amplicon sequences.

6. A method for conducting a minimally invasive biopsy in a mammalian subject suspected of a having a neoplastic disease, said method comprising:
   (a) providing a biological sample derived from said mammalian subject;
   (b) isolating DNA from said biological sample; said DNA including multiple target polynucleotide sequences containing a genetic variation;
   (c) providing a library of amplifying primer probes targeted to said multiple target poly-nucleotide sequences containing a genetic variation; said primer probes allowing formation of PCR process products;
   (d) providing a library of target specific xenonucleic acid clamp oligomer specific for multiple wildtype polynucleotide sequences, wherein said xenonucleic acid includes moieties selected from the group consisting of oxy-aza, aza-aza, thi-aza and mixtures thereof;
   (e) performing a PCR amplification process in a reaction solution under hybridization conditions thereby generating multiple amplicons; and
   (f) detecting said amplicons.

7. The method of claim 6, wherein said sampled target polynucleotides are sampled from cells derived from said mammalian subject.

8. The method of claim 6, wherein said sampled target polynucleotides are sampled from free circulating cell free polynucleotides derived from said mammalian subject.

9. The method of claim 4, which includes using multiple XNA clamp probes and amplifying primers targeted to multiple polynucleotide sequences.

10. The method of claim 6, wherein said neoplastic disease is lung cancer.

11. The method of claim 6, wherein said neoplastic disease is colorectal cancer.

12. The method of claim 6, wherein said neoplastic disease is breast cancer.

* * * * *

SEQUENCE LISTING

```
<160> NUMBER OF SEQ ID NOS: 247

<210> SEQ ID NO 1
<211> LENGTH: 13
<212> TYPE: DNA
<213> ORGANISM: Artificial
<220> FEATURE:
<223> OTHER INFORMATION: synthetic

<400> SEQUENCE: 1
agctgctggc gta                                                          13

<210> SEQ ID NO 2
<211> LENGTH: 13
<212> TYPE: DNA
<213> ORGANISM: Artificial
<220> FEATURE:
<223> OTHER INFORMATION: synthetic

<400> SEQUENCE: 2
agctcgtggc gta                                                          13

<210> SEQ ID NO 3
<211> LENGTH: 13
<212> TYPE: DNA
<213> ORGANISM: Artificial
<220> FEATURE:
<223> OTHER INFORMATION: synthetic

<400> SEQUENCE: 3
agctgatggc gta                                                          13

<210> SEQ ID NO 4
<211> LENGTH: 13
<212> TYPE: DNA
<213> ORGANISM: Artificial
<220> FEATURE:
<223> OTHER INFORMATION: synthetic

<400> SEQUENCE: 4
agcttgtggc gta                                                          13

<210> SEQ ID NO 5
<211> LENGTH: 13
<212> TYPE: DNA
<213> ORGANISM: Artificial
<220> FEATURE:
<223> OTHER INFORMATION: synthetic

<400> SEQUENCE: 5
gagctattgg cgt                                                          13

<210> SEQ ID NO 6
<211> LENGTH: 13
<212> TYPE: DNA
<213> ORGANISM: Artificial
```

```
<220> FEATURE:
<223> OTHER INFORMATION: synthetic

<400> SEQUENCE: 6
gagctcttgg cgt                                                         13

<210> SEQ ID NO 7
<211> LENGTH: 13
<212> TYPE: DNA
<213> ORGANISM: Artificial
<220> FEATURE:
<223> OTHER INFORMATION: synthetic

<400> SEQUENCE: 7
agctagtggc gta                                                         13

<210> SEQ ID NO 8
<211> LENGTH: 13
<212> TYPE: DNA
<213> ORGANISM: Artificial
<220> FEATURE:
<223> OTHER INFORMATION: synthetic

<400> SEQUENCE: 8
agctgttggc gta                                                         13

<210> SEQ ID NO 9
<211> LENGTH: 13
<212> TYPE: DNA
<213> ORGANISM: Artificial
<220> FEATURE:
<223> OTHER INFORMATION: synthetic

<400> SEQUENCE: 9
tggttgcgta ggc                                                         13

<210> SEQ ID NO 10
<211> LENGTH: 13
<212> TYPE: DNA
<213> ORGANISM: Artificial
<220> FEATURE:
<223> OTHER INFORMATION: synthetic

<400> SEQUENCE: 10
tggtgacgta ggc                                                         13

<210> SEQ ID NO 11
<211> LENGTH: 13
<212> TYPE: DNA
<213> ORGANISM: Artificial
<220> FEATURE:
<223> OTHER INFORMATION: synthetic

<400> SEQUENCE: 11
tggtgccgta ggc                                                         13

<210> SEQ ID NO 12
<211> LENGTH: 13
<212> TYPE: DNA
<213> ORGANISM: Artificial
<220> FEATURE:
<223> OTHER INFORMATION: synthetic

<400> SEQUENCE: 12
tggtgtcgta ggc                                                         13
```

```
<210> SEQ ID NO 13
<211> LENGTH: 13
<212> TYPE: DNA
<213> ORGANISM: Artificial
<220> FEATURE:
<223> OTHER INFORMATION: synthetic

<400> SEQUENCE: 13
tggtagcgta ggc                                                          13

<210> SEQ ID NO 14
<211> LENGTH: 13
<212> TYPE: DNA
<213> ORGANISM: Artificial
<220> FEATURE:
<223> OTHER INFORMATION: synthetic

<400> SEQUENCE: 14
tggtcgcgta ggc                                                          13

<210> SEQ ID NO 15
<211> LENGTH: 13
<212> TYPE: DNA
<213> ORGANISM: Artificial
<220> FEATURE:
<223> OTHER INFORMATION: synthetic

<400> SEQUENCE: 15
ggagacggtc tgg                                                          13

<210> SEQ ID NO 16
<211> LENGTH: 13
<212> TYPE: DNA
<213> ORGANISM: Artificial
<220> FEATURE:
<223> OTHER INFORMATION: synthetic

<400> SEQUENCE: 16
ggagacgctc tgg                                                          13

<210> SEQ ID NO 17
<211> LENGTH: 13
<212> TYPE: DNA
<213> ORGANISM: Artificial
<220> FEATURE:
<223> OTHER INFORMATION: synthetic

<400> SEQUENCE: 17
ctggtggcgt agg                                                          13

<210> SEQ ID NO 18
<211> LENGTH: 13
<212> TYPE: DNA
<213> ORGANISM: Artificial
<220> FEATURE:
<223> OTHER INFORMATION: synthetic

<400> SEQUENCE: 18
aaggcctgct gaa                                                          13

<210> SEQ ID NO 19
<211> LENGTH: 24
<212> TYPE: DNA
<213> ORGANISM: Artificial
<220> FEATURE:
<223> OTHER INFORMATION: synthetic
```

<400> SEQUENCE: 19
gtactggtgg agtatttgat agtg                                          24

<210> SEQ ID NO 20
<211> LENGTH: 23
<212> TYPE: DNA
<213> ORGANISM: Artificial
<220> FEATURE:
<223> OTHER INFORMATION: synthetic

<400> SEQUENCE: 20
atcgtcaagg cactcttgcc tac                                           23

<210> SEQ ID NO 21
<211> LENGTH: 27
<212> TYPE: DNA
<213> ORGANISM: artificial
<220> FEATURE:
<223> OTHER INFORMATION: synthetic

<400> SEQUENCE: 21
cgaaagaccc tagccttaga taaaact                                       27

<210> SEQ ID NO 22
<211> LENGTH: 25
<212> TYPE: DNA
<213> ORGANISM: artificial
<220> FEATURE:
<223> OTHER INFORMATION: synthetic

<400> SEQUENCE: 22
attgtgtgga agatccaatc cattt                                         25

<210> SEQ ID NO 23
<211> LENGTH: 32
<212> TYPE: DNA
<213> ORGANISM: artificial
<220> FEATURE:
<223> OTHER INFORMATION: synthetic

<400> SEQUENCE: 23
acgttggatg tgtaccatac ctgtctggtc tt                                 32

<210> SEQ ID NO 24
<211> LENGTH: 48
<212> TYPE: DNA
<213> ORGANISM: artificial
<220> FEATURE:
<223> OTHER INFORMATION: synthetic

<400> SEQUENCE: 24
gttttcccag tcacgacacg ttggatgcag ccaggaacgt actggtga                48

<210> SEQ ID NO 25
<211> LENGTH: 23
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (1)..(23)
<223> OTHER INFORMATION: Biotin modified

<400> SEQUENCE: 25
ctccagatct cagtaaggta cgg                                                23

<210> SEQ ID NO 26
<211> LENGTH: 22
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(22)
<223> OTHER INFORMATION: Biotin modified

<400> SEQUENCE: 26
tgagggagat ccgacaatac ag                                                 22

<210> SEQ ID NO 27
<211> LENGTH: 31
<212> TYPE: DNA
<213> ORGANISM: artificial
<220> FEATURE:
<223> OTHER INFORMATION: synthetic

<400> SEQUENCE: 27
acagtaaaaa taggtgattt tggtctagct a                                       31

<210> SEQ ID NO 28
<211> LENGTH: 58
<212> TYPE: DNA
<213> ORGANISM: artificial
<220> FEATURE:
<223> OTHER INFORMATION: synthetic

<400> SEQUENCE: 28
gttttcccag tcacgacacg ttggatgaca gtaaaatag gtgattttgg tctagcta           58

<210> SEQ ID NO 29
<211> LENGTH: 24
<212> TYPE: DNA
<213> ORGANISM: artificial
<220> FEATURE:
<223> OTHER INFORMATION: synthetic

<400> SEQUENCE: 29
catccacaaa atggatccag acaa                                               24

<210> SEQ ID NO 30
<211> LENGTH: 51
<212> TYPE: DNA
<213> ORGANISM: artificial
<220> FEATURE:
<223> OTHER INFORMATION: synthetic

<400> SEQUENCE: 30
caggaaacag ctatgacacg ttggatgcat ccacaaaatg gatccagaca a                 51

<210> SEQ ID NO 31
<211> LENGTH: 23
<212> TYPE: DNA
<213> ORGANISM: artificial
<220> FEATURE:
<223> OTHER INFORMATION: synthetic

<400> SEQUENCE: 31
ctccagatct cagtaaggta cgg                                                23

```
<210> SEQ ID NO 32
<211> LENGTH: 21
<212> TYPE: DNA
<213> ORGANISM: artificial
<220> FEATURE:
<223> OTHER INFORMATION: synthetic

<400> SEQUENCE: 32
gggaaagagt ggtctctcat c                                              21

<210> SEQ ID NO 33
<211> LENGTH: 28
<212> TYPE: DNA
<213> ORGANISM: artificial
<220> FEATURE:
<223> OTHER INFORMATION: synthetic

<400> SEQUENCE: 33
acgttggatg tccaccgtgc agctcatc                                       28

<210> SEQ ID NO 34
<211> LENGTH: 41
<212> TYPE: DNA
<213> ORGANISM: artificial
<220> FEATURE:
<223> OTHER INFORMATION: synthetic

<400> SEQUENCE: 34
gttttcccag tcacgacacg ttggatgtcc accgtgcagc t                        41

<210> SEQ ID NO 35
<211> LENGTH: 30
<212> TYPE: DNA
<213> ORGANISM: artificial
<220> FEATURE:
<223> OTHER INFORMATION: synthetic

<400> SEQUENCE: 35
acgttggatg gtctttgtgt tcccggacat                                     30

<210> SEQ ID NO 36
<211> LENGTH: 41
<212> TYPE: DNA
<213> ORGANISM: artificial
<220> FEATURE:
<223> OTHER INFORMATION: synthetic

<400> SEQUENCE: 36
caggaaacag ctatgacacg ttggatggtc tttgtgttcc c                        41

<210> SEQ ID NO 37
<211> LENGTH: 53
<212> TYPE: DNA
<213> ORGANISM: artificial
<220> FEATURE:
<223> OTHER INFORMATION: synthetic

<400> SEQUENCE: 37
gttttcccag tcacgacacg ttggatgctc tctgtcatag ggactctgga tcc           53

<210> SEQ ID NO 38
<211> LENGTH: 26
<212> TYPE: DNA
<213> ORGANISM: artificial
<220> FEATURE:
<223> OTHER INFORMATION: synthetic
```

```
<400> SEQUENCE: 38
ctctctgtca tagggactct ggatcc                                         26

<210> SEQ ID NO 39
<211> LENGTH: 24
<212> TYPE: DNA
<213> ORGANISM: artificial
<220> FEATURE:
<223> OTHER INFORMATION: synthetic

<400> SEQUENCE: 39
agcaaagcag aaactcacat cgag                                           24

<210> SEQ ID NO 40
<211> LENGTH: 51
<212> TYPE: DNA
<213> ORGANISM: artificial
<220> FEATURE:
<223> OTHER INFORMATION: synthetic

<400> SEQUENCE: 40
caggaaacag ctatgacacg ttggatgagc aaagcagaaa ctcacatcga g              51

<210> SEQ ID NO 41
<211> LENGTH: 49
<212> TYPE: DNA
<213> ORGANISM: artificial
<220> FEATURE:
<223> OTHER INFORMATION: synthetic

<400> SEQUENCE: 41
gttttcccag tcacgacacg ttggatggct cccaaccaag ctctcttga                49

<210> SEQ ID NO 42
<211> LENGTH: 22
<212> TYPE: DNA
<213> ORGANISM: artificial
<220> FEATURE:
<223> OTHER INFORMATION: synthetic

<400> SEQUENCE: 42
gctcccaacc aagctctctt ga                                             22

<210> SEQ ID NO 43
<211> LENGTH: 25
<212> TYPE: DNA
<213> ORGANISM: artificial
<220> FEATURE:
<223> OTHER INFORMATION: synthetic

<400> SEQUENCE: 43
ctgtgccagg gaccttacct tatac                                          25

<210> SEQ ID NO 44
<211> LENGTH: 52
<212> TYPE: DNA
<213> ORGANISM: artificial
<220> FEATURE:
<223> OTHER INFORMATION: synthetic

<400> SEQUENCE: 44
caggaaacag ctatgacacg ttggatgctg tgccagggac cttaccttat ac            52

<210> SEQ ID NO 45
<211> LENGTH: 23
```

```
<212> TYPE: DNA
<213> ORGANISM: artificial
<220> FEATURE:
<223> OTHER INFORMATION: synthetic

<400> SEQUENCE: 45
tttgccaagg cacgagtaac aag                                              23

<210> SEQ ID NO 46
<211> LENGTH: 23
<212> TYPE: DNA
<213> ORGANISM: artificial
<220> FEATURE:
<223> OTHER INFORMATION: synthetic

<400> SEQUENCE: 46
cccaaggacc acctcacagt tat                                              23

<210> SEQ ID NO 47
<211> LENGTH: 26
<212> TYPE: DNA
<213> ORGANISM: artificial
<220> FEATURE:
<223> OTHER INFORMATION: synthetic

<400> SEQUENCE: 47
ttaactgcag atgcacatca ttacct                                           26

<210> SEQ ID NO 48
<211> LENGTH: 23
<212> TYPE: DNA
<213> ORGANISM: artificial
<220> FEATURE:
<223> OTHER INFORMATION: synthetic

<400> SEQUENCE: 48
ggactctgaa gatgtaccta tgg                                              23

<210> SEQ ID NO 49
<211> LENGTH: 50
<212> TYPE: DNA
<213> ORGANISM: artificial
<220> FEATURE:
<223> OTHER INFORMATION: synthetic

<400> SEQUENCE: 49
gttttcccag tcacgacacg ttggatggga ctctgaagat gtacctatgg                 50

<210> SEQ ID NO 50
<211> LENGTH: 20
<212> TYPE: DNA
<213> ORGANISM: artificial
<220> FEATURE:
<223> OTHER INFORMATION: synthetic

<400> SEQUENCE: 50
gctaagtcct gagcctgttt                                                  20

<210> SEQ ID NO 51
<211> LENGTH: 47
<212> TYPE: DNA
<213> ORGANISM: artificial
<220> FEATURE:
<223> OTHER INFORMATION: synthetic

<400> SEQUENCE: 51
```
caggaaacag ctatgacacg ttggatggct aagtcctgag cctgttt    47

<210> SEQ ID NO 52
<211> LENGTH: 20
<212> TYPE: DNA
<213> ORGANISM: artificial
<220> FEATURE:
<223> OTHER INFORMATION: synthetic

<400> SEQUENCE: 52
acacaaaaca ggctcaggac    20

<210> SEQ ID NO 53
<211> LENGTH: 47
<212> TYPE: DNA
<213> ORGANISM: artificial
<220> FEATURE:
<223> OTHER INFORMATION: synthetic

<400> SEQUENCE: 53
gttttcccag tcacgacacg ttggatgaca caaaacaggc tcaggac    47

<210> SEQ ID NO 54
<211> LENGTH: 25
<212> TYPE: DNA
<213> ORGANISM: artificial
<220> FEATURE:
<223> OTHER INFORMATION: synthetic

<400> SEQUENCE: 54
cagtgttact tacctgtctt gtctt    25

<210> SEQ ID NO 55
<211> LENGTH: 52
<212> TYPE: DNA
<213> ORGANISM: artificial
<220> FEATURE:
<223> OTHER INFORMATION: synthetic

<400> SEQUENCE: 55
caggaaacag ctatgacacg ttggatgcag tgttacttac ctgtcttgtc tt    52

<210> SEQ ID NO 56
<211> LENGTH: 21
<212> TYPE: DNA
<213> ORGANISM: artificial
<220> FEATURE:
<223> OTHER INFORMATION: synthetic

<400> SEQUENCE: 56
aaggcctgct gaaaatgact g    21

<210> SEQ ID NO 57
<211> LENGTH: 48
<212> TYPE: DNA
<213> ORGANISM: artificial
<220> FEATURE:
<223> OTHER INFORMATION: synthetic

<400> SEQUENCE: 57
gttttcccag tcacgacacg ttggatgaag gcctgctgaa aatgactg    48

<210> SEQ ID NO 58
<211> LENGTH: 48
<212> TYPE: DNA
<213> ORGANISM: artificial

<220> FEATURE:
<223> OTHER INFORMATION: synthetic

<400> SEQUENCE: 58
caggaaacag ctatgacacg ttggatgtca aggcactctt gcctacgc          48

<210> SEQ ID NO 59
<211> LENGTH: 22
<212> TYPE: DNA
<213> ORGANISM: artificial
<220> FEATURE:
<223> OTHER INFORMATION: synthetic

<400> SEQUENCE: 59
acttgtggta gttggagctg gt          22

<210> SEQ ID NO 60
<211> LENGTH: 49
<212> TYPE: DNA
<213> ORGANISM: artificial
<220> FEATURE:
<223> OTHER INFORMATION: synthetic

<400> SEQUENCE: 60
gttttcccag tcacgacacg ttggatgact tgtggtagtt ggagctggt          49

<210> SEQ ID NO 61
<211> LENGTH: 25
<212> TYPE: DNA
<213> ORGANISM: artificial
<220> FEATURE:
<223> OTHER INFORMATION: synthetic

<400> SEQUENCE: 61
tcatgaaaat ggtcagagaa acctt          25

<210> SEQ ID NO 62
<211> LENGTH: 49
<212> TYPE: DNA
<213> ORGANISM: artificial
<220> FEATURE:
<223> OTHER INFORMATION: synthetic

<400> SEQUENCE: 62
caggaaacag ctatgacacg ttggatgact tgtggtagtt ggagctggt          49

<210> SEQ ID NO 63
<211> LENGTH: 23
<212> TYPE: DNA
<213> ORGANISM: artificial
<220> FEATURE:
<223> OTHER INFORMATION: synthetic

<400> SEQUENCE: 63
attgcactgt actcctcttg acc          23

<210> SEQ ID NO 64
<211> LENGTH: 50
<212> TYPE: DNA
<213> ORGANISM: artificial
<220> FEATURE:
<223> OTHER INFORMATION: synthetic

<400> SEQUENCE: 64
caggaaacag ctatgacacg ttggatgatt gcactgtact cctcttgacc          50

<210> SEQ ID NO 65
<211> LENGTH: 27
<212> TYPE: DNA
<213> ORGANISM: artificial
<220> FEATURE:
<223> OTHER INFORMATION: synthetic

<400> SEQUENCE: 65
ctcttggata ttctcgacac agcaggt                                    27

<210> SEQ ID NO 66
<211> LENGTH: 54
<212> TYPE: DNA
<213> ORGANISM: artificial
<220> FEATURE:
<223> OTHER INFORMATION: synthetic

<400> SEQUENCE: 66
gttttcccag tcacgacacg ttggatgctc ttggatattc tcgacacagc aggt      54

<210> SEQ ID NO 67
<211> LENGTH: 20
<212> TYPE: DNA
<213> ORGANISM: artificial
<220> FEATURE:
<223> OTHER INFORMATION: synthetic

<400> SEQUENCE: 67
ccagactgtg tttctccctt                                            20

<210> SEQ ID NO 68
<211> LENGTH: 47
<212> TYPE: DNA
<213> ORGANISM: artificial
<220> FEATURE:
<223> OTHER INFORMATION: synthetic

<400> SEQUENCE: 68
gttttcccag tcacgacacg ttggatgcca gactgtgttt ctccctt              47

<210> SEQ ID NO 69
<211> LENGTH: 22
<212> TYPE: DNA
<213> ORGANISM: artificial
<220> FEATURE:
<223> OTHER INFORMATION: synthetic

<400> SEQUENCE: 69
tgagggagat ccgacaatac ag                                         22

<210> SEQ ID NO 70
<211> LENGTH: 25
<212> TYPE: DNA
<213> ORGANISM: artificial
<220> FEATURE:
<223> OTHER INFORMATION: synthetic

<400> SEQUENCE: 70
tctgccaaaa ttaatgtgct gaact                                      25

<210> SEQ ID NO 71
<211> LENGTH: 18
<212> TYPE: DNA
<213> ORGANISM: artificial
<220> FEATURE:
<223> OTHER INFORMATION: synthetic

<400> SEQUENCE: 71
ttctcttccg cacccagc                                                      18

<210> SEQ ID NO 72
<211> LENGTH: 45
<212> TYPE: DNA
<213> ORGANISM: artificial
<220> FEATURE:
<223> OTHER INFORMATION: synthetic

<400> SEQUENCE: 72
caggaaacag ctatgacacg ttggatgttc tcttccgcac ccagc                         45

<210> SEQ ID NO 73
<211> LENGTH: 51
<212> TYPE: DNA
<213> ORGANISM: artificial
<220> FEATURE:
<223> OTHER INFORMATION: synthetic

<400> SEQUENCE: 73
gttttcccag tcacgacacg ttggatgtga aaacaccgca gcatgtcaag a                  51

<210> SEQ ID NO 74
<211> LENGTH: 24
<212> TYPE: DNA
<213> ORGANISM: artificial
<220> FEATURE:
<223> OTHER INFORMATION: synthetic

<400> SEQUENCE: 74
tgaaaacacc gcagcatgtc aaga                                               24

<210> SEQ ID NO 75
<211> LENGTH: 24
<212> TYPE: DNA
<213> ORGANISM: artificial
<220> FEATURE:
<223> OTHER INFORMATION: synthetic

<400> SEQUENCE: 75
ccttactttg cctccttctg catg                                               24

<210> SEQ ID NO 76
<211> LENGTH: 51
<212> TYPE: DNA
<213> ORGANISM: artificial
<220> FEATURE:
<223> OTHER INFORMATION: synthetic

<400> SEQUENCE: 76
caggaaacag ctatgacacg ttggatgcct tactttgcct ccttctgcat g                  51

<210> SEQ ID NO 77
<211> LENGTH: 26
<212> TYPE: DNA
<213> ORGANISM: artificial
<220> FEATURE:
<223> OTHER INFORMATION: synthetic

<400> SEQUENCE: 77
tggtgggatc atattcatct acaaag                                             26

<210> SEQ ID NO 78

```
<211> LENGTH: 26
<212> TYPE: DNA
<213> ORGANISM: artificial
<220> FEATURE:
<223> OTHER INFORMATION: synthetic

<400> SEQUENCE: 78
tggtgggatc atattcatct acaaag                                          26

<210> SEQ ID NO 79
<211> LENGTH: 53
<212> TYPE: DNA
<213> ORGANISM: artificial
<220> FEATURE:
<223> OTHER INFORMATION: synthetic

<400> SEQUENCE: 79
caggaaacag ctatgacacg ttggatgtgg tgggatcata ttcatctaca aag             53

<210> SEQ ID NO 80
<211> LENGTH: 27
<212> TYPE: DNA
<213> ORGANISM: artificial
<220> FEATURE:
<223> OTHER INFORMATION: synthetic

<400> SEQUENCE: 80
agtaaaagac tcggatgatg tacctat                                         27

<210> SEQ ID NO 81
<211> LENGTH: 32
<212> TYPE: DNA
<213> ORGANISM: artificial
<220> FEATURE:
<223> OTHER INFORMATION: synthetic

<400> SEQUENCE: 81
acgttggatg acctatggtg ctagtgggaa ac                                   32

<210> SEQ ID NO 82
<211> LENGTH: 30
<212> TYPE: DNA
<213> ORGANISM: artificial
<220> FEATURE:
<223> OTHER INFORMATION: synthetic

<400> SEQUENCE: 82
acgttggatg tcccgttttt agggagcaga                                      30

<210> SEQ ID NO 83
<211> LENGTH: 20
<212> TYPE: DNA
<213> ORGANISM: artificial
<220> FEATURE:
<223> OTHER INFORMATION: synthetic

<400> SEQUENCE: 83
cccgttttta gggagcagat                                                 20

<210> SEQ ID NO 84
<211> LENGTH: 20
<212> TYPE: DNA
<213> ORGANISM: artificial
<220> FEATURE:
<223> OTHER INFORMATION: synthetic

<400> SEQUENCE: 84
```

-continued

```
cagttcgtgg gcttgttttg                                              20

<210> SEQ ID NO 85
<211> LENGTH: 20
<212> TYPE: DNA
<213> ORGANISM: artificial
<220> FEATURE:
<223> OTHER INFORMATION: synthetic

<400> SEQUENCE: 85
cttgcacaaa tgctgaaagc                                              20

<210> SEQ ID NO 86
<211> LENGTH: 21
<212> TYPE: DNA
<213> ORGANISM: artificial
<220> FEATURE:
<223> OTHER INFORMATION: synthetic

<400> SEQUENCE: 86
aaactggtgg tggttggagc a                                            21

<210> SEQ ID NO 87
<211> LENGTH: 48
<212> TYPE: DNA
<213> ORGANISM: artificial
<220> FEATURE:
<223> OTHER INFORMATION: synthetic

<400> SEQUENCE: 87
gttttcccag tcacgacacg ttggatgaaa ctggtggtgg ttggagca               48

<210> SEQ ID NO 88
<211> LENGTH: 19
<212> TYPE: DNA
<213> ORGANISM: artificial
<220> FEATURE:
<223> OTHER INFORMATION: synthetic

<400> SEQUENCE: 88
ggtggtggtt ggagcaggt                                               19

<210> SEQ ID NO 89
<211> LENGTH: 46
<212> TYPE: DNA
<213> ORGANISM: artificial
<220> FEATURE:
<223> OTHER INFORMATION: synthetic

<400> SEQUENCE: 89
gttttcccag tcacgacacg ttggatgggt ggtggttgga gcaggt                 46

<210> SEQ ID NO 90
<211> LENGTH: 22
<212> TYPE: DNA
<213> ORGANISM: artificial
<220> FEATURE:
<223> OTHER INFORMATION: synthetic

<400> SEQUENCE: 90 acaccccag gattcttaca ga                                            22

<210> SEQ ID NO 91
<211> LENGTH: 49
<212> TYPE: DNA
```

```
<213> ORGANISM: artificial
<220> FEATURE:
<223> OTHER INFORMATION: synthetic

<400> SEQUENCE: 91
gttttcccag tcacgacacg ttggatgaca cccccaggat tcttacaga            49

<210> SEQ ID NO 92
<211> LENGTH: 23
<212> TYPE: DNA
<213> ORGANISM: artificial
<220> FEATURE:
<223> OTHER INFORMATION: synthetic

<400> SEQUENCE: 92
atggcactgt actcttcttg tcc                                        23

<210> SEQ ID NO 93
<211> LENGTH: 50
<212> TYPE: DNA
<213> ORGANISM: artificial
<220> FEATURE:
<223> OTHER INFORMATION: synthetic

<400> SEQUENCE: 93
caggaaacag ctatgacacg ttggatgatg gcactgtact cttcttgtcc            50

<210> SEQ ID NO 94
<211> LENGTH: 25
<212> TYPE: DNA
<213> ORGANISM: artificial
<220> FEATURE:
<223> OTHER INFORMATION: synthetic

<400> SEQUENCE: 94
gttggacata ctggatacag ctgga                                      25

<210> SEQ ID NO 95
<211> LENGTH: 52
<212> TYPE: DNA
<213> ORGANISM: artificial
<220> FEATURE:
<223> OTHER INFORMATION: synthetic

<400> SEQUENCE: 95
gttttcccag tcacgacacg ttggatggtt ggacatactg gatacagctg ga        52

<210> SEQ ID NO 96
<211> LENGTH: 20
<212> TYPE: DNA
<213> ORGANISM: artificial
<220> FEATURE:
<223> OTHER INFORMATION: synthetic

<400> SEQUENCE: 96
ccgcaaatga cttgctatta                                            20

<210> SEQ ID NO 97
<211> LENGTH: 47
<212> TYPE: DNA
<213> ORGANISM: artificial
<220> FEATURE:
<223> OTHER INFORMATION: synthetic

<400> SEQUENCE: 97
caggaaacag ctatgacacg ttggatgccg caaatgactt gctatta              47
```

<210> SEQ ID NO 98
<211> LENGTH: 21
<212> TYPE: DNA
<213> ORGANISM: artificial
<220> FEATURE:
<223> OTHER INFORMATION: synthetic

<400> SEQUENCE: 98
acacactggt aagagaaata c                                              21

<210> SEQ ID NO 99
<211> LENGTH: 18
<212> TYPE: DNA
<213> ORGANISM: artificial
<220> FEATURE:
<223> OTHER INFORMATION: synthetic

<400> SEQUENCE: 99
ctgagtccca tcatcact                                                  18

<210> SEQ ID NO 100
<211> LENGTH: 24
<212> TYPE: DNA
<213> ORGANISM: artificial
<220> FEATURE:
<223> OTHER INFORMATION: synthetic

<400> SEQUENCE: 100
atcgagattt cactgtagct agac                                           24

<210> SEQ ID NO 101
<211> LENGTH: 19
<212> TYPE: DNA
<213> ORGANISM: artificial
<220> FEATURE:
<223> OTHER INFORMATION: synthetic

<400> SEQUENCE: 101
acttcaggca gcgtcttca                                                 19

<210> SEQ ID NO 102
<211> LENGTH: 19
<212> TYPE: DNA
<213> ORGANISM: artificial
<220> FEATURE:
<223> OTHER INFORMATION: synthetic

<400> SEQUENCE: 102
tgttcagagc acacttcag                                                 19

<210> SEQ ID NO 103
<211> LENGTH: 19
<212> TYPE: DNA
<213> ORGANISM: artificial
<220> FEATURE:
<223> OTHER INFORMATION: synthetic

<400> SEQUENCE: 103
ctggtggttg aatttgctg                                                 19

<210> SEQ ID NO 104
<211> LENGTH: 22
<212> TYPE: DNA
<213> ORGANISM: artificial
<220> FEATURE:

```
<223> OTHER INFORMATION: synthetic

<400> SEQUENCE: 104
catgagctcc agcaggatga ac                                          22

<210> SEQ ID NO 105
<211> LENGTH: 19
<212> TYPE: DNA
<213> ORGANISM: artificial
<220> FEATURE:
<223> OTHER INFORMATION: synthetic

<400> SEQUENCE: 105
ccgaagtctc caatcttgg                                              19

<210> SEQ ID NO 106
<211> LENGTH: 19
<212> TYPE: DNA
<213> ORGANISM: artificial
<220> FEATURE:
<223> OTHER INFORMATION: synthetic

<400> SEQUENCE: 106
tagatgtctc gggccatcc                                              19

<210> SEQ ID NO 107
<211> LENGTH: 15
<212> TYPE: DNA
<213> ORGANISM: artificial
<220> FEATURE:
<223> OTHER INFORMATION: synthetic

<400> SEQUENCE: 107
gggacactct aagat                                                  15

<210> SEQ ID NO 108
<211> LENGTH: 18
<212> TYPE: DNA
<213> ORGANISM: artificial
<220> FEATURE:
<223> OTHER INFORMATION: synthetic

<400> SEQUENCE: 108
ttctgtcctg ggattctc                                               18

<210> SEQ ID NO 109
<211> LENGTH: 18
<212> TYPE: DNA
<213> ORGANISM: artificial
<220> FEATURE:
<223> OTHER INFORMATION: synthetic

<400> SEQUENCE: 109
agattttcca cttgctgt                                               18

<210> SEQ ID NO 110
<211> LENGTH: 25
<212> TYPE: DNA
<213> ORGANISM: artificial
<220> FEATURE:
<223> OTHER INFORMATION: synthetic

<400> SEQUENCE: 110
ccagatggga cactctaaga ttttc                                       25
```

```
<210> SEQ ID NO 111
<211> LENGTH: 23
<212> TYPE: DNA
<213> ORGANISM: artificial
<220> FEATURE:
<223> OTHER INFORMATION: synthetic

<400> SEQUENCE: 111
cctttctgtc ctgggattct ctt                                            23

<210> SEQ ID NO 112
<211> LENGTH: 26
<212> TYPE: DNA
<213> ORGANISM: artificial
<220> FEATURE:
<223> OTHER INFORMATION: synthetic

<400> SEQUENCE: 112
gacagatttt ccacttgctg tgctaa                                         26

<210> SEQ ID NO 113
<211> LENGTH: 22
<212> TYPE: DNA
<213> ORGANISM: artificial
<220> FEATURE:
<223> OTHER INFORMATION: synthetic

<400> SEQUENCE: 113
cataaaggac actgtgaagg cc                                             22

<210> SEQ ID NO 114
<211> LENGTH: 22
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(22)
<223> OTHER INFORMATION: D-Lysine modified

<400> SEQUENCE: 114
ggccttcaca gtgtccttta tg                                             22

<210> SEQ ID NO 115
<211> LENGTH: 22
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(22)
<223> OTHER INFORMATION: D-Lysine modified

<400> SEQUENCE: 115
cattcttgat gtctctggct ag                                             22

<210> SEQ ID NO 116
<211> LENGTH: 14
<212> TYPE: DNA
<213> ORGANISM: artificial
<220> FEATURE:
<223> OTHER INFORMATION: synthetic

<400> SEQUENCE: 116
gagcccagca cttt                                                      14
```

```
<210> SEQ ID NO 117
<211> LENGTH: 19
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(19)
<223> OTHER INFORMATION: D-Lysine modified

<400> SEQUENCE: 117
cggagcccag cactttgat                                              19

<210> SEQ ID NO 118
<211> LENGTH: 19
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(19)
<223> OTHER INFORMATION: D-Lysine modified

<400> SEQUENCE: 118
cggagcccag cactttgat                                              19

<210> SEQ ID NO 119
<211> LENGTH: 18
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(18)
<223> OTHER INFORMATION: Amino and carboxamido modified

<400> SEQUENCE: 119
agatgttgct tctcttaa                                               18

<210> SEQ ID NO 120
<211> LENGTH: 18
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(18)
<223> OTHER INFORMATION: D-Lysine modified

<400> SEQUENCE: 120
agatgttgct tctcttaa                                               18

<210> SEQ ID NO 121
<211> LENGTH: 25
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(25)
<223> OTHER INFORMATION: D-Lysine modified

<400> SEQUENCE: 121
cggagatgtt gcttctctta attcc                                       25
```

```
<210> SEQ ID NO 122
<211> LENGTH: 16
<212> TYPE: DNA
<213> ORGANISM: artificial
<220> FEATURE:
<223> OTHER INFORMATION: synthetic

<400> SEQUENCE: 122
cagtttggcc agccca                                                       16

<210> SEQ ID NO 123
<211> LENGTH: 16
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(16)
<223> OTHER INFORMATION: D-Lysine modified

<400> SEQUENCE: 123
cagtttggcc agccca                                                       16

<210> SEQ ID NO 124
<211> LENGTH: 21
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(21)
<223> OTHER INFORMATION: D-Lysine modified

<400> SEQUENCE: 124
tttggccagc ccaaaatctg t                                                 21

<210> SEQ ID NO 125
<211> LENGTH: 18
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(18)
<223> OTHER INFORMATION: D-Lysine modified

<400> SEQUENCE: 125
ggccagccca aaatctgt                                                     18

<210> SEQ ID NO 126
<211> LENGTH: 15
<212> TYPE: DNA
<213> ORGANISM: artificial
<220> FEATURE:
<223> OTHER INFORMATION: synthetic

<400> SEQUENCE: 126
acccagcagt ttggc                                                        15

<210> SEQ ID NO 127
<211> LENGTH: 15
<212> TYPE: DNA
<213> ORGANISM: artificial
<220> FEATURE:
```

```
<223> OTHER INFORMATION: synthetic
<220> FEATURE:
<221> NAME/KEY: modified_base
<222> LOCATION: (1)..(15)
<223> OTHER INFORMATION: D-Lysine modified

<400> SEQUENCE: 127
acccagcagt ttggc                                                     15

<210> SEQ ID NO 128
<211> LENGTH: 13
<212> TYPE: DNA
<213> ORGANISM: artificial
<220> FEATURE:
<223> OTHER INFORMATION: synthetic

<400> SEQUENCE: 128
gctgcgtgat gag                                                       13

<210> SEQ ID NO 129
<211> LENGTH: 12
<212> TYPE: DNA
<213> ORGANISM: artificial
<220> FEATURE:
<223> OTHER INFORMATION: synthetic

<400> SEQUENCE: 129
gctgcgtgat ga                                                        12

<210> SEQ ID NO 130
<211> LENGTH: 20
<212> TYPE: DNA
<213> ORGANISM: artificial
<220> FEATURE:
<223> OTHER INFORMATION: synthetic

<400> SEQUENCE: 130
agctcatcac gcagctcatg                                                20

<210> SEQ ID NO 131
<211> LENGTH: 22
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(22)
<223> OTHER INFORMATION: D-Lysine modified

<400> SEQUENCE: 131
cagctcatca cgcagctcat gc                                             22

<210> SEQ ID NO 132
<211> LENGTH: 22
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(22)
<223> OTHER INFORMATION: D-Lysine modified

<400> SEQUENCE: 132
tcatcacgca gctcatgccc tt                                             22
```

```
<210> SEQ ID NO 133
<211> LENGTH: 18
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(18)
<223> OTHER INFORMATION: D-Lysine modified

<400> SEQUENCE: 133
ctcatcacgc agctcatg                                              18

<210> SEQ ID NO 134
<211> LENGTH: 14
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(14)
<223> OTHER INFORMATION: D-Lysine modified

<400> SEQUENCE: 134
tgagctgcgt gatg                                                  14

<210> SEQ ID NO 135
<211> LENGTH: 20
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(20)
<223> OTHER INFORMATION: D-Lysine modified

<400> SEQUENCE: 135
tccacgctgg ccatcacgta                                            20

<210> SEQ ID NO 136
<211> LENGTH: 20
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(20)
<223> OTHER INFORMATION: D-Lysine modified

<400> SEQUENCE: 136
tccacgctgg ccatcacgta                                            20

<210> SEQ ID NO 137
<211> LENGTH: 14
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(14)
<223> OTHER INFORMATION: D-Lysine modified

<400> SEQUENCE: 137
tgggggttgt ccac                                                  14
```

<210> SEQ ID NO 138
<211> LENGTH: 15
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(15)
<223> OTHER INFORMATION: D-Lysine modified

<400> SEQUENCE: 138
gcacacgtgg gggtt                                                    15

<210> SEQ ID NO 139
<211> LENGTH: 17
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(17)
<223> OTHER INFORMATION: D-Lysine modified

<400> SEQUENCE: 139 acaacccccca cgtgtgc                                                 17

<210> SEQ ID NO 140
<211> LENGTH: 16
<212> TYPE: DNA
<213> ORGANISM: artificial
<220> FEATURE:
<223> OTHER INFORMATION: synthetic

<400> SEQUENCE: 140
ctgagccagg agaaac                                                   16

<210> SEQ ID NO 141
<211> LENGTH: 17
<212> TYPE: DNA
<213> ORGANISM: artificial
<220> FEATURE:
<223> OTHER INFORMATION: synthetic

<400> SEQUENCE: 141
gtaaactgag ccaggag                                                  17

<210> SEQ ID NO 142
<211> LENGTH: 20
<212> TYPE: DNA
<213> ORGANISM: artificial
<220> FEATURE:
<223> OTHER INFORMATION: synthetic

<400> SEQUENCE: 142
atggcactag taaactgagc                                               20

<210> SEQ ID NO 143
<211> LENGTH: 21
<212> TYPE: DNA
<213> ORGANISM: artificial
<220> FEATURE:
<223> OTHER INFORMATION: synthetic

<400> SEQUENCE: 143
atccatataa ctgaaagcca a                                             21

<210> SEQ ID NO 144
<211> LENGTH: 23
<212> TYPE: DNA
<213> ORGANISM: artificial
<220> FEATURE:
<223> OTHER INFORMATION: synthetic

<400> SEQUENCE: 144
accacatcat ccatataact gaa                                          23

<210> SEQ ID NO 145
<211> LENGTH: 17
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(17)
<223> OTHER INFORMATION: D-Lysine modified

<400> SEQUENCE: 145
ttgcccacac cgccggc                                                 17

<210> SEQ ID NO 146
<211> LENGTH: 16
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(16)
<223> OTHER INFORMATION: D-Lysine modified

<400> SEQUENCE: 146
tcttgcccac accgcc                                                  16

<210> SEQ ID NO 147
<211> LENGTH: 17
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(17)
<223> OTHER INFORMATION: D-Lysine modified

<400> SEQUENCE: 147
tactcctcct ggccggc                                                 17

<210> SEQ ID NO 148
<211> LENGTH: 23
<212> TYPE: DNA
<213> ORGANISM: artificial
<220> FEATURE:
<223> OTHER INFORMATION: synthetic

<400> SEQUENCE: 148
cgtctccaca gacacatact cca                                          23

<210> SEQ ID NO 149
<211> LENGTH: 23
<212> TYPE: DNA
<213> ORGANISM: artificial
<220> FEATURE:

<223> OTHER INFORMATION: synthetic
<220> FEATURE:
<221> NAME/KEY: modified_base
<222> LOCATION: (1)..(23)
<223> OTHER INFORMATION: D-Lysine modified

<400> SEQUENCE: 149
cgtctccaca gacacatact cca                                          23

<210> SEQ ID NO 150
<211> LENGTH: 21
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(21)
<223> OTHER INFORMATION: D-Lysine modified

<400> SEQUENCE: 150
gcctacgcca ccagctccaa c                                            21

<210> SEQ ID NO 151
<211> LENGTH: 21
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(21)
<223> OTHER INFORMATION: D-Lysine modified

<400> SEQUENCE: 151
gcctacgcca ccagctccaa c                                            21

<210> SEQ ID NO 152
<211> LENGTH: 24
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(24)
<223> OTHER INFORMATION: D-Lysine modified

<400> SEQUENCE: 152
ctacgccacc agctccaact acca                                         24

<210> SEQ ID NO 153
<211> LENGTH: 24
<212> TYPE: DNA
<213> ORGANISM: artificial
<220> FEATURE:
<223> OTHER INFORMATION: synthetic

<400> SEQUENCE: 153
ctacgccacc agctccaact acca                                         24

<210> SEQ ID NO 154
<211> LENGTH: 23
<212> TYPE: DNA
<213> ORGANISM: artificial
<220> FEATURE:
<223> OTHER INFORMATION: synthetic

<400> SEQUENCE: 154

```
tcttgcctac gccaccagct cca                                              23
```

<210> SEQ ID NO 155
<211> LENGTH: 23
<212> TYPE: DNA
<213> ORGANISM: artificial
<220> FEATURE:
<223> OTHER INFORMATION: synthetic

<400> SEQUENCE: 155

```
tgtactcctc ttgacctgct gtg                                              23
```

<210> SEQ ID NO 156
<211> LENGTH: 23
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(23)
<223> OTHER INFORMATION: D-Lysine modified

<400> SEQUENCE: 156

```
tgtactcctc ttgacctgct gtg                                              23
```

<210> SEQ ID NO 157
<211> LENGTH: 23
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(23)
<223> OTHER INFORMATION: Amino and carboxamido modified

<400> SEQUENCE: 157

```
ggcaaatcac atttatttcc tac                                              23
```

<210> SEQ ID NO 158
<211> LENGTH: 23
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(23)
<223> OTHER INFORMATION: D-Lysine modified

<400> SEQUENCE: 158

```
ggcaaatcac atttatttcc tac                                              23
```

<210> SEQ ID NO 159
<211> LENGTH: 23
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(23)
<223> OTHER INFORMATION: D-Lysine modified

<400> SEQUENCE: 159

```
tgtcttgtct ttgctgatgt ttc                                              23
```

```
<210> SEQ ID NO 160
<211> LENGTH: 23
<212> TYPE: DNA
<213> ORGANISM: artificial
<220> FEATURE:
<223> OTHER INFORMATION: synthetic

<400> SEQUENCE: 160
tgtcttgtct ttgctgatgt ttc                                              23

<210> SEQ ID NO 161
<211> LENGTH: 23
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(23)
<223> OTHER INFORMATION: D-Lysine modified

<400> SEQUENCE: 161
tgtcttgtct ttgctgatgt ttc                                              23

<210> SEQ ID NO 162
<211> LENGTH: 21
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(21)
<223> OTHER INFORMATION: Amino and carboxy amido modified

<400> SEQUENCE: 162
ctcttgacct gctgtgtcga g                                                21

<210> SEQ ID NO 163
<211> LENGTH: 21
<212> TYPE: DNA
<213> ORGANISM: artificial
<220> FEATURE:
<223> OTHER INFORMATION: synthetic

<400> SEQUENCE: 163
tcccaacacc acctgctcca a                                                21

<210> SEQ ID NO 164
<211> LENGTH: 25
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(25)
<223> OTHER INFORMATION: D-Lysine modified

<400> SEQUENCE: 164
caacaccacc tgctccaacc accac                                            25

<210> SEQ ID NO 165
<211> LENGTH: 23
<212> TYPE: DNA
<213> ORGANISM: artificial
<220> FEATURE:
<223> OTHER INFORMATION: synthetic
```

-continued

<400> SEQUENCE: 165
cttttcccaa caccacctgc tcc                                              23

<210> SEQ ID NO 166
<211> LENGTH: 25
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(25)
<223> OTHER INFORMATION: D-Lysine modified

<400> SEQUENCE: 166
tgcgcttttc ccaacaccac ctgct                                            25

<210> SEQ ID NO 167
<211> LENGTH: 23
<212> TYPE: DNA
<213> ORGANISM: artificial
<220> FEATURE:
<223> OTHER INFORMATION: synthetic

<400> SEQUENCE: 167
ggcactgtac tcttcttgtc cag                                              23

<210> SEQ ID NO 168
<211> LENGTH: 21
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(21)
<223> OTHER INFORMATION: D-Lysine modified

<400> SEQUENCE: 168
tctggtcttg gctgaggttt c                                                21

<210> SEQ ID NO 169
<211> LENGTH: 23
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(23)
<223> OTHER INFORMATION: Amino and carboxamido modified

<400> SEQUENCE: 169
ggcaaatcac acttgtttcc cac                                              23

<210> SEQ ID NO 170
<211> LENGTH: 23
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(23)
<223> OTHER INFORMATION: D-Lysine modified

<400> SEQUENCE: 170
ggcaaatcac acttgtttcc cac                                            23

<210> SEQ ID NO 171
<211> LENGTH: 25
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(25)
<223> OTHER INFORMATION: Amino and carboxamido modified

<400> SEQUENCE: 171
ttcttgtcca gctgtatcca gtatg                                          25

<210> SEQ ID NO 172
<211> LENGTH: 21
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(21)
<223> OTHER INFORMATION: D-Lysine modified

<400> SEQUENCE: 172
agatcctctc tctgaaatca c                                              21

<210> SEQ ID NO 173
<211> LENGTH: 24
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(24)
<223> OTHER INFORMATION: D-Lysine modified

<400> SEQUENCE: 173
tctttctcct gctcagtgat ttca                                           24

<210> SEQ ID NO 174
<211> LENGTH: 23
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(23)
<223> OTHER INFORMATION: D-Lysine modified

<400> SEQUENCE: 174
aatgatgcac atcatggtgg ctg                                            23

<210> SEQ ID NO 175
<211> LENGTH: 23
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(23)
<223> OTHER INFORMATION: D-Lysine modified

<400> SEQUENCE: 175
ggcactgtac tcttcttgtc cag                                              23

<210> SEQ ID NO 176
<211> LENGTH: 26
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(26)
<223> OTHER INFORMATION: Amino modified

<400> SEQUENCE: 176
ttcatcaacc gcactctgtt tatctc                                           26

<210> SEQ ID NO 177
<211> LENGTH: 25
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(25)
<223> OTHER INFORMATION: Amino modified

<400> SEQUENCE: 177
tggcgacgac aatggaccca attat                                            25

<210> SEQ ID NO 178
<211> LENGTH: 30
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(30)
<223> OTHER INFORMATION: Amino modified

<400> SEQUENCE: 178
agatgtagtt agcaatcggt ccttgttgta                                       30

<210> SEQ ID NO 179
<211> LENGTH: 30
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(30)
<223> OTHER INFORMATION: Amino modified

<400> SEQUENCE: 179
gggtaattga ggtaacgtag gtatcaagat                                       30

<210> SEQ ID NO 180
<211> LENGTH: 27
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(27)
<223> OTHER INFORMATION: Amino modified

```
<400> SEQUENCE: 180
tactatcgac tgacatgagg cttgtgt                                          27

<210> SEQ ID NO 181
<211> LENGTH: 20
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(20)
<223> OTHER INFORMATION: D-Lysine modified

<400> SEQUENCE: 181
agtccgacga tctggaattc                                                  20

<210> SEQ ID NO 182
<211> LENGTH: 19
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(19)
<223> OTHER INFORMATION: D-Lysine modified

<400> SEQUENCE: 182
actggagttc agacgtgtg                                                   19

<210> SEQ ID NO 183
<211> LENGTH: 20
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(20)
<223> OTHER INFORMATION: D-Lysine modified

<400> SEQUENCE: 183
ctcttccgat cagatcggaa                                                  20

<210> SEQ ID NO 184
<211> LENGTH: 21
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(21)
<223> OTHER INFORMATION: D-Lysine modified

<400> SEQUENCE: 184
ctcttccgat cagatcggaa g                                                21

<210> SEQ ID NO 185
<211> LENGTH: 15
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(15)
<223> OTHER INFORMATION: D-Lysine modified
```

<400> SEQUENCE: 185
agcgctcccc gcacc                                                         15

<210> SEQ ID NO 186
<211> LENGTH: 15
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(15)
<223> OTHER INFORMATION: D-Lysine modified

<400> SEQUENCE: 186
agcgctcccc gcacc                                                         15

<210> SEQ ID NO 187
<211> LENGTH: 14
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(14)
<223> OTHER INFORMATION: D-Lysine modified

<400> SEQUENCE: 187
ggggagcgct ctgt                                                          14

<210> SEQ ID NO 188
<211> LENGTH: 15
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(15)
<223> OTHER INFORMATION: D-Lysine modified

<400> SEQUENCE: 188
agcgctcccc gcacc                                                         15

<210> SEQ ID NO 189
<211> LENGTH: 20
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(20)
<223> OTHER INFORMATION: D-Lysine modified

<400> SEQUENCE: 189
tgcatacaca ctgcccgcct                                                    20

<210> SEQ ID NO 190
<211> LENGTH: 360
<212> TYPE: DNA
<213> ORGANISM: Homo sapiens

<400> SEQUENCE: 190
tagaaattag atctcttacc taaactcttc ataatgcttg ctctgatagg aaaatgagat        60

```
ctactgtttt cctttactta ctacacctca gatatatttc ttcatgaaga cctcacagta        120
aaaataggtg attttggtct agctacagtg aaatctcgat ggagtgggtc ccatcagttt        180
gaacagttgt ctggatccat tttgtggatg gtaagaattg aggctatttt ccactgatt         240 aaattttttgg ccctgagatg ctgctgagtt actagaaagt cattgaaggt ctcaactata      300
gtattttcat agttcccagt attcacaaaa atcagtgttc ttatttttta tgtaaataga       360
```

<210> SEQ ID NO 191
<211> LENGTH: 480
<212> TYPE: DNA
<213> ORGANISM: Homo sapiens

<400> SEQUENCE: 191

```
tagagaaggc gtacatttgt ccttccaaat gagctggcaa gtgccgtgtc ctggcaccca        60
agcccatgcc gtggctgctg gtccccctgc tgggccatgt ctggcactgc tttccagcat       120
ggtgagggct gaggtgaccc ttgtctctgt gttcttgtcc cccccagctt gtggagcctc       180
ttacacccag tggagaagct cccaaccaag ctctcttgag gatcttgaag gaaactgaat       240
tcaaaaagat caaagtgctg ggctccggtg cgttcggcac ggtgtataag gtaaggtccc       300
tggcacaggc ctctgggctg ggccgcaggg cctctcatgg tctggtgggg agcccagagt       360
ccttgcaagc tgtatatttc catcatctac tttactcttt gtttcactga gtgtttggga       420
aactccagtt ttttccccaa gttattgaga ggaaatcttt tataaccaca gtaatcagtg       480
```

<210> SEQ ID NO 192
<211> LENGTH: 420
<212> TYPE: DNA
<213> ORGANISM: Homo sapiens

<400> SEQUENCE: 192

```
agcccaacag ctgcagggct gcgggggcgt cacagccccc agcaatatca gccttaggtg        60
cggctccaca gccccagtgt ccctcacctt cggggtgcat cgctggtaac atccacccag       120
atcactgggc agcatgtggc accatctcac aattgccagt taacgtcttc cttctctctc       180
tgtcataggg actctggatc ccagaaggtg agaaagttaa aattcccgtc gctatcaagg       240
aattaagaga agcaacatct ccgaaagcca acaaggaaat cctcgatgtg agtttctgct       300
ttgctgtgtg ggggtccatg gctctgaacc tcaggcccac cttttctcat gtctggcagc       360
tgctctgctc tagaccctgc tcatctccac atcctaaatg ttcactttct atgtctttcc       420
```

<210> SEQ ID NO 193
<211> LENGTH: 480
<212> TYPE: DNA
<213> ORGANISM: Homo sapiens

<400> SEQUENCE: 193

```
aaaattcccg tcgctatcaa ggaattaaga gaagcaacat ctccgaaagc caacaaggaa        60
atcctcgatg aagcctacgt gatggccagc gtggacaacc ccacgtgtg ccgcctgctg        120 ggcatctgcc tcacctccac cgtgcagctc atcacgcagc tcatgccctt cggctgcctc       180
ctggactatg tccgggaaca caagacaat attggctccc agtacctgct caactggtgt       240
gtgcagatcg caaagggcat gaactacttg gaggaccgtc gcttggtgca ccgcgacctg       300
gcagccagga acgtactggt gaaaacaccg cagcatgtca agatcacaga ttttgggctg       360
gccaaactgc tgggtgcgga agagaaagaa taccatgcag aaggaggcaa agtgcctatc       420
aagtggatgg cattggaatc aatttttacac agaatctata cccaccagag tgatgtctgg       480
```

<210> SEQ ID NO 194
<211> LENGTH: 420
<212> TYPE: DNA
<213> ORGANISM: Homo sapiens

<400> SEQUENCE: 194
ggcatctgcc tcacctccac cgtgcagctc atcacgcagc tcatgccctt cggctgcctc      60
ctggactatg tccgggaaca caagacaat attggctccc agtacctgct caactggtgt     120
gtgcagatcg caaagggcat gaactacttg gaggaccgtc gcttggtgca ccgcgacctg     180
gcagccagga acgtactggt gaaaacaccg cagcatgtca agatcacaga ttttgggctg     240
gccaaactgc tgggtgcgga agagaaagaa taccatgcag aaggaggcaa agtgcctatc     300
aagtggatgg cattggaatc aattttacac agaatctata cccaccagag tgatgtctgg     360
agctacgggg tgaccgtttg ggagttgatg acctttggat ccaagccata tgacggaatc     420

<210> SEQ ID NO 195
<211> LENGTH: 239
<212> TYPE: DNA
<213> ORGANISM: Homo sapiens

<400> SEQUENCE: 195
ctgcaggatt cctaccggaa gcaggtggtc attgatgggg agacgtgcct gttggacatc      60
ctggataccg ccggccagga ggagtacagc gccatgcggg accagtacat gcgcaccggg     120
gagggcttcc tgtgtgtgtt tgccatcaac aacaccaagt cttttgagga catccaccag     180
tacaggtgaa ccccgtgagg ctggcccggg agcccacgcc gcacaggtgg ggccaggcc      239

<210> SEQ ID NO 196
<211> LENGTH: 770
<212> TYPE: DNA
<213> ORGANISM: Homo sapiens

<400> SEQUENCE: 196
ctgacatcta cctctagttg tacttctgtc ctctatttca ggtgttatgg gtcaagcctg      60
tttgactggc attattcatg attcctgtac cactcttgct ctctctcact ttgatctcca     120
tattccaggc ttacacaggg gttcctcag aacgttgatg gcagttgcag gtccatataa     180
agggaccaaa gcacattgta tcctcatcta gtgtcatgct gaaagtagga gaaagtgcat     240
ctttattatg gcagagagaa ttttctgaac tatttatgga caacagtcaa acaacaattc     300
tttgtacttt ttttttttcct tagtctttct ttgaagcagc aagtatgatg agcaagcttt     360
ctcacaagca tttggtttta aattatggag tatgtgtctg tggagacgag agtaagtaaa     420
actacaggct ttctaatgcc tttctcagag catctgtttt tgtttatata gaaaattcag     480
tttcaggatc acagctaggt gtcagtgtaa actataattt aacaggagtt aagtattttt     540
gaaactgaaa acactgtagg actattcagt tatatcttgt gaaaaaggaa agcaatgaag     600
ttaaaagtag aaggttacaa tgcccaaaca atagagtatt atagtaaaca aatgtctata     660
aaacattttg tgttcatgat agcaaaagag attatggcag gttcaacata acattggaat     720
aactggccctt tcagtacaa acttatctgg aattatgaag acaaagcata              770

<210> SEQ ID NO 197
<211> LENGTH: 240
<212> TYPE: DNA
<213> ORGANISM: Homo sapiens

<400> SEQUENCE: 197

| | | | | |
|---|---|---|---|---|
| ggtactggtg | gagtatttga | tagtgtatta | accttatgtg | tgacatgttc taatatagtc | 60 |
| acattttcat | tatttttatt | ataaggcctg | ctgaaaatga | ctgaatataa acttgtggta | 120 |
| gttggagctg | gtggcgtagg | caagagtgcc | ttgacgatac | agctaattca gaatcatttt | 180 |
| gtggacgaat | atgatccaac | aatagaggta | aatcttgttt | taatatgcat attactggtg | 240 |

<210> SEQ ID NO 198
<211> LENGTH: 240
<212> TYPE: DNA
<213> ORGANISM: Homo sapiens

<400> SEQUENCE: 198

| | | | | |
|---|---|---|---|---|
| cttctcagga | ttcctacagg | aagcaagtag | taattgatgg | agaaacctgt ctcttggata | 60 |
| ttctcgacac | agcaggtcaa | gaggagtaca | gtgcaatgag | ggaccagtac atgaggactg | 120 |
| gggagggctt | tctttgtgta | tttgccataa | ataatactaa | atcatttgaa gatattcacc | 180 |
| attataggtg | ggtttaaatt | gaatataata | agctgacatt | aaggagtaat tatagttttt | 240 |

<210> SEQ ID NO 199
<211> LENGTH: 300
<212> TYPE: DNA
<213> ORGANISM: Homo sapiens

<400> SEQUENCE: 199

| | | | | |
|---|---|---|---|---|
| gtgctataac | ttttttttct | ttcccagaga | acaaattaaa | agagttaagg actctgaaga | 60 |
| tgtacctatg | gtcctagtag | gaaataaatg | tgatttgcct | tctagaacag tagacacaaa | 120 |
| acaggctcag | gacttagcaa | gaagttatgg | aattcctttt | attgaaacat cagcaaagac | 180 |
| aagacaggta | agtaacactg | aaataaatac | agatctgttt | tctgcaaaat cataactgtt | 240 |
| atgtcattta | atatatcagt | ttttctctca | attatgctat | actaggaaat aaaacaatat | 300 |

<210> SEQ ID NO 200
<211> LENGTH: 180
<212> TYPE: DNA
<213> ORGANISM: Homo sapiens

<400> SEQUENCE: 200

| | | | | |
|---|---|---|---|---|
| aatgcaacag | actttaaaga | agttgtgttt | tacaatgcag | agagtggagg atgcttttta | 60 |
| tacattggtg | agggagatcc | gacaatacag | attgaaaaaa | atcagcaaag aagaaaagac | 120 |
| tcctggctgt | gtgaaaatta | aaaaatgcat | tataatgtaa | tctggtaagt ttaagttcag | 180 |

<210> SEQ ID NO 201
<211> LENGTH: 480
<212> TYPE: DNA
<213> ORGANISM: Homo sapiens

<400> SEQUENCE: 201

| | | | | |
|---|---|---|---|---|
| gtgttttgc | gttctctagt | cactttaaga | accaaatgga | aggtcacact agggttttca | 60 |
| tttccattga | ttatagaaag | ctttaaagta | ctgtagatgt | ggctcgccaa ttaaccctga | 120 |
| ttactggttt | ccaacaggtt | cttgctggtg | tgaaatgact | gagtacaaac tggtggtggt | 180 |
| tggagcaggt | ggtgttggga | aaagcgcact | gacaatccag | ctaatccaga accactttgt | 240 |
| agatgaatat | gatcccacca | tagaggtgag | gcccagtggt | agcccgctga cctgatcctg | 300 |
| tctctcactt | gtcggatcat | ctttacccat | attctgtatt | aaaggaataa gaggagagaa | 360 |
| agtaaaaagt | tattttgggt | atacattcag | ttatgcaata | agcttaacgt gtttatagag | 420 |

```
aacagttcat ttttattagc tgctgaagtt tctaaaacct gtccagtttt taacagttct    480
```

<210> SEQ ID NO 202
<211> LENGTH: 480
<212> TYPE: DNA
<213> ORGANISM: Homo sapiens

<400> SEQUENCE: 202

```
tgggcttgaa tagttagatg cttatttaac cttggcaata gcattgcatt ccctgtggtt     60
tttaataaaa attgaacttc cctccctccc tgcccccttta ccctccacac ccccaggatt   120
cttacagaaa acaagtggtt atagatggtg aaacctgttt gttggacata ctggatacag   180
ctggacaaga agagtacagt gccatgagag accaatacat gaggacaggc gaaggcttcc   240
tctgtgtatt tgccatcaat aatagcaagt catttgcgga tattaacctc tacaggtact   300
aggagcatta ttttctctga aaggatgatc tttgtgttct gaatctttat ggggaaatga   360
ggttaccaca ctagggaaga tagagctttt taattatggg aagagttggt tttaggttgt   420
ttgacattga gaatctaggg taattactga aagttaatac tggaatttat tttacataat   480
```

<210> SEQ ID NO 203
<211> LENGTH: 420
<212> TYPE: DNA
<213> ORGANISM: Homo sapiens

<400> SEQUENCE: 203

```
tggatacagc tggacaagaa gagtacagtg ccatgagaga ccaatacatg aggacaggcg     60
aaggcttcct ctgtgtattt gccatcaata atagcaagtc atttgcggat attaacctct   120
acagggagca gattaagcga gtaaaagact cggatgatgt acctatggtg ctagtgggaa   180
acaagtgtga tttgccaaca aggacagttg atacaaaaca gcccacgaa ctggccaaga    240
gttacgggat tccattcatt gaaacctcag ccaagaccag acagggtgtt gaagatgctt   300
tttacacact ggtaagagaa atacgccagt accgaatgaa aaaactcaac agcagtgatg   360
atgggactca gggttgtatg ggattgccat gtgtggtgat gtaacaagat acttttaaag   420
```

<210> SEQ ID NO 204
<211> LENGTH: 360
<212> TYPE: DNA
<213> ORGANISM: Homo sapiens

<400> SEQUENCE: 204

```
tgtaaaattt attgaaaatg tatttgcttt ttctgtaaat catctgtgaa tccagagggg     60
aaaaatatga caaagaaagc tatataagat attatttat tttacagagt aacagactag    120
ctagagacaa tgaattaagg gaaaatgaca agaacagct caaagcaatt tctacacgag    180
atcctctctc tgaaatcact gagcaggaga aagatttct atggagtcac aggtaagtgc    240
taaaatggag attctctgtt tcttttttctt tattacagaa aaaataactg aatttggctg   300
atctcagcat gttttttacca tacctattgg aataaataaa gcagaattta catgattttt   360
```

<210> SEQ ID NO 205
<211> LENGTH: 300
<212> TYPE: DNA
<213> ORGANISM: Homo sapiens

<400> SEQUENCE: 205

```
tagctattcg acagcatgcc aatctcttca taaatctttt ctcaatgatg cttggctctg     60
```

```
gaatgccaga actacaatct tttgatgaca ttgcatacat tcgaaagacc ctagccttag    120
ataaaactga gcaagaggct ttggagtatt tcatgaaaca aatgaatgat gcacatcatg    180
gtggctggac aacaaaaatg gattggatct tccacacaat taaacagcat gcattgaact    240
gaaaagataa ctgagaaaat gaaagctcac tctggattcc acactgcact gttaataact    300
```

<210> SEQ ID NO 206
<211> LENGTH: 490
<212> TYPE: DNA
<213> ORGANISM: Homo sapiens

<400> SEQUENCE: 206

```
gttgtaaatc tttgtaacac ttcaaaaagc tatattgtat ttatatttta aaataaattt     60
cagggtaaaa taataataaa gcaaaggtac ctagtaaagt ttttaactat tttaaaggct    120
tgaagagtgt cgaattatgt cctctgcaaa aaggccactg tggttgaatt gggagaaccc    180
agacatcatg tcagagttac tgtttcagaa caatgagatc atctttaaaa atggggatgg    240
taaggaagag tattaatgag cttatgatgc atgaatttag ctatcttttt atacacagga    300
tatttatgaa ccatgaaaac tactgaaagc catttaagga atatacacat gtgataaaat    360
atgtaatatt tatcagatgt cttgaccttt gaaatatgca tgtataatca atgaaaagaa    420
aagaagtact aggtttagat cagaagtcct gaaatcagtt ttttgttttt tcttttttcct   480 gttccctgcc                                                          490
```

<210> SEQ ID NO 207
<211> LENGTH: 19
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(19)
<223> OTHER INFORMATION: D-Lysine, oxy-aza and aza-aza modified

<400> SEQUENCE: 207

```
cggagcccag cactttgat                                                 19
```

<210> SEQ ID NO 208
<211> LENGTH: 25
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(25)
<223> OTHER INFORMATION: D-Lysine, oxy-aza and aza-aza modified

<400> SEQUENCE: 208

```
cggagatgtt gcttctctta attcc                                          25
```

<210> SEQ ID NO 209
<211> LENGTH: 14
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(14)
<223> OTHER INFORMATION: D-Lysine, oxy-aza and aza-aza modified

<400> SEQUENCE: 209
tcatcacgca gctc                                                         14

<210> SEQ ID NO 210
<211> LENGTH: 18
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(18)
<223> OTHER INFORMATION: D-Lysine, oxy-aza and aza-aza modified

<400> SEQUENCE: 210
ggccagccca aaatctgt                                                     18

<210> SEQ ID NO 211
<211> LENGTH: 25
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(25)
<223> OTHER INFORMATION: D-Lysine, oxy-aza and aza-aza modified

<400> SEQUENCE: 211
caacaccacc tgctccaacc accac                                             25

<210> SEQ ID NO 212
<211> LENGTH: 25
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(25)
<223> OTHER INFORMATION: D-Lysine, oxy-aza and aza-aza modified

<400> SEQUENCE: 212
ttcttgtcca gctgtatcca gtatg                                             25

<210> SEQ ID NO 213
<211> LENGTH: 24
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(24)
<223> OTHER INFORMATION: D-Lysine, oxy-aza and aza-aza modified

<400> SEQUENCE: 213
ctacgccacc agctccaact acca                                              24

<210> SEQ ID NO 214
<211> LENGTH: 21
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(21)
<223> OTHER INFORMATION: D-Lysine, oxy-aza and aza-aza modified

<400> SEQUENCE: 214
ctcttgacct gctgtgtcga g    21

<210> SEQ ID NO 215
<211> LENGTH: 15
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(15)
<223> OTHER INFORMATION: D-Lysine, oxy-aza and aza-aza modified

<400> SEQUENCE: 215
tgtctttgct gatgt    15

<210> SEQ ID NO 216
<211> LENGTH: 24
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(24)
<223> OTHER INFORMATION: D-Lysine, oxy-aza and aza-aza modified

<400> SEQUENCE: 216
ctgacctagt tccaatcttt tctt    24

<210> SEQ ID NO 217
<211> LENGTH: 23
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(23)
<223> OTHER INFORMATION: D-Lysine, oxy-aza and aza-aza modified

<400> SEQUENCE: 217
aatgatgcac atcatggtgg ctg    23

<210> SEQ ID NO 218
<211> LENGTH: 15
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(15)
<223> OTHER INFORMATION: D-Lysine, oxy-aza and aza-aza modified

<400> SEQUENCE: 218
ctccttctct gagtg    15

<210> SEQ ID NO 219
<211> LENGTH: 24
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(24)
<223> OTHER INFORMATION: D-Lysine, oxy-aza and aza-aza modified -continued

<400> SEQUENCE: 219
atcgagattt cactgtagct agac                                              24

<210> SEQ ID NO 220
<211> LENGTH: 44
<212> TYPE: DNA
<213> ORGANISM: artificial
<220> FEATURE:
<223> OTHER INFORMATION: synthetic

<400> SEQUENCE: 220
cctacacgac gctcttccga tctagcaaca gtcttacctg gact                        44

<210> SEQ ID NO 221
<211> LENGTH: 46
<212> TYPE: DNA
<213> ORGANISM: artificial
<220> FEATURE:
<223> OTHER INFORMATION: synthetic

<400> SEQUENCE: 221
ttcagacgtg tgctcttccg atctgggagg tatccacatc ctcttc                      46

<210> SEQ ID NO 222
<211> LENGTH: 55
<212> TYPE: DNA
<213> ORGANISM: artificial
<220> FEATURE:
<223> OTHER INFORMATION: synthetic

<400> SEQUENCE: 222
cctacacgac gctcttccga tctgtattta tttcagtgtt acttacctgt cttgt            55

<210> SEQ ID NO 223
<211> LENGTH: 50
<212> TYPE: DNA
<213> ORGANISM: artificial
<220> FEATURE:
<223> OTHER INFORMATION: synthetic

<400> SEQUENCE: 223
ttcagacgtg tgctcttccg atctaagatg tacctatggt cctagtagga                  50

<210> SEQ ID NO 224
<211> LENGTH: 49
<212> TYPE: DNA
<213> ORGANISM: artificial
<220> FEATURE:
<223> OTHER INFORMATION: synthetic

<400> SEQUENCE: 224
cctacacgac gctcttccga tctcctgtag aggttaatat ccgcaaatg                   49

<210> SEQ ID NO 225
<211> LENGTH: 51
<212> TYPE: DNA
<213> ORGANISM: artificial
<220> FEATURE:
<223> OTHER INFORMATION: synthetic

<400> SEQUENCE: 225
ttcagacgtg tgctcttccg atctgttata gatggtgaaa cctgtttgtt g                51

<210> SEQ ID NO 226

```
<211> LENGTH: 51
<212> TYPE: DNA
<213> ORGANISM: artificial
<220> FEATURE:
<223> OTHER INFORMATION: synthetic

<400> SEQUENCE: 226
cctacacgac gctcttccga tcttgggatc atattcatct acaaagtggt t          51

<210> SEQ ID NO 227
<211> LENGTH: 48
<212> TYPE: DNA
<213> ORGANISM: artificial
<220> FEATURE:
<223> OTHER INFORMATION: synthetic

<400> SEQUENCE: 227
ttcagacgtg tgctcttccg atctttactg gtttccaaca ggttcttg             48

<210> SEQ ID NO 228
<211> LENGTH: 46
<212> TYPE: DNA
<213> ORGANISM: artificial
<220> FEATURE:
<223> OTHER INFORMATION: synthetic

<400> SEQUENCE: 228
cctacacgac gctcttccga tctctctgga atgccagaac tacaat               46

<210> SEQ ID NO 229
<211> LENGTH: 50
<212> TYPE: DNA
<213> ORGANISM: artificial
<220> FEATURE:
<223> OTHER INFORMATION: synthetic

<400> SEQUENCE: 229
ttcagacgtg tgctcttccg atctgtggaa gatccaatcc attttttgttg          50

<210> SEQ ID NO 230
<211> LENGTH: 47
<212> TYPE: DNA
<213> ORGANISM: artificial
<220> FEATURE:
<223> OTHER INFORMATION: synthetic

<400> SEQUENCE: 230
cctacacgac gctcttccga tctcaggaag cagattctgc taatacc              47

<210> SEQ ID NO 231
<211> LENGTH: 49
<212> TYPE: DNA
<213> ORGANISM: artificial
<220> FEATURE:
<223> OTHER INFORMATION: synthetic

<400> SEQUENCE: 231
ttcagacgtg tgctcttccg atctaagata aactagaacc ctgcagtct            49

<210> SEQ ID NO 232
<211> LENGTH: 45
<212> TYPE: DNA
<213> ORGANISM: artificial
<220> FEATURE:
<223> OTHER INFORMATION: synthetic

<400> SEQUENCE: 232
```

-continued

```
cctacacgac gctcttccga tctccttgtc tctgtgttct tgtcc        45
```

<210> SEQ ID NO 233
<211> LENGTH: 43
<212> TYPE: DNA
<213> ORGANISM: artificial
<220> FEATURE:
<223> OTHER INFORMATION: synthetic

<400> SEQUENCE: 233

```
ttcagacgtg tgctcttccg atcttataca ccgtgccgaa cgc          43
```

<210> SEQ ID NO 234
<211> LENGTH: 48
<212> TYPE: DNA
<213> ORGANISM: artificial
<220> FEATURE:
<223> OTHER INFORMATION: synthetic

<400> SEQUENCE: 234

```
cctacacgac gctcttccga tctcagttaa cgtcttcctt ctctctct     48
```

<210> SEQ ID NO 235
<211> LENGTH: 46
<212> TYPE: DNA
<213> ORGANISM: artificial
<220> FEATURE:
<223> OTHER INFORMATION: synthetic

<400> SEQUENCE: 235

```
ttcagacgtg tgctcttccg atctgcaaag cagaaactca catcga       46
```

<210> SEQ ID NO 236
<211> LENGTH: 41
<212> TYPE: DNA
<213> ORGANISM: artificial
<220> FEATURE:
<223> OTHER INFORMATION: synthetic

<400> SEQUENCE: 236

```
cctacacgac gctcttccga tctcacactg acgtgcctct c            41
```

<210> SEQ ID NO 237
<211> LENGTH: 46
<212> TYPE: DNA
<213> ORGANISM: artificial
<220> FEATURE:
<223> OTHER INFORMATION: synthetic

<400> SEQUENCE: 237

```
ttcagacgtg tgctcttccg atcttctttg tgttcccgga catagt       46
```

<210> SEQ ID NO 238
<211> LENGTH: 46
<212> TYPE: DNA
<213> ORGANISM: artificial
<220> FEATURE:
<223> OTHER INFORMATION: synthetic

<400> SEQUENCE: 238

```
cctacacgac gctcttccga tcttctgttt cagggcatga actact       46
```

<210> SEQ ID NO 239
<211> LENGTH: 49
<212> TYPE: DNA

```
<213> ORGANISM: artificial
<220> FEATURE:
<223> OTHER INFORMATION: synthetic

<400> SEQUENCE: 239
ttcagacgtg tgctcttccg atcttccttc tgcatggtat tctttctct                    49

<210> SEQ ID NO 240
<211> LENGTH: 51
<212> TYPE: DNA
<213> ORGANISM: artificial
<220> FEATURE:
<223> OTHER INFORMATION: synthetic

<400> SEQUENCE: 240
cctacacgac gctcttccga tctgtggaaa aatagcctca attcttacca t                 51

<210> SEQ ID NO 241
<211> LENGTH: 54
<212> TYPE: DNA
<213> ORGANISM: artificial
<220> FEATURE:
<223> OTHER INFORMATION: synthetic

<400> SEQUENCE: 241
ttcagacgtg tgctcttccg atctacctca gatatatttc ttcatgaaga cctc             54

<210> SEQ ID NO 242
<211> LENGTH: 51
<212> TYPE: DNA
<213> ORGANISM: artificial
<220> FEATURE:
<223> OTHER INFORMATION: synthetic

<400> SEQUENCE: 242
cctacacgac gctcttccga tctacccacc tataatggtg aatatcttca a                 51

<210> SEQ ID NO 243
<211> LENGTH: 50
<212> TYPE: DNA
<213> ORGANISM: artificial
<220> FEATURE:
<223> OTHER INFORMATION: synthetic

<400> SEQUENCE: 243
ttcagacgtg tgctcttccg atctgagaaa cctgtctctt ggatattctc                   50

<210> SEQ ID NO 244
<211> LENGTH: 51
<212> TYPE: DNA
<213> ORGANISM: artificial
<220> FEATURE:
<223> OTHER INFORMATION: synthetic

<400> SEQUENCE: 244
cctacacgac gctcttccga tctgtcctgc accagtaata tgcatattaa a                 51

<210> SEQ ID NO 245
<211> LENGTH: 54
<212> TYPE: DNA
<213> ORGANISM: artificial
<220> FEATURE:
<223> OTHER INFORMATION: synthetic

<400> SEQUENCE: 245
ttcagacgtg tgctcttccg atctctgctg aaaatgactg aatataaact tgtg             54
```

```
<210> SEQ ID NO 246
<211> LENGTH: 16
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(16)
<223> OTHER INFORMATION: D-Lysine modified

<400> SEQUENCE: 246
ttcggctgcc tcctgg                                                      16

<210> SEQ ID NO 247
<211> LENGTH: 16
<212> TYPE: DNA
<213> ORGANISM: artificial
<220> FEATURE:
<223> OTHER INFORMATION: synthetic
<220> FEATURE:
<221> NAME/KEY: modified_base
<222> LOCATION: (1)..(16)
<223> OTHER INFORMATION: D-Lysine and oxy-aza modified

<400> SEQUENCE: 247
ttcggctgcc tcctgg                                                      16
```